(12) United States Patent
Bolk et al.

(10) Patent No.: US 7,750,170 B2
(45) Date of Patent: Jul. 6, 2010

(54) PROCESS FOR MIXING AN OXIDANT HAVING EXPLOSIVE POTENTIAL WITH A HYDROCARBON

(75) Inventors: Jeroen Willem Bolk, Amsterdam (NL); Alouisius Nicolaas Renée Bos, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 11/613,809

(22) Filed: Dec. 20, 2006

(65) Prior Publication Data

US 2007/0203379 A1    Aug. 30, 2007

Related U.S. Application Data

(60) Provisional application No. 60/752,977, filed on Dec. 22, 2005.

(51) Int. Cl.
    *C07D 301/08*      (2006.01)
(52) U.S. Cl. .................. 549/523; 422/224; 422/234
(58) Field of Classification Search ................ 549/523; 422/224, 234
See application file for complete search history.

(56) References Cited

U.S. PATENT DOCUMENTS

| | | | |
|---|---|---|---|
| 4,033,903 A | 7/1977 | Maxwell | 252/476 |
| 4,061,659 A | 12/1977 | Nielsen et al. | 260/348.34 |
| 4,283,580 A | 8/1981 | Odanaka et al. | 568/858 |
| 4,324,699 A | 4/1982 | Mross et al. | 252/463 |
| 4,376,209 A | 3/1983 | Watanabe et al. | 549/534 |
| 4,508,927 A | 4/1985 | Bhise et al. | 568/858 |
| 4,551,566 A | 11/1985 | Robson et al. | 568/867 |
| 4,760,200 A | 7/1988 | Keen et al. | 568/867 |
| 4,761,394 A | 8/1988 | Lauritzen | 502/348 |
| 4,892,954 A | 1/1990 | Brindöpke et al. | 549/229 |
| 4,982,021 A | 1/1991 | Best et al. | 568/867 |
| 5,023,345 A | 6/1991 | Harvey | 549/230 |
| 5,262,551 A | 11/1993 | Horrell, Jr. et al. | 549/534 |
| 5,292,904 A | 3/1994 | Sawada et al. | 549/534 |
| 5,488,184 A | 1/1996 | Reman et al. | 568/867 |
| 5,597,773 A | 1/1997 | Evans et al. | 502/348 |
| 5,703,253 A | 12/1997 | Evans et al. | 549/536 |
| 5,840,932 A | 11/1998 | Evans et al. | 549/512 |
| 6,153,801 A | 11/2000 | Van Kruchten | 568/867 |
| 6,192,596 B1 | 2/2001 | Bennett et al. | 34/76 |
| 6,265,592 B1 | 7/2001 | Birnbach et al. | 549/230 |
| 6,407,279 B1 | 6/2002 | Buchanan et al. | 558/277 |
| 6,488,838 B1 | 12/2002 | Tonkovich et al. | 208/108 |
| 6,680,044 B1 | 1/2004 | Tonkovich et al. | 423/652 |
| 6,713,036 B1 | 3/2004 | Vanden Bussche et al. | 423/584 |
| 6,749,814 B1 | 6/2004 | Bergh et al. | 422/130 |
| 6,806,087 B2 | 10/2004 | Kibby et al. | 436/37 |
| 6,984,363 B2 | 1/2006 | Tonkovich et al. | 422/173 |
| 7,014,835 B2 | 3/2006 | Mathias et al. | 423/652 |
| 7,288,231 B2 | 10/2007 | Tonkovich et al. | 422/177 |
| 7,294,734 B2 | 11/2007 | Brophy et al. | 558/317 |
| 7,459,589 B2 | 12/2008 | Ramakers | 568/897 |
| 2001/0020102 A1 | 9/2001 | Kawabe | 549/230 |
| 2002/0106316 A1 | 8/2002 | Billig et al. | 422/198 |
| 2003/0072246 A1 | 4/2003 | Nishiwaki et al. | 369/112.26 |
| 2004/0049061 A1 | 3/2004 | Lockemeyer et al. | 549/536 |
| 2004/0076562 A1 | 4/2004 | Manzanec et al. | 422/211 |
| 2004/0099712 A1 | 5/2004 | Tonkovich et al. | 228/193 |
| 2004/0220434 A1* | 11/2004 | Brophy et al. | 568/959 |
| 2005/0133457 A1* | 6/2005 | Tonkovich et al. | 210/739 |
| 2005/0244304 A1 | 11/2005 | Tonkovich et al. | 422/100 |
| 2005/0265915 A1 | 12/2005 | Tonkovich et al. | 423/584 |
| 2005/0272965 A1 | 12/2005 | Watson et al. | 585/658 |
| 2006/0036106 A1 | 2/2006 | Mazanec et al. | 549/533 |
| 2006/0067861 A1 | 3/2006 | Tonkovich et al. | 422/173 |
| 2006/0147370 A1 | 7/2006 | Mathias et al. | 423/650 |
| 2007/0151451 A1 | 7/2007 | Rekers et al. | 95/141 |
| 2007/0154377 A1 | 7/2007 | Rekers | 423/245.3 |
| 2007/0197801 A1 | 8/2007 | Bolk et al. | 549/229 |
| 2007/0197808 A1 | 8/2007 | Bolk et al. | 549/536 |
| 2007/0203348 A1 | 8/2007 | Bolk et al. | 549/533 |
| 2007/0203349 A1 | 8/2007 | Bolk et al. | 549/533 |
| 2007/0203350 A1 | 8/2007 | Bolk et al. | 549/533 |
| 2007/0203352 A1 | 8/2007 | Bolk et al. | 549/535 |

(Continued)

FOREIGN PATENT DOCUMENTS

EP      0069494      1/1983

(Continued)

OTHER PUBLICATIONS

Kursawe A. et al, "Comparison of Ag/Al- and Ag/α-A1203 5—Catalytic Surfaces for the Partial Oxidation of Ethene in Microchannel Reactors", Microreaction Technology: IMRET Proceedings of the 5th Int. Conf. on Microreaction Technology (Eds. M. Matlosz, W. Ehrfeld, J. P. Beselt), Springer-Verlag Berlin Heidelberg New York 2001, pp. 240-251, ISPB 3-540-42498-9.

(Continued)

*Primary Examiner*—Janet L Andres
*Assistant Examiner*—David E Gallis

(57) ABSTRACT

The invention provides a process for the mixing of an oxidant having explosive potential with a hydrocarbon material, which comprises conveying a first stream comprising the hydrocarbon material and a second stream comprising the oxidant into a microchannel apparatus, allowing mixing to occur, and withdrawing the mixture. The process is useful for the preparation of ethylene oxide.

9 Claims, 6 Drawing Sheets

U.S. PATENT DOCUMENTS

| | | | |
|---|---|---|---|
| 2007/0203372 A1 | 8/2007 | Ramakers | 568/867 |
| 2007/0203379 A1 | 8/2007 | Bolk et al. | 585/500 |
| 2007/0213545 A1 | 9/2007 | Bolk et al. | 549/536 |
| 2008/0031788 A1 | 2/2008 | Brophy et al. | 422/207 |
| 2008/0064881 A1 | 3/2008 | Van Kruchten | 549/230 |
| 2008/0097129 A1 | 4/2008 | Van Kruchten | 568/858 |
| 2008/0154051 A1 | 6/2008 | Bolk et al. | 549/524 |
| 2008/0154052 A1 | 6/2008 | Bolk et al. | 549/524 |

FOREIGN PATENT DOCUMENTS

| | | |
|---|---|---|
| EP | 0156449 | 10/1985 |
| EP | 266015 | 5/1988 |
| EP | 0501757 | 9/1992 |
| EP | 0532325 | 3/1993 |
| EP | 1281922 A2 | 2/2003 |
| EP | 1632282 | 3/2006 |
| FR | 2851564 | 8/2004 |
| GB | 1076809 | 7/1967 |
| GB | 1449091 | 9/1976 |
| GB | 2107712 | 5/1983 |
| GB | 2297278 | 2/1996 |
| GB | 2433501 | 12/2006 |
| GB | 2433502 | 12/2006 |
| GB | 2433503 | 12/2006 |
| GB | 2433739 | 12/2006 |
| GB | 2433902 | 12/2006 |
| GB | 2441527 | 12/2006 |
| JP | 5692228 | 7/1981 |
| JP | 59013741 | 1/1984 |
| JP | 2004275933 | 10/2004 |
| WO | WO 91/19706 | 12/1991 |
| WO | WO9604074 | 2/1996 |
| WO | WO9730275 | 8/1997 |
| WO | WO9964147 | 12/1999 |
| WO | WO0196324 | 12/2001 |
| WO | WO0218042 | 3/2002 |
| WO | WO02087729 | 11/2002 |
| WO | WO03000641 | 1/2003 |
| WO | WO0349835 | 6/2003 |
| WO | WO03072246 | 9/2003 |
| WO | WO2004002954 | 1/2004 |
| WO | WO2004016347 | 2/2004 |
| WO | WO2004037418 | 5/2004 |
| WO | WO2004039497 | 5/2004 |
| WO | WO2004039790 | 5/2004 |
| WO | WO2004041414 | 5/2004 |
| WO | WO2004099113 | 11/2004 |
| WO | WO2004101144 | 11/2004 |
| WO | WO2004101481 | 11/2004 |
| WO | WO2004103539 | 12/2004 |
| WO | WO2004103549 | 12/2004 |
| WO | WO2005003113 | 1/2005 |
| WO | WO2005051939 | 6/2005 |
| WO | WO2005060658 | 7/2005 |
| WO | WO2005082519 | 9/2005 |
| WO | WO2005105665 | 11/2005 |
| WO | WO2006020709 | 2/2006 |
| WO | WO2006042598 | 4/2006 |
| WO | WO2006053345 | 5/2006 |
| WO | WO2006055609 | 5/2006 |
| WO | WO2006065387 | 6/2006 |
| WO | WO2006102189 | 9/2006 |
| WO | WO2006102675 | 9/2006 |
| WO | WO2006127889 | 11/2006 |
| WO | WO2006133183 | 12/2006 |
| WO | WO2006133187 | 12/2006 |
| WO | WO2007071744 | 6/2007 |
| WO | WO2007076393 | 7/2007 |
| WO | WO2007076395 | 7/2007 |

OTHER PUBLICATIONS

Kestenbaum H., et al, "Silver-Catalyzed Oxidation of Ethylene to Ethylene Oxide in a Microreaction System", Ind. Eng. Chem. Res. 41 (2002), pp. 710-719.

Notice of Allowance for TS1943, dated Apr. 10, 2008, U.S. Appl. No. 11/613,835, filed Dec. 20, 2006.

International Search Report dated Sep. 11, 2007 for PCT/US2006/062401 (TH3187 PCT).

Written Opinion dated Sep. 11, 2007 for PCT/US2006/062401 (TH3187 PCT).

Office Communication for TH3186, dated Mar. 4, 2008, U.S. Appl. No. 11/613,741, filed Dec. 20, 2006.

Office Action of Mar. 11, 2009, U.S. Appl. No. 11/613,461 filed Dec. 20, 2006.

Office Action of Aug. 29, 2008, U.S. Appl. No. 11/613,509 filed Dec. 20, 2006.

Office Action of Aug. 28, 2008, U.S. Appl. No. 11/613,641 filed Dec. 20, 2006.

Office Action of Aug. 19, 2008, U.S. Appl. No. 11/613,699 filed Dec. 20, 2006.

Office Action of Aug. 29, 2008, U.S. Appl. No. 11/613,721 filed Dec. 20, 2006.

Office Action of Oct. 15, 2008, U.S. Appl. No. 11/613,750 filed Dec. 20, 2006.

Office Action of Feb. 2, 2009, U.S. Appl. No. 11/613,791 filed Dec. 20, 2006.

* cited by examiner

PROCESS FOR MIXING AN OXIDANT HAVING EXPLOSIVE POTENTIAL WITH A HYDROCARBON

REFERENCE TO PRIOR APPLICATIONS

This application claims the benefit of U.S. Provisional Application No. 60/752,977 filed Dec. 22, 2005.

FIELD OF THE INVENTION

The present invention relates to improvements in process operations involving particularly hydrocarbons. The process improvements envisaged find especial application in the production of olefin oxide from olefin and oxygen and in its optional further conversion.

BACKGROUND OF THE INVENTION

When operating on a commercial scale, process operations have to meet a number of important design criteria. In the modem day environment, process design has to take account of environmental legislation and keep to health and safety standards. Processes that utilize or produce dangerous chemicals pose particular problems and often, in order to minimize risks of explosion or reaction runaway, such process operations have to be run at conditions that are not optimal; this increases the running costs of a plant (the operational expenditure or OPEX). Such processes may also have to utilize more equipment than is necessary just to perform the process; this leads to an increase in building costs (the capital expenditure or CAPEX).

There is an on-going need to provide process operations that can reduce CAPEX and OPEX costs and particularly without increasing the risk of damage to the plant and danger to the public and/or to the process plant workers.

SUMMARY OF THE INVENTION

The present invention provides for the utilization of microchannel apparatus in process operations. Such apparatus have previously been proposed for use in certain specific fields of application but have not previously been proposed to provide the combination of reduced CAPEX and/or OPEX with maintained or reduced plant safety risks.

The invention provides a process for the mixing of an oxidant having explosive potential with a hydrocarbon material, which comprises conveying a first stream comprising the hydrocarbon material and a second stream comprising the oxidant into a microchannel apparatus, allowing mixing to occur, and withdrawing the mixture. This process finds special advantage when applied to the mixing of oxygen into the gas recycle stream in an ethylene oxide production plant.

DETAILED DESCRIPTION OF THE INVENTION

The present invention provides, in a number of aspects, processes that utilize microchannel apparatus. In a number of these processes the microchannel apparatus may house a chemical reaction and optionally may also contain catalytic components; in other processes the microchannel apparatus are utilized for physical operations. Hereinafter a discussion of such apparatus is given and reference is made generally to 'microchannel reactors'; this term will be understood to encompass microchannel apparatus whether utilized for physical processes or for chemical reaction processes, with or without a catalytic component.

Microchannel reactors suitable for use in this invention and their operation have been described in WO-A-2004/099113, WO-A-01/12312, WO-01/54812, U.S. Pat. No. 6,440,895, U.S. Pat. No. 6,284,217, U.S. Pat. No. 6,451,864, U.S. Pat. No. 6,491,880, U.S. Pat. No. 6,666,909, U.S. Pat. No. 6,811,829, U.S. Pat. No. 6,851,171, U.S. Pat. No. 6,494,614, U.S. Pat. No. 6,228,434 and U.S. Pat. No. 6,192,596. Methods by which the microchannel reactor may be manufactured, loaded with catalyst, and operated, as described in these references, may generally be applicable in the practice of the present invention.

Figure 1:
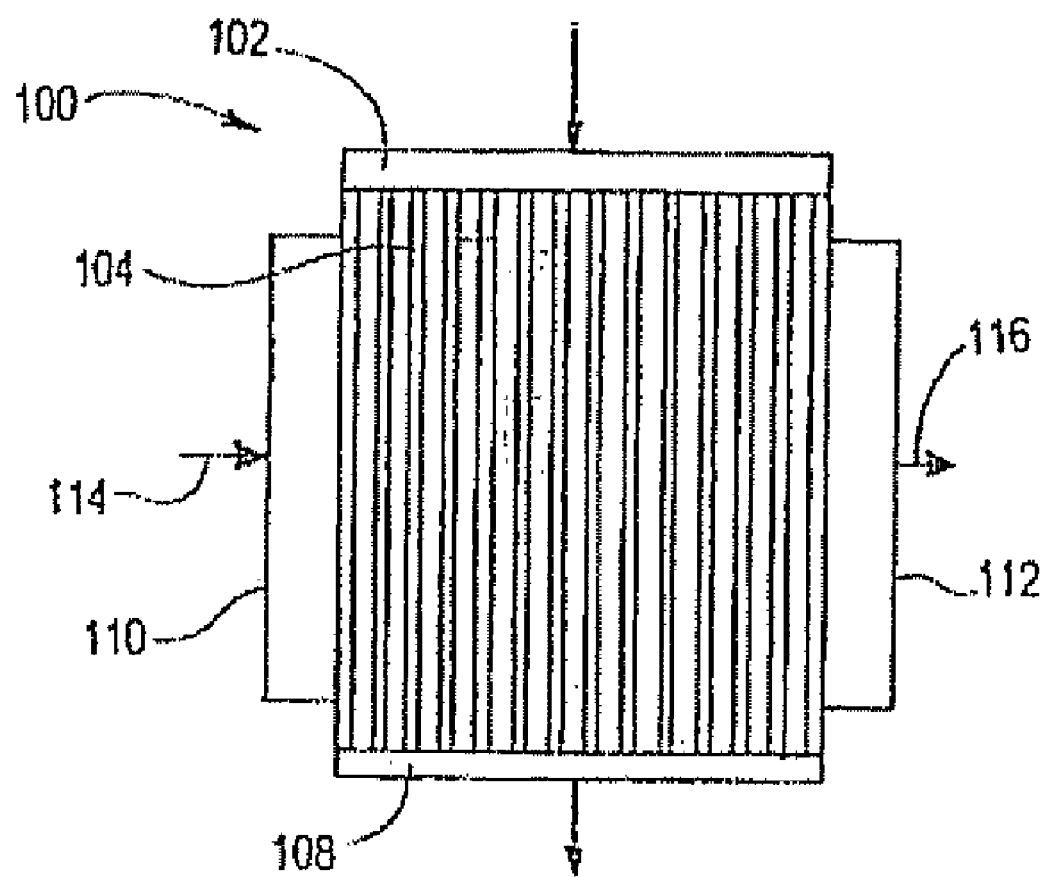
FIG. 1 shows a schematic drawing of a microchannel reactor and its main constituents.

With reference to FIG. 1, microchannel reactor 100 may be comprised of a header 102, a plurality of process microchannels 104, and a footer 108. The header 102 provides a passageway for fluid to flow into the process microchannels 104. The footer 108 provides a passageway for fluid to flow from the process microchannels 104.

The number of process microchannels contained in a microchannel reactor may be very large. For example, the number may be up to $10^5$, or even up to $10^6$ or up to $2 \times 10^6$. Normally, the number of process microchannels may be at least 10 or at least 100, or even at least 1000.

The process microchannels are typically arranged parallel, for example they may form an array of planar microchannels. Each of the process microchannels may have at least one internal dimension of height or width of up to 15 mm, for example from 0.05 to 10 mm, in particular from 0.1 to 5 mm, more in particular from 0.5 to 2 mm. The other internal dimension of height or width may be, for example, from 0.1 to 100 cm, in particular from 0.2 to 75 cm, more in particular from 0.3 to 50 cm. The length of each of the process microchannels may be, for example, from 1 to 500 cm, in particular from 2 to 300 cm, more in particular from 3 to 200 cm, or from 5 to 100 cm.

The microchannel reactor 100 additionally comprises heat exchange channels (not shown in FIG. 1) which are in heat exchange contact with the process microchannels 104. The heat exchange channels may be microchannels. The microchannel reactor is adapted such that heat exchange fluid can flow from heat exchange header 110 through the heat exchange channels to heat exchange footer 112. The heat exchange channels may be aligned to provide a flow in a co-current, counter-current or, in some aspects, preferably cross-current direction, relative to a flow in the process microchannels 104. The cross-current direction is as indicated by arrows 114 and 116.

Each of the heat exchange channels may have at least one internal dimension of height or width of up to 15 mm, for example from 0.05 to 10 mm, in particular from 0.1 to 5 mm, more in particular from 0.5 to 2 mm. The other internal dimension of height or width may be, for example, from 0.1 to 100 cm, in particular from 0.2 to 75 cm, more in particular from 0.3 to 50 cm. The length of each of the heat exchange channels may be, for example, from 1 to 500 cm, in particular from 2 to 300 cm, more in particular from 3 to 200 cm, or from 5 to 100 cm.

The separation between each process microchannel 104 and the next adjacent heat exchange channel may be in the range of from 0.05 mm to 5 mm, in particular from 0.2 to 2 mm.

In some embodiments of this invention, there is provided for first heat exchange channels and second heat exchange channels, or first heat exchange channels, second heat exchange channels and third heat exchange channels, or even up to fifth heat exchange channels, or even further heat exchange channels. Thus, in such cases, there is a plurality of sets of heat exchange channels, and accordingly there may be a plurality of heat exchange headers 110 and heat exchange footers 112, whereby each set of heat exchange channels may be adapted to receive heat exchange fluid from a heat exchange header 110 and to deliver heat exchange fluid into a heat exchange footer 112.

The header 102, footer 108, heat exchange header 110, heat exchange footer 112, process microchannels 104 and heat exchange channels may independently be made of any construction material which provides sufficient strength, optionally dimensional stability, and heat transfer characteristics to permit operation of the processes in accordance with this invention. Suitable construction materials include, for example, steel (for example stainless steel and carbon steel), monel, titanium, copper, glass and polymer compositions. The kind of heat exchange fluid is not material to the present invention and the heat exchange fluid may be selected from a large variety. Suitable heat exchange fluids include steam, water, air and oils. In embodiments of the invention which include a plurality of sets of heat exchange channels, such sets of heat exchange channels may operate with different heat exchange fluids or with heat exchange fluids having different temperatures.

Figure 2:
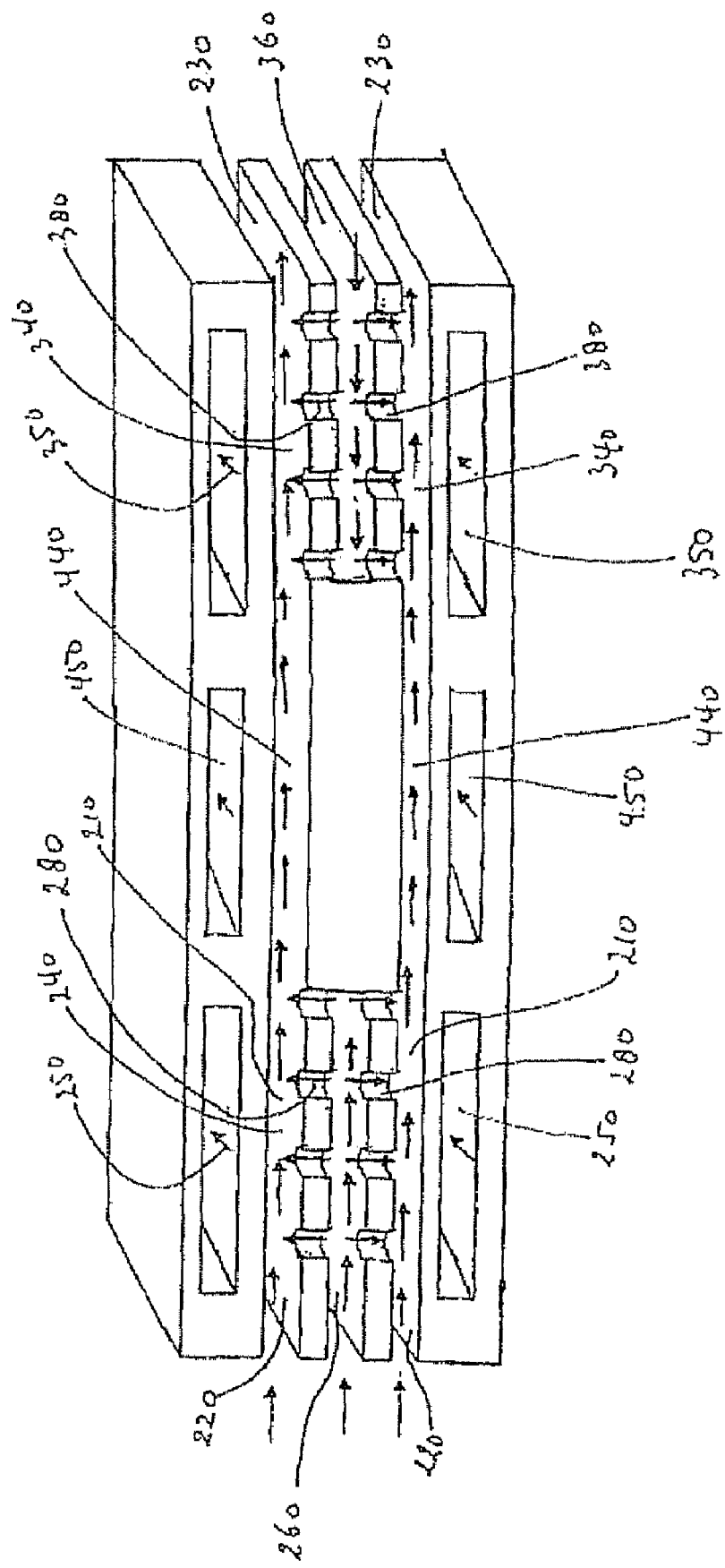
FIG. 2 shows a schematic drawing of a typical example of a repeating unit which comprises process microchannels and heat exchange channels and its operation when in use in the practice of the invention. A microchannel apparatus or reactor utilized in this invention may comprise a plurality of such repeating units.

A microchannel reactor of use in the invention may comprise a plurality of repeating units each comprising one or more process microchannels and one or more heat exchange channels. Reference is now made to FIG. 2, which shows a typical repeating unit and its operation.

Process microchannels 210 have an upstream end 220 and a downstream end 230 and may comprise of a first section 240 which may optionally, for certain aspects of the present invention, contain a catalyst (not shown). First section 240 may be in heat exchange contact with first heat exchange channel 250, allowing heat exchange between first section 240 of process microchannel 210 and first heat exchange channel 250. The repeating unit may comprise first feed channel 260 which leads into first section 240 through one or more first orifices 280. Typically one or more first orifices 280 may be positioned downstream relative to another first orifice 280. During operation, feed may enter into first section 240 of process microchannel 210 through an opening in upstream end 220 and/or through first feed channel 260 and one or more first orifices 280.

Process microchannels 210 may comprise a second section 340 which may or may not be adapted to contain a catalyst. Second section 340 is positioned down stream of first section 240. Second section 340 may be in heat exchange contact with second heat exchange channel 350, allowing heat exchange between second section 340 of process microchannel 210 and second heat exchange channel 350. In some embodiments second section 340 is adapted to quench product obtained in and received from first section 240 by heat exchange with a heat exchange fluid in second heat exchange channel 350. Quenching if required may be achieved in stages by the presence of a plurality of second heat exchange channels 350, for example two or three or four. Such a plurality of second heat exchange channels 350 may be adapted to contain heat exchange fluids having different temperatures, in particular such that in downstream direction of second section 340 heat exchange takes place with a second heat exchange channel 350 containing a heat exchange fluid having a lower temperature. The repeating unit may comprise second feed channel 360 which leads into second section 340 through one or more second orifices 380. During operation, feed may enter into second section 340 from upstream in process microchannel 210 and through second feed channel 360 and one or more second orifices 380.

The first and second feed channels 260 or 360 in combination with first and second orifices 280 or 380 whereby one or more first or second orifices 280 or 380 are positioned downstream to another first or second orifice 280 or 380, respectively, allow for replenishment of a reactant. Replenishment of a reactant can be utilized in some embodiments of this invention.

Process microchannels 210 may comprise an intermediate section 440, which is positioned downstream of first section 240 and upstream of second section 340. Intermediate section 440 may be in heat exchange contact with third heat exchange channel 450, allowing heat exchange between intermediate section 440 of the process microchannel 210 and third heat exchange channel 450.

In some embodiments, process microchannel 210 may comprise a third section (not drawn) downstream of second section 340, and optionally a second intermediate section (not drawn) downstream of second section 340 and upstream of the third section. The third section may be in heat exchange contact with a fourth heat exchange channel (not drawn), allowing heat exchange between the third section of the process microchannel 210 and fourth heat exchange channel. The second intermediate section may be in heat exchange contact with a fifth heat exchange channel (not drawn), allowing heat exchange between the second intermediate section of the process microchannel 210 and fifth heat exchange channel. The repeating unit may comprise a third feed channel (not drawn) which ends into the third section through one or more third orifices (not drawn). Typically one or more third orifices may be positioned downstream relative to another third orifice. During operation, feed may enter into the third section from upstream in process microchannel 210 and through the third feed channel and the one or more third orifices.

Each of the feed channels may be a microchannel. They may have at least one internal dimension of height or width of up to 15 mm, for example from 0.05 to 10 mm, in particular from 0.1 to 5 mm, more in particular from 0.5 to 2 mm. The other internal dimension of height or width may be, for example, from 0.1 to 100 cm, in particular from 0.2 to 75 cm, more in particular from 0.3 to 50 cm. The length of each of the feed channels may be, for example, from 1 to 250 cm, in particular from 2 to 150 cm, more in particular from 3 to 100 cm, or from 5 to 50 cm.

The length of each of the sections of the process microchannels may be selected independently of each other, in accordance with, for example, the heat exchange capacity needed or the quantity of catalyst which may be contained in the section. The lengths of the sections may independently be at least 1 cm, or at least 2 cm, or at least 5 cm. The lengths of the sections may independently be at most 250 cm, or at most 150 cm, or at most 100 cm, or at most 50 cm. Other dimensions of the sections are defined by the corresponding dimensions of process microchannel 210.

The microchannel reactor of this invention may be manufactured using known techniques, for example conventional machining, laser cutting, molding, stamping and etching and combinations thereof. The microchannel reactor of this invention may be manufactured by forming sheets with features removed which allow passages. A stack of such sheets may be assembled to form an integrated device, by using known techniques, for example diffusion bonding, laser welding, cold welding, diffusion brazing, and combinations thereof. The microchannel reactor of this invention comprises appropriate headers, footers, valves, conduit lines, and other features to control input of reactants, output of product, and flow of heat exchange fluids. These are not shown in the drawings, but they can be readily provided by those skilled in the art. Also, there may be further heat exchange equipment (not shown in the drawings) for temperature control of feed, in particular for heating feed or feed components, before it enters the process microchannels, or for temperature control of product, in particular for cooling product, after it has left the process microchannels. Such further heat exchange equipment may be integral with the microchannel reactor, but more typically it will be separate equipment. These are not shown in the drawings, but they can be readily provided by those skilled in the art.

Where catalyst is present, it may be in any suitable form to be accommodated in one or more of the process microchannels. Such catalyst may be installed by any known technique in the designated section of the process microchannels. The catalyst may be in solid form and form a packed bed in the designated section of the process microchannels and/or may form a coating on at least a portion of the wall of the designated section of the process microchannels. Alternatively the catalyst may be in the form of a coating on inserts which may be positioned in the designated section of the microchannel apparatus. Coatings may be prepared by any suitable deposition method such as wash coating or vapor deposition. Where a catalyst is comprised of several catalytically effective components, deposition may be achieved by deposition of a first catalytic component, e.g. a metal or metal component, on at least a portion of the wall of the designated section of the process microchannels with the deposition of one or more additional catalyst components on at least the same wall prior to, together with, or subsequent to that of the first component.

In some embodiments the catalyst may be homogeneous and not in solid form in which case the catalyst may be fed to the designated section of the process microchannels together with one or more components of the relevant feed or process stream and may pass through the microchannels along with the reaction mixture or process stream.

The present invention in certain aspects finds especial application in a process for the manufacture of alkylene oxide, and especially ethylene oxide, by the direct epoxidation of alkylene using oxygen or air, see Kirk-Othmer Encyclopedia of Chemical Technology, 3$^{rd}$ edition, Volume 9, 1980, pages 445 to 447. In the air-based process, air or air enriched with oxygen is employed as a source of the oxidizing agent while in the oxygen-based processes, high purity (at least 95 mole %) oxygen is employed as the source of the oxidizing agent. Currently most epoxidation plants are oxygen-based. The epoxidation process may be carried out using reaction temperatures selected from a wide range. Preferably the reaction temperature within the epoxidation reactor is in the range of from 150° C. to 340° C., more preferably in the range of from 180 to 325° C. The reaction is preferably carried out at a pressure of in the range of from 1000 to 3500 kPa.

The mixing of oxidants and hydrocarbon materials is a hazardous process. Where the oxidant is particularly oxygen gas, the mixing process has to be strictly controlled to minimize the mixing volume of oxygen gas following addition to the hydrocarbon material.

Considering the mixing of oxygen gas and a hydrocarbon material such as ethylene, a mixture of the two materials has a minimum and a maximum oxygen level between which the mixture can become explosive. Prior to mixing, the oxygen stream has an oxygen level that exceeds the upper explosion limit, following mixing the aim would be for the oxygen level to be below the lower explosion limit. However during mixing there will inevitably be a stage where the mixture will have an oxygen level that lies in the explosive region.

It is therefore advantageous to have a mixing process that minimizes the length of time that an oxidant-hydrocarbon mixture exists in the relevant explosive region.

In the commercial production of ethylene oxide, oxygen is reacted with ethylene in extremely large volumes. In commercial operations this reaction is currently performed by addition of oxygen gas to a gas stream that contains ethylene and a ballast gas which may comprise one or more of nitrogen, carbon dioxide and methane. Additionally the gas stream may also contain other gases such as ethane, oxygen, and argon following recycle, see U.S. Pat. No. 3,119,837 and EP-A-893,443 for example. Minimizing the risk of explosion following addition of significant volumes of oxygen gas to the gas stream is of prime concern. Specific devices have been developed to ensure rapid mixing and to minimize the volume of gas in the gas stream that exists in the explosive region i.e. to minimize the volume of not fully mixed gases. One such device is a mixing device in the shape of a ring or 'doughnut', see Research Disclosure No. 465117, Research Disclosure Journal, January 2003, page 106, Kenneth Mason Publications Ltd. However with such devices the large volume of oxygen gas is still directly mixed into the gas flow, and there is still a region in the gas stream where the oxygen-gas mixture can be explosive, owing to pockets of not fully mixed gases.

By the use of microchannel apparatus, mixing of oxidant and hydrocarbon occurs in one or more individual process microchannels. Preferably the oxidant and the hydrocarbon are in the gas phase. The oxidant stream and the hydrocarbon stream are desirably added via separate feed lines to common process microchannels. Since there exists a large number of process microchannels within a microchannel apparatus, the oxidant feed and the hydrocarbon feed is split up into multiple small volumes for the mixing to occur in individual process microchannels. This ensures a high efficiency of mixing and where the feeds are gases minimizes the volume of gas that is in the explosive region. Inside the microchannels, explosion cannot take place as heat is immediately dissipated and the flame quenched making the apparatus intrinsically safe. When fully mixed, the mixture from each process microchannel will converge into one stream either within the microchannel apparatus or via a header into an external exit line, and a fully mixed stream is provided with minimal explosive risk.

Having regard to FIG. 2 herewith, it is possible, for example, for one of the two feed streams, preferably the hydrocarbon stream, to enter one microchannel section 240 via process microchannels 260 and/or 220, and for this feed to be led via intermediate section 440 into a second section 340 wherein the other of the two feeds, preferably the oxidant, is introduced via second feed channel 360. Mixing of the two feeds can then occur in the microchannel 230 to which the second feed is directed via orifices 380. If necessary for the feed components involved or to provide enhanced safety, the microchannel apparatus may also comprise heat exchange channels, which may themselves be microchannels, through which a cooling medium can be run.

In the present invention, the oxidant is most preferably oxygen gas. A hydrocarbon or hydrocarbon material herein may be any organic compound that contains hydrogen and carbon; other elements such as oxygen may also be present. In this aspect of the present invention a hydrocarbon material may be one or more of hydrocarbons such as $C_{1-10}$ hydrocarbons, for example methane, ethylene, ethane, propylene, propane and butane; oxides such as $C_{2-10}$ alkylene oxides, for example ethylene oxide; glycols such as $C_{2-10}$ alkylene glycols for example mono-, di- or tri-ethylene glycol; and $C_{1-10}$ organic acids such as acetic acid. Thus, the process of the present invention may for example be utilized in the catalytic partial oxidation of ethylene to ethylene oxide or to vinyl acetate.

The present invention most suitably provides a process for the preparation of ethylene oxide, which comprises introducing a source of oxygen into one or more process microchannels of a microchannel apparatus and introducing into the same process microchannels a source of ethylene, allowing mixing to take place to form a gaseous product mixture, and conveying the gaseous product mixture to a reaction region wherein reaction to ethylene oxide can occur. Preferably the source of ethylene comprises a mixture of ethylene and one or more compounds selected from methane, ethane, oxygen, argon, carbon dioxide and nitrogen. The process of the present invention is most preferably utilized where the source of oxygen is oxygen gas having a purity in the range of from 95 to 99.99% by volume; however the oxygen source may also be air or oxygen gas of a lower purity, for example of 85% by volume and above, and thus preferably the oxygen source is a gas having an oxygen content in the range of from 15 to 99.99% by volume.

In this aspect of the present invention, the gases are mixed on a 'microlevel', i.e. on a very small scale, within process microchannels of the microchannel apparatus. Initially after intermingling of both feeds there will of course be pockets of oxygen-rich and oxygen-poor mixtures, however the splitting up and recombination of the oxygen flow in the process microchannels and, where present, via the microchannel orifices, will establish an average oxygen concentration below explosion limits. As the gas mixture progresses through the microchannel apparatus, these pockets will disappear and the gases will become well-mixed on a microlevel.

In an EO manufacturing plant, it is most useful to locate the microchannel apparatus in the recycle gas loop at the same location where conventional mixing apparatus is utilized i.e. prior to the reactor. However it is possible to locate the microchannel apparatus at any location in the recycle gas loop. In certain locations the conditions of the gas, for example its composition, pressure and/or temperature, could cause even the final well-mixed gas to be in the explosive region; in such circumstances it may be necessary to adjust the conditions to allow the process of the invention to be used, for example to reduce the temperature of the recycle gas stream. A feed line suitably runs from the ethylene source into the apparatus, and a separate feed line is provided from the oxygen source. The general process conditions that may apply for the mixing operation are suitably a pressure in the range of from 1000 to 3500 kPa, and a temperature in the range of from ambient (20° C.) to 250° C.

The process of the present invention provides enhanced mixing in a rapid timescale, and indeed is able to provide a fully mixed product in a shorter timescale than previous proposals, particularly for the mixing of gases having an explosive potential.

Thus the use of the microchannel apparatus provides the advantage of rapidly splitting up the feed gases and mixing small volumes together at a much faster rate than is achievable by the prior ring mixing devices. The length of time that any mixture may exist in the explosive region is significantly reduced and the finally fully mixed gas stream is achieved much quicker.

The size of the microchannels themselves additionally ensures that the mixing apparatus functions as a flame arrester. For any gas or gas mixture there is a characteristic flame quench diameter; this is the diameter of pipe or container in which any flame would be quenched. By selection of the appropriate microchannel diameter it can be ensured that any starting combustion reaction can be immediately quenched. Thus the physical nature of a microchannel apparatus additionally may provide intrinsic safety for the mixing operation—this is not at all possible with current mixing systems. Where the microchannel apparatus additionally includes heat exchange channels, the safety advantages are further enhanced.

In a process of the present invention, it is thus preferred to use a microchannel apparatus having one or more, and preferably all, process microchannels having an internal dimension of height and/or width of at most 5 mm, most preferably at most 2 mm, and especially at most 1.5 mm. Said internal dimension is preferably at least 0.1 mm, most preferably at least 0.5 mm, and especially at least 0.5 mm.

Another process operation that presents an explosion risk, particularly in an ethylene oxide plant, is the handling of ethylene oxide itself. Ethylene oxide (EO) is an unstable and very reactive component. In equipment that contains EO vapor, several reactions can occur which are exothermic. Where the heat of reaction is not removed fast enough, the temperature in the equipment can increase rapidly and, if unchecked, can lead to explosive decomposition reactions of the EO vapor. Where additional substances are present then explosive reactions can occur at lower temperatures than for pure ethylene oxide. Even EO liquid under certain circumstances can be dangerous.

In a commercial ethylene oxide production plant, the sections for which this is of most concern are the EO concentrator and the EO purification sections. The EO concentrator is often also called the EO stripper. Both EO concentrator and the EO purification sections utilize a distillation column, to separate EO from water, which may be equipped with a condenser and an EO condensate collection vessel. In the latter, stagnant, liquid EO exists possibly in conjunction with water. In order to reduce the chance of explosive decomposition reactions, whether in a distillation column or in an EO condensate collection vessel, the top section plus overhead system of an EO concentrator column and of an EO purification column are conventionally operated under nitrogen pressure, which increases the operating pressure by at least a factor of 1.7. The pressure can also be generated by use of a gas other than nitrogen, which may be selected from one or more of carbon dioxide, methane and a process gas such as a light ends gas. Usually, however, nitrogen is used. It would be most desirable to be able to operate these columns without the need for pressurization in the top section, yet still have a low explosion risk.

The use of microchannel apparatus has the advantage of being able to cool an ethylene oxide-containing mixture very efficiently, thus minimizing the likelihood of explosive decomposition reactions. Since there exist a large number of process microchannels within a microchannel apparatus, and because of the dimensions of the process microchannels, the EO-containing feed is split up into multiple small volumes. A heat transfer medium is run through heat exchange channels of the apparatus to ensure a rapid heat flux from EO to heat transfer medium. These features ensure a high efficiency of heat transfer and minimize the volume of gas that can be in the explosive region. Furthermore the nature of the process microchannels means that the apparatus can act as a flame arrester and provide an intrinsically safe condensation system for EO-containing gases. In this aspect of the present invention, it is thus also preferred to use a microchannel apparatus having one or more, and preferably all, process microchannels having an internal dimension of height and/or width of at most 5 mm, most preferably at most 2 mm, and especially at most 1.5 mm. Said internal dimension is preferably at least 0.1 mm, most preferably at least 0.5 mm, and especially at least 0.5 mm.

In the process of the present invention, the gaseous mixture comprising ethylene oxide may contain in the range of from 50 to 100% by weight of EO. The gaseous mixture may also comprise one or more of the following, in gaseous form: water; carbon dioxide; argon; nitrogen; oxygen; ethylene glycols such as mono-ethylene glycol, di-ethylene glycol and tri-ethylene glycol; aldehydes such as acetaldehyde, and formaldehyde; hydrocarbons such as ethylene, methane, and ethane; and hydrocarbon materials and/or chlorinated hydrocarbon impurities such as alcohols, acids, acetals, cyclic acetals, ethers, cyclic ethers, esters such as 1,4-di-oxane, 1,4,7-tri-oxane, 1,3-di-oxolane, 2-methyl-1,3-di-oxolane, 2-chloro-methyl-1,3-di-oxolane, 2-chloro-ethanol, 2-chloro-methyl-1,3-di-oxolane, glyoxal, oxalic acid, glycolic acid, glyoxilic acid, lactic acid, acetic acid, formic acid and their esters.

The use of microchannel apparatus can provide a much larger heat transfer than conventional shell and tube heat exchangers, and is a much smaller item of equipment. Thus a CAPEX improvement is given by the combination of smaller condensation equipment as well as by the removal of reflux drums. The apparatus also has the potential to reduce the need for excess pressurization of the upper sections of these columns. The OPEX may also be improved by any reduced pressurization in the top section of these EO distillation columns. Where the pressure can be reduced then there is additional significant advantage, particularly in an EO stripper or concentrator, in that a lower temperature steam can be used to heat the column and the amount of glycol by-product can be reduced. Furthermore the microchannel apparatus acts as a flame arrester and provides an intrinsically safe EO condensation system.

Thus the present invention preferably provides a process for the concentration or purification of ethylene oxide, which comprises a) absorbing ethylene oxide from a first gaseous stream with a suitable absorbent, b) desorption of the ethylene oxide in a distillation unit to form a second gaseous stream containing ethylene oxide, and c) recovering ethylene oxide, wherein the second gaseous stream of step b), is condensed in one or more process microchannels of a microchannel apparatus.

Suitable absorbents that can absorb ethylene oxide are documented in literature and include water (see Research Disclosure No. 465117, idem); ethylene carbonate (see U.S. Pat. No. 4,221,727 and EP-A-776890); propylene carbonate (EP-A-705826); aqueous ethylene glycol solutions having a glycol content up to 40% and antifoam additive content of up to 500 ppm (U.S. Pat. No. 4,875,909 and GB-A-1435848); methanol (U.S. Pat. No. 3,948,621); organic liquid solvents (U.S. Pat. No. 4,249,917); and liquid hydrocarbons such as methane, ethane and/or ethylene in liquid form (U.S. Pat. No. 3,644,432). However, most commonly water or an aqueous solution is utilized and is preferred in the process of the present invention.

In step a) absorption of ethylene oxide with water or an aqueous solution creates an aqueous solution of ethylene oxide. In step b) the ethylene oxide is then desorbed by dewatering in a distillation unit.

A distillation unit may comprise one or more distillation columns. Most suitably a maximum of five distillation columns are utilized in series within a unit forming a 'distillation train'. Preferably a distillation unit comprises from one to three distillation columns, most preferably only one distillation column. Where a single column is utilized in step b) the second gaseous stream is obtained in the upper section of the column, and an aqueous product is given in the bottom section. In a distillation train of columns equivalent product streams are obtained at appropriate points, as would be well known to the skilled person in the art.

The term 'dewatering' herein should be understood to mean the removal of water.

In a preferred embodiment, step a) is the absorption of ethylene oxide in an aqueous solution to produce a stream in which water is enriched with EO and step b) is performed in an EO stripper or concentrator, which is a single distillation column. While the EO is stripped or concentrated from the aqueous feed stream, the product drawn off from the upper section, and preferably drawn off at the very top, of the distillation column is still a mixture of ethylene oxide and water. This gaseous mixture product is condensed in a microchannel apparatus and the resulting EO-containing stream can be utilized for the production of other chemicals such as 1,2-diols, 1,2-diol ethers, 1,2-carbonates or alkanol amines by processes known in the art, or it can be further purified to yield a high purity EO. A portion of said resulting EO-containing stream may be recycled to the EO concentrator column, and a bleed of gases, such as methane, $CO_2$ and ethylene, can be drawn off by procedures well known to those skilled in this art. In this embodiment, the first gaseous stream is an EO-containing product stream of a reactor in which ethylene and oxygen are reacted to form ethylene oxide. Preferably the first gaseous stream comprises EO in the range of from 2 to 50% by weight, more preferably from 2 to 10% by weight, and especially from 4 to 6% by weight. The aqueous solution of step a) primarily comprises water in an amount from 50 to 100% by weight. It is possible that in the range of from 0.1 to 20, e.g. 2 to 10, % by weight of said aqueous solution is a glycol, mostly being mono-ethylene glycol. In such solutions an anti-foam additive is not required but may be utilized if desired.

In an alternative preferred embodiment step b) may be performed several stages downstream of step a) and in the EO purification section of an EO production process, in which case the second gaseous stream will contain predominantly EO, with trace amounts of impurities. Thus less than 10,000 ppm, i.e. for example from 1 ppm to 10,000 ppm, of other compounds may also be present. Such compounds may comprise for example water, carbon dioxide, argon, nitrogen, oxygen, aldehydes, such as acetaldehyde, and formaldehyde, and, as above, other hydrocarbons, alcohols, acids, acetals, cyclic acetals, ethers, cyclic ethers, and esters. In this embodiment, the second gaseous stream is purified ethylene oxide which may be drawn off at any point in the upper section of the distillation column, thus it may be drawn off directly in gaseous form via a top draw-off, above the upper plate or internal packing, or via a gaseous or liquid side draw-off below the upper tray or upper level of packing.

In both embodiments, it is preferred that the second gaseous stream comprises 50% by weight or more of EO.

In a further aspect of the present invention, apparatus is provided for the concentration or purification of ethylene oxide from a mixture of ethylene oxide and water, which is a distillation column connected to a microchannel apparatus. Advantageously, the microchannel apparatus is positioned inside the shell of the distillation column at a point above the uppermost distillation tray or packing material.

By incorporating microchannel apparatus inside the distillation column it is possible to provide integral reflux within the column which significantly improves process safety. In a commercial EO production plant, such use, in accordance with present invention, of an integrated microchannel apparatus to cool EO gases within a distillation column allows cooling, by condensation, to occur without the need of an external condensate collection vessel. The presence of stagnant EO is therefore avoided and the likelihood of explosion is minimized.

The operation of the process of the present invention can be described, for example, with reference to FIG. 1 herewith.

The gaseous mixture comprising ethylene oxide, which preferably is a gaseous stream forming the top stream of an EO stripper or of an EO purification column, enters header 102 and is split into multiple portions to progress through the reactor via a plurality of process microchannels 104. Coolant is fed into the apparatus via heat exchange header 110 and flows through the apparatus cross-currently (as shown in FIG. 1) or co- or counter-currently, via heat exchange channels to the footer 112.

When the microchannel apparatus is sited within a distillation column, it is most suitably sited in the centre of the column and may extend across the full diameter of the column, being affixed directly to the column walls, or across the diameter only in part. In the latter case the apparatus may be placed on beams extending from the inner column walls or may be suspended by arms extending from the inner column walls, provided that the beams or arms do not restrict the gas and liquid flow in the column. The height of the microchannel apparatus suitably also is such as to not interfere with the normal operation of the distillation column; and the length of the process microchannels most suitably is in the range of from 5 to 100 cm.

In all cases it is important that gas flow in the distillation column can circulate to the top of the column, either around the outside of the microchannel apparatus or through channels or holes in the apparatus. The microchannel apparatus is so sited that the second gaseous stream enters the apparatus via a header at the top of the apparatus as in FIG. 1. The gaseous stream condenses within the process microchannels and liquid ethylene oxide runs through the process microchannels and collects in an exit header, or other collection unit, at or under the bottom of the apparatus, and can be withdrawn from the column. The condensation causes the gaseous stream automatically to be drawn into the process microchannels. Coolants can be routed into the apparatus and may for example be water or other coolant material that takes up heat created by the condensation.

The general process conditions that may apply for the use of microchannel apparatus in an EO condensation process of the invention are suitably a temperature in the range of from ambient (20° C.) to 100° C., for example 30 to 50° C., and a pressure in the range of from 100 to 1,000 kPa, for example 200 to 400 kPa.

Volatile contaminants are often produced by industrial chemical processes. Such contaminants are often vented to the atmosphere but with increasing environmental legislation, smaller amounts of such contaminants are permitted to be vented from commercial manufacturing plants.

One such area in which contamination in vent or waste gas can occur is in the production of ethylene oxide. The residual gases that remain after recovery of the bulk ethylene oxide product, are recycled to the ethylene oxidation reactor. A side stream, part or all of the recycle gas, is usually scrubbed with an aqueous $CO_2$ absorbent for removal of excess $CO_2$ which is subsequently stripped from the absorbent and may be vented, or preferably is recovered for use or sale as a by-product. A problem arises particularly in manufacturing plants of large capacity in that during scrubbing of the recycle gas side stream, small amounts of hydrocarbon are dissolved and/or entrained in the $CO_2$ absorbent and need to be removed to avoid contamination of the carbon dioxide.

Various systems have been proposed for the removal of volatile contaminants from vent gases. Such contaminants may be organic hydrocarbons, such as ethylene, methane, ethylene oxide, and halogen-containing compounds. Where the contaminant is a volatile organic compound, current removal processes utilize thermal or catalytic decomposition, preferably combustion.

In many industrial processes the vent gases are cleaned of these impurities in an oxidizer by total combustion in a packed bed reactor, either thermally or catalytically if the reactor contains a catalyst. In some instances, such a reactor is combined with a heat exchanger in order to recover the combustion heat generated. Such combustion, or incineration, can for example occur within a catalytic incinerator whereby one or more catalyst beds are heated to high temperatures (in the range of from approximately 300° C. to 800° C.; typically 500° C.) and operate at atmospheric pressure. In the thermal combustion systems the temperatures may be in the range of from 700 to 1000° C. and also operate at atmospheric pressure. Various heat exchange mechanisms are therefore also incorporated to minimize energy loss and improve efficiency.

A more sophisticated system is the reverse flow reactor. Reverse-flow reactors are well known in the art. The general principle of such reactors has been described in detail in "Reverse-Flow Operation in Fixed Bed Catalytic Reactors", Cata. Rev.-Sci. Eng., 28(1), 1-68 (1996).

Reverse-flow reactors have been employed in a number of different large-scale heterogeneous processes, such as catalytic incineration of volatile organic contaminants, the hydrogen sulphide oxidation by sulphur dioxide, Fischer-Tropsch synthesis over ruthenium and cobalt catalysts, the selective reduction of carbon monoxide and/or nitric oxides in flue gases, and similar processes, as described in U.S. Pat. No. 6,261,093, CA-A-1,165,264, U.S. Pat. No. 5,753,197, and U.S. Pat. No. 5,589,142.

A simple reverse-flow reactor for catalytic reactions on a fixed catalyst bed consists of a reactor vessel comprising at least one catalyst bed and optionally, one or more beds of refractory packings, often referred to as inerts to hold the catalyst bed in place which also may provide for additional heat capacity, together with the necessary line-up and switching valves that allow oscillation of the flow direction of a fluid or gaseous reaction medium between the respective reactor in- or out-let.

A reverse-flow reactor has the disadvantage that the system contains switching valves that are subject to mechanical stresses causing mechanical failure.

The present invention utilizes microchannel apparatus to combust volatile contaminants in a vent gas or other gas stream; this is an effective means of removing such contaminants and additionally allows effective heat exchange to occur in the same apparatus as combustion, thereby combining the two processes in one piece of equipment resulting potentially in a lower CAPEX. In particular, against a reverse-flow system, the complex switching mechanism is avoided and the process becomes simpler and more reliable.

Thus, using a microchannel apparatus as an oxidizer is simpler, easier to operate and potentially less expensive than prior proposals. The apparatus will combine a high heat integration with a high efficiency of combustion which is very important to remove low, ppm, amounts of contaminants. In the prior proposals, even with the sophisticated reverse flow reactor, leakage occurs, via the switching valves or through by-pass mechanisms to avoid overheating, which make the systems unreliable. A microchannel apparatus enables heat control via other mechanisms than a separate heat exchanger or by-pass systems, and does not utilize switching valves.

The present invention accordingly provides a process for the removal of combustible volatile contaminant materials from a first process stream, which comprises a) flowing a first process stream through a first set of process microchannels in a microchannel apparatus, b) heating said first process stream to the combustion temperature of the volatile contaminant materials and combusting the volatile materials to form a hot cleaned stream, which may also contain combustion products, c) conducting the hot cleaned stream through heat exchange channels, which may preferably be a second set of process microchannels, which are in thermal contact with said first set of microchannels, and subsequently d) recovering a cooled, cleaned process stream.

The volatile contaminant materials may be any of the following organic hydrocarbons: ethane, ethylene, methane, ethylene oxide, and halogen-containing compounds such as organic chlorides. Such contaminants may be present in an amount in the range of from 0.05 to 1% by weight of the first process stream, for example 0.05 to 0.5% by weight.

The combustion or incineration of the volatile contaminants occurs within a first set of process microchannels within a microchannel apparatus and yields combustion products of water and carbon dioxide. These may be carried with the treated stream out of the microchannel apparatus to be removed with the rest of the gas stream. These heated gases are conducted to a first set of heat exchange channels which are in thermal relationship with said first microchannel set. In this way the heated gases heat the first process stream to combustion temperature. To allow for start-up and for thermal losses that may occur, an additional heating device may be necessary to heat the first process stream at the start of operation of the process, and to ensure the necessary heat to reach combustion temperature within the first set of microchannels. Such an additional heating device can be readily incorporated into the microchannel apparatus by means of a simple burner or as a second set of heat exchange channels, for example. It is expected that the microchannel apparatus will lead to less thermal loss from the hot cleaned stream, and that such ancillary heating means will be less required than in prior proposals.

The first set of heat exchange channels are preferably adjacent to the first set in the form of a second set of microchannels. The two sets of (micro)channels can be so configured as to allow co-current flow, counter-current flow, or cross-current flow for the two process streams. Most preferred is a configuration that establishes counter-current or cross-current flow, and especially counter-current flow. While the apparatus may be set up so that the hot cleaned stream may exit the microchannel apparatus and re-enter in order to be aligned in thermal contact with the first process stream, for reasons of thermal economy it is preferred for the hot cleaned stream to remain in the microchannel apparatus until the heat exchange with the first process stream has occurred. Thus preferably the first process stream will flow through the first set of microchannels and then be led to the first set of heat exchange channels which are positioned adjacent to the full length of the first set of microchannels. The cooled, cleaned process stream in this embodiment will usually exit the apparatus close to the point at which the first process stream enters. The exit of from the microchannel reactor may however be at any suitable point, and may be at the opposite end of the apparatus to the inlet point in certain embodiments.

If the combustion provides excess heat than is needed for the heating of the first process stream, for example because the first process stream is already heated before treatment, or the combustion reaction needs to be controlled thermally, then additionally a second set of heat exchange channels may be present in the microchannel apparatus which can remove excess heat from the combustion reaction, which heat can be used directly, or at another location, for example to produce steam. Said second set of heat exchange channels are preferably also microchannels, and would then form a third set of microchannels. Alternatively, part of the hot gases can be bled off.

It is preferred that such a process be utilized for the removal of volatile organic hydrocarbons from a carbon dioxide process stream, most preferably for the removal of one or more of ethylene, methane, and ethylene oxide. The carbon dioxide stream is preferably a $CO_2$ waste stream from an ethylene oxide production plant. The level of purity achieved means that the cleaned $CO_2$ may be sold as a commercial product.

However, the process of the invention may be utilized in any situation where currently an oxidizer or incinerator is utilized to remove volatile organic impurities, such as to treat any vent gas from a commercial petrochemicals plant or off-gas from a tankfarm; and indeed for the cleaning-up of any gas streams that have from 1 ppm to 10% by volume of volatile organic hydrocarbon impurity.

The microchannel apparatus may be adapted to allow catalytic combustion or incineration of the volatile contaminant materials. As previously mentioned, a catalyst can be incorporated into the process microchannels in a number of suitable ways. The catalyst components most suited to catalytic combustion are well known to those in the art. A suitable catalyst component comprises, as the catalytically effective component, a metal or cationic metal component selected from platinum, palladium, rhodium, rhenium, nickel, cobalt and manganese; a refractory oxide carrier such as alumina may also be present but is not required. The catalyst may be incorporated in solid form as a packing within the microchannels or via a wash-coating onto the walls of one or more of the process microchannels, most suitably of the first set of process microchannels.

The process of the invention is carried out at the conventional temperatures and pressures noted above for thermal and catalytic incinerators.

The thermal conversion of ethylene oxide and water to ethylene glycol is well known and commercially practiced world-wide, see for example the description in Ullmann's Encyclopedia of Industrial Chemistry, Volume A 10, pages 104 & 105. The thermal process requires a high molar excess of water, as much as a 20-fold molar excess, to yield the most desired product of mono-ethylene glycol. Catalytic conversions that are selective to mono-ethylene glycol and that do not require such high excess of water are also of interest. Catalytic processes for converting alkylene oxides directly to alkylene glycols in general have been investigated and catalysts capable of promoting a higher selectivity to monoalkylene glycol product at reduced water levels are known, (e.g. EP-A-015649, EP-A-0160330, WO 95/20559 and U.S. Pat. No. 6,124,508).

All of these conversion reactions are highly exothermic.

The present invention provides a process for the preparation of an alkylene glycol by the reaction of a corresponding alkylene oxide and water, which process comprises a) flowing the alkylene oxide and water through a microchannel reactor, wherein the oxide and water undergo an exothermic reaction to form the corresponding alkylene glycol, b) transferring heat from the microchannel reactor to a heat transfer medium, and c) recovering the alkylene glycol product from the microchannel reactor.

Utilizing a microchannel reactor provides the advantages of a high removal rate of the heat of reaction, and a much greater temperature control of the full conversion process.

The microchannel reactor can also incorporate a catalyst system that permits the reduction of the high water excess. Such a catalyst system may be a homogeneous catalyst that is mixed with the reactants either before entry to the reactor or within the reactor, or it may be a heterogeneous system present as a solid catalyst or as a coating, preferably a washcoating, on the walls of one or more, and desirably all, of the process microchannels present in the reactor.

Catalysts that may be employed in the present process are known in the art. Suitable catalysts are acid catalysts and basic catalysts.

Homogeneous catalysts include acidic catalysts which are liquid under the conditions of the reaction. Suitably such catalysts are mineral acids, such as sulphuric acid and phosphoric acid, and such catalysts as known from JP-A-56-092228. Homogeneous metalate catalysts are also very suitable; such catalysts comprise a salt selected from vanadates, molybdates and tungstates. Suitable examples are described in U.S. Pat. No. 4,551,566, EP-A-156447, and EP-A-156448.

Less preferred are heterogeneous catalysts. Ones that may be mentioned are acidic catalysts such as strongly acidic ion exchange resins, such as those comprising sulphonic acid groups on a styrene/divinylbenzene copolymer matrix, and silicas and oxides of metals selected from Groups 3 to 6 of the Periodic Table of Elements, for example zirconium oxide and titanium oxide. As basic catalysts there may be mentioned those comprising an ion exchange resin (IER) as a solid support, in particular the strongly basic (anionic) IER's wherein the basic groups are quaternary ammonium or quaternary phosphonium on a styrene/divinylbenzene copolymer matrix. Also suitable as heterogeneous catalysts are metalates, such as vanadates, molybdates and tungstates, contained on a solid support such as an ion exchange resin or a hydrotalcite clay as described in EP-A-156449 and EP-A-318099.

Suitable ion exchange resins utilized may be based on vinylpyridine, polysiloxanes. Other solid supports having electropositive complexing sites of an inorganic nature may also be utilized, such as carbon, silica, silica-alumina, zeolites, glass and clays such as hydrotalcite. Further, immobilized complexing macrocycles such as crown ethers, etc. can be used as well as a solid support.

Such heterogeneous catalyst may be based on a strongly basic quaternary ammonium resin or a quaternary phosphonium resin, for example an anion exchange resin comprising a trimethylbenzyl ammonium group. Examples of commercially available anion exchange resins on which the catalyst may be based include LEWATIT M 500 WS (LEWATIT is a trademark), DUOLITE A 368 (DUOLITE is a trademark) and AMBERJET 4200 (AMBERJET is a trademark), DOWEX MSA-1 (DOWEX is a trademark), MARATHON-A and MARATHON-MSA (MARATHON is a trademark) (all based on polystyrene resins, cross-linked with divinyl benzene) and Reillex HPQ (based on a polyvinylpyridine resin, cross-linked with divinyl benzene).

The anion exchange resin in the fixed bed of solid catalyst may comprise more than one anion which may be selected from the group of bicarbonate, bisulfite, metalate and carboxylate anions.

When the anion is a carboxylate anion, it may be a polycarboxylic acid anion having in its chain molecule one or more carboxyl groups and one or more carboxylate groups, the individual carboxyl and/or carboxylate groups being separated from each other in the chain molecule by a separating group consisting of at least one atom. The polycarboxylic acid anion is suitably a citric acid derivative, more preferably a mono-anion of citric acid.

A suitable solid catalyst is a catalyst based on a quaternary ammonium resin, preferably a resin comprising a trimethylbenzyl ammonium group, and wherein the anion is a bicarbonate anion.

The alkylene oxides used as starting materials in the process of the present invention, have their conventional definition, i.e. they are compounds having a vicinal oxide (epoxy) group in their molecules.

Preferred alkylene oxides are alkylene oxides of the general formula:—

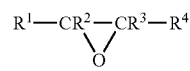

wherein each of $R^1$ to $R^4$ independently represents a hydrogen atom or an optionally substituted alkyl group having from 1 to 6 carbon atoms. Any alkyl group, represented by $R^1$, $R^2$, $R^3$ and/or $R^4$, preferably has from 1 to 3 carbon atoms. Optional substituents on the alkyl groups include hydroxy groups. Preferably, $R^1$, $R^2$, and $R^3$ represent hydrogen atoms and $R^4$ represents a non-substituted $C_1$-$C_3$-alkyl group and, more preferably, $R^1$, $R^2$, $R^3$ and $R^4$ all represent hydrogen atoms.

Examples of alkylene oxides which may conveniently be employed include ethylene oxide, propylene oxide, 1,2-epoxybutane, 2,3-epoxybutane and glycidol. The alkylene oxide is preferably ethylene oxide or propylene oxide; ethylene glycol and propylene glycol being alkylene glycols of particular commercial importance. Most preferably the alkylene oxide of the present invention is ethylene oxide or propylene oxide and the alkylene glycol is ethylene glycol or propylene glycol.

When the conversion is a thermal conversion, the temperature may be in the range of from 100 to 300° C., in particular from 150 to 250° C. When the conversion is a catalytic conversion, the temperature may be in the range of from 30 to 200° C., in particular from 50 to 150° c. The molar ratio of water to the alkylene oxide may be in the range of from 5 to 50, in particular from 10 to 30. The pressure may be in the range of from 500 to 3500 kPa, as measured at the second feed channel, described hereinbefore.

In certain embodiments of the present invention it may be beneficial to add carbon dioxide to the (catalytic) reactor to establish advantageous conditions for the hydrolysis. Such carbon dioxide may conveniently be added directly to the reactor or it may be added to the alkylene oxide feed. If carbon dioxide is to be added, the amount of carbon dioxide added may be varied to obtain optimum performance in relation to other reaction parameters, in particular the type of catalyst employed. However the amount added will preferably be less than 0.1% wt, more preferably less than 0.01% wt, based on a total amount of reactants in the second reactor.

With reference to FIG. 2, as an example, alkylene oxide may be fed into first section 240 via feed channels 260 and/or 220, and water may be co-fed through the same channels or fed into the microchannel system via feed channel 360 of second section 340. In a specific embodiment when the oxide is fed through channel 240, then, water may be fed through channels 220 and mixed with the oxide in the microchannels. To remove heat evolved during the reaction, coolant may flow via heat exchange channels 250 and/or 350 depending on the site of reaction and the channel through which the water feed is fed. If alkylene oxide and water are co-fed to the first section, then where catalyst is present, any additional component useful for the reaction, such as carbon dioxide, may be fed to the reactants via the second section 340.

The use of a microchannel reactor permits a greater control of the exothermic reaction than has hitherto been possible which reduces the need for excess volumes of water to act as a heat sink.

The hydration of ethylene oxide to mono-ethylene glycol (MEG) is normally carried out in the liquid phase in, for example, a pipe or tube reactor. As noted above previously proposals to use catalysts in such conversions have been made. Additionally it has been proposed to react EO and water in the vapor phase since this can be beneficial in terms of process integration and separation. Regarding the latter in particular the removal of MEG from a gas stream is possibly easier than from a dilute aqueous stream as in conventional plants.

Heterogeneous hydrolysis catalysts can also be utilized in vapor phase hydration, where mono-ethylene glycol will be formed as the main product. However inevitably the EO present will also react with the formed glycols to form higher molecular weight glycols, for example EO with mono-ethylene glycol will form di-ethylene glycol, with di-ethylene glycol EO will form tri-ethylene glycol, and so forth. The major problem with the use of heterogeneous catalysts for vapor phase reactions is that the higher glycols have a high boiling point and thus are liquid at the typical reaction temperature and pressure applied. Thus the catalyst surface will be covered with glycols quickly growing in molecular weight leading to deactivation of the catalyst. MEG may also be trapped as liquid on the catalyst surface. Also the reaction of EO with glycols on the surface of the catalyst will result in a reduced selectivity of EO to mono-ethylene glycol product.

The use of certain highly selective heterogeneous catalysts in the vapor phase hydration of ethylene oxide has been proposed in the literature, most recently in EP-A-318099 and EP-A-529726 which describe the use of specific hydrotalcites, which are anionic clays, both for vapor and liquid phase hydration.

However even with a high degree of selectivity to mono-ethylene glycol, the problem of deactivation by deposition of other glycols produced as by-products in vapor phase hydration will still exist.

In the present invention it is proposed to operate a gas phase reactor in a 'swing' mode. In mode 1, the reaction mode, the temperature and pressure are optimized to achieve the desired production of mono-ethylene glycol. A heterogeneous catalyst which is highly selective to the production of MEG is preferably used. Preferably the temperature is maintained in the range of from 200 to 350° C., most suitably 200 to 275° C., and the pressure in the range of from 100 to 1000 kPa. Suitably this process is performed without excessive amounts of water. The amount of water is preferably in the range of from 1 to 35 moles per mole of alkylene oxide, more preferably from 1 to 20 moles, most preferably from 1 to 10 moles, per mole of alkylene oxide.

The heterogeneous catalysts preferred for use in such a process are based on support materials selected from members of the family of clays; aluminas, for example α- and γ-alumina; zirconias; silicas; and hydrotalcites (anionic clays).

Such support materials suitably have a metal component, for example a metal ion or a metal oxide deposited thereon to enhance activity and/or selectivity, but can be utilized above. Any metal or metal component can be incorporated into the catalyst. Most suitably such a metal component may be selected from one or more metals of Groups IA, IIA, IIIA, IVA, VA, VIA, VIIA, VIIIA, IB, IIB, and IIIB of the Periodic Table (using the IUPAC notation). Very suitable metals include sodium, cesium, molybdenum, nickel, cobalt, zinc, aluminum, lanthanum, rhenium, tungsten, and vanadium.

Suitable catalyst components may also include anionic groups such as hydroxide ions, carbonate ions, sulphate ions and phosphate ions.

Where the support material is a hydrotalcite, such materials are anionic clays and consist of positively charged layers of oxides and/or hydroxides, for example in conjunction with a mixture of $Mg^{2+}$ and $Al^{3+}$ cations, separated by a layer containing water and charge compensating anions, for examples hydroxides or carbonates.

Examples of suitable catalyst systems are:

$MoO_4/ZrO_x(OH)_{4-2x}$; $Cs/α-Al_2O_3$; $Co/Mo/α-Al_2O_3$; $Zn/Al/CO_3$ hydrotalcite; $Co/Mo/SiO_2$; $Mo/Co/Zn/Al$ hydrotalcite; hydrotalcite/Na-citrate; $Co/Zn/Al$-hydrotalcite; Mo—Co/Zn/Al-hydrotalcite; $SiO_2$ granules; 12 wt % $La/α-Al_2O_3$; $SO_4/ZrO_x(OH)_{4-2x}$; $SO_4/ZrO_2$; $ZrO_x(OH)_{4-2x}$; $ZrO_2$; $PO_4/ZrO_x(OH)_{4-2x}$; $PO_4/ZrO_2$; $ReO_4/ZrO_x(OH)_{4-2x}$; $ReO_4/ZrO_2$; $WO_4/ZrO_x(OH)_{4-2x}$; $WO_4/ZrO_2$; $MoO_4/ZrO_x(OH)_{4-2x}$; $MoO_4/ZrO_2$; Ni/V hydrotalcite; Ni/V hydrotalcite-coated Al/5Mg; $α-Al_2O_3$; $Co/α-Al_2O_3$ dried; $Co/α-Al_2O_3$ calcined; $Cs/α-Al_2O_3$ dried; $Cs/α-Al_2O_3$ calcined; $Co/Mo/α-Al_2O_3$ dried; $Co/Mo/α-Al_2O_3$ calcined; $ZnAlCO_3$ hydrotalcite; and $CoMoSiO_2$. In the preceding list x, where it appears, is a number from 0 to 2.

Such catalysts are either available commercially or may be easily prepared by techniques well known to the person skilled in the art.

Hydrotalcite-type catalysts of the type proposed in EP-A-529726 are very suitable. These are hydrotalcite-type catalysts of the general formula

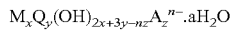

wherein M is at least one divalent metal cation; Q is at least one trivalent metal cation; A is at least one component having a valence n-selected from a metalate anion, selected from vanadate (suitably metavanadate, orthovanadate, pyrovanadate, and hydrogen pyrovanadate), tungstate, niobate, tantalite and perrhenate, and a large organic anion spacer; and a is a positive number. M, Q and A are present such that $x/y$ is greater than or equal to 1, $z>0$, and $2x+3y-nz$ is a positive number. The composition has a layered structure where A is located in anionic sites of the composition.

In catalysts of the above general formula in which A is a large organic anion spacer, the selectivity to MEG is increased. Therefore preferably A is a large organic spacer and may be any organic acid containing from one to 20 carbon atoms, provided its steric bulk is large. Such organic acid or its alkali salt must be somewhat soluble in a solvent, and may have one or more carboxylic acid functional groups, and may have one or more sulphonic acid functional groups. Large organic anion spacers containing carboxylic acid functional groups are preferred, since these functional groups are readily removed by heating. Preferred large organic anion spacers include terephthalate, benzoate, cyclohexanecarboxylate, sebacate, glutarate and acetate. Preferably, the large organic anion spacer is selected from the group consisting of terephthalate and benzoate. Terephthalate is the most preferred large organic anion spacer. Mixtures of large organic anion spacers may also be used.

Preferably $x/y$ is in the range of from 1 to 12, more preferably 1 to 6, and most preferably 1 to 4.

Suitable divalent cations M broadly include elements selected from the transition elements and Groups IIA, IVA and VA of the Periodic Table (IUPAC version), as well as certain rare earth elements. Specific examples of divalent metal cations are magnesium, calcium, titanium, vanadium, chromium, manganese, iron, cobalt, nickel, palladium, platinum, copper, zinc, cadmium, mercury, tin, lead and mixtures thereof. Divalent metal cations which are particularly suitable are magnesium, nickel, cobalt, zinc, calcium, iron, titanium and copper.

Suitable trivalent metal cations Q broadly include elements selected from the transition elements and Groups IIIA and VA of the Periodic Table as well as certain rare earth elements and actinide elements. Specific examples of trivalent metal cations are aluminum, antimony, titanium, scandium, bismuth, vanadium, yttrium, chromium, iron, manganese, cobalt, ruthenium, nickel, gold, gallium, thallium, cerium, lanthanum and mixtures thereof. Trivalent metal cations which are particularly suitable are aluminum, iron, chromium, and lanthanum.

The foregoing lists of suitable divalent and trivalent metal cations are meant to be illustrative but not exclusive. Those skilled in the art will recognize that other cations can be used, provided that the types of cations and relative amounts ($x/y$ ratio) result in a hydrotalcite-type catalyst, M is nickel, Q is aluminum, E is metavanadate and $x/y$ is in the range of 1 to 6. Another preferred hydrotalcite-type catalyst is formed when M is nickel, Q is aluminum, E is niobate and $x/y$ is in the range of 1 to 6. Hydrotalcite-type materials in which M is nickel and Q is aluminum are known as takovites.

Such hydrotalcite catalysts may be prepared by the procedures described in EP-A-529726.

The reactor is changed to mode 2 (step b) once glycols form on the surface of the catalyst. This can be after reaction time of from 1 second to 10 hours, preferably from 10 seconds to 1 hour, depending on the reaction conditions (temperature and pressure). In mode 2, the desorption or evaporation mode, the temperature, the pressure, or both temperature and pressure, are adjusted to desorb or evaporate the glycols from the surface of the catalyst, while the gas stream is fed to a second reactor. Essentially the temperature has to be increased and/or the pressure decreased to such conditions as are necessary to cause the glycols to desorb and/or to evaporate. Preferably if temperature alone is altered then the temperature is changed to be in the range of from 250 to 400° C. If the pressure alone is altered then the pressure is preferably changed to be in the range of from 1 Pa to 500 kPa. If both temperature and pressure conditions are altered, then the conditions are preferably changed to a temperature in the range of from 300 to 350° C. and a pressure in the range of from 1 Pa to 300 kPa. The rate of change of the temperature and pressure conditions can be optimized to achieve maximum economical benefit.

It may be beneficial also to utilize a sweep gas in mode 2. Such a gas may be introduced into the reactor, when in mode 2, in order to sweep or carry the desorbed glycol(s) out of the reactor and onto a separation section or unit. Suitably such a sweep gas would be an inert gas, such as steam or preferably nitrogen.

The product MEG may be deposited on the catalyst surface with the other glycols or preferably remains in the vapor phase. Where the MEG is predominantly produced and maintained in the vapor phase, the reactor mode switching is still necessary to prevent deactivation of the catalyst by the higher glycols deposited thereon.

The vapor phase mixture of unconverted EO and water and mono-ethylene glycol product coming out of the reactor zone that is operated in mode 1, is suitably led through a downstream zone that is operated at a lower temperature and/or higher pressure, where the mono-ethylene glycol can be separated from the gaseous mixture by condensation. If desired, a water/mono-ethylene glycol mixture can be separated by condensation from the vapor phase by further lowering the temperature or by further increasing the pressure. This separation or condensation zone may also be operated in a 'swing' mode. After having condensed mono-ethylene glycol or mono-ethylene glycol and a part of the water from the reactor product vapor stream, this stream may be directed to a second, similar separator or condensation zone. The condensed product is removed from the first zone. During the removal, the temperature or pressure of the separation zone may, or may not, be changed from the conditions during condensation. Where MEG is trapped on the catalyst surface, then it may similarly be recovered from the vapor mixture produced in mode 2 by evaporation.

Quick changes in temperature are possible but somewhat difficult in the conventional large vapor phase reactors that are normally used in the process industry, particularly those utilizing heterogeneous catalyst, because of the large gas and catalyst volumes, large heat transfer medium volumes, the steel mass (heat sink) and heat transfer limitations. Therefore the reaction, as well as the separation, is advantageously performed in the process microchannels of one or more microchannel reactors, which enables fast and accurate temperature plus pressure change and control. The downstream condensation zone(s) may also advantageously be one or more process microchannels of one or more further microchannel apparatus.

The present invention accordingly provides a process for the preparation of a mono-alkylene glycol by the reaction of a corresponding alkylene oxide and water, which process comprises a) reacting the alkylene oxide and water in a first reactor under a first set of conditions and in the presence of a catalyst so as to achieve vapor phase conversion to the mono-alkylene glycol,
b) altering the conditions in the first reactor to a second set of conditions whereby glycols deposited on the surface of the catalyst are removed,
c) re-establishing the first set of conditions in the first reactor in order to repeat step a), and
d) recovering the mono-alkylene glycol from a vapor phase mixture produced in step a) and/or step b).

In a preferred embodiment the process is operated using two reactors whereby simultaneously with operating step b), the gaseous alkylene oxide and water feeds are switched to a second reactor which is operating under the first set of conditions. When the first set of conditions are re-established in the first reactor under step c) of the process of the invention, the feeds are switched back to the first reactor and the conditions of the second reactor are changed to the second set of conditions.

The vapor product stream from the first reactor thus comprises the mono-alkylene glycol and possibly heavier components, the latter may be for example di- and tri-ethylene glycol. However, because of the preferential deposition of the heavier glycols onto the surface of the catalyst in the first reactor, the amount of these 'heavies' in the product stream of step a) will be low. Greater amounts of heavier glycols may be present in the product mixture from step b). In both cases the heavier glycols where present can optionally be removed via a distillation column (a 'topping and tailing column') where the pure mono-ethylene glycol is withdrawn as a side-stream and these heavies are drawn off as a separate stream and utilized, or incinerated as waste.

The nature of the two sets of conditions may vary, however generally the conditions will be such that a direct change from the first set of conditions to the second set of conditions will cause the evaporation of glycol deposited on the catalyst.

Most preferably the first reactor, and second reactor where present, is a microchannel apparatus such as described herein. This provides the additional advantage of good control of the conditions to be changed. The first reactor may be in a first set of process microchannels operating under the first set of conditions, and then the conditions can be changed by use of a heat transfer medium, flowing through heat exchange channels, to change, for example, the temperature conditions to provide evaporation of the glycol. Two microchannel apparatus may be provided working in tandem with the glycol-containing feed being switched between the two microchannel apparatus so that a continuous operation can occur, with a first microchannel performing the vapor phase hydration while the second is in evaporation mode, and then switching the feed so that the second apparatus performs the reaction while the first performs the evaporation.

Reference is made to the publications U.S. Pat. No. 6,508,862 and WO 2005/032693 which describe microchannel apparatus used in temperature swing sorption for fluids. The apparatus and control mechanisms may be readily adapted to operating the process of the present invention by those skilled in the art.

This aspect of the process of the invention may additionally be utilized in conjunction with the use of microchannel apparatus to perform conversion of alkylene oxide to glycol as described above.

The present invention will now be illustrated by the following Examples.

EXAMPLES

Example 1

This prophetic example describes how an embodiment of this invention may be practiced.

In a 400,000 mt/a ethylene oxide plant the stream of recycle gas to the reactor system is 600 mt/h. This flow mainly consists of methane, ethylene, oxygen, argon, carbon dioxide and nitrogen. The temperature at the reactor inlet is 140° C. and the pressure is 2000 kPa gauge.

Figure 3:
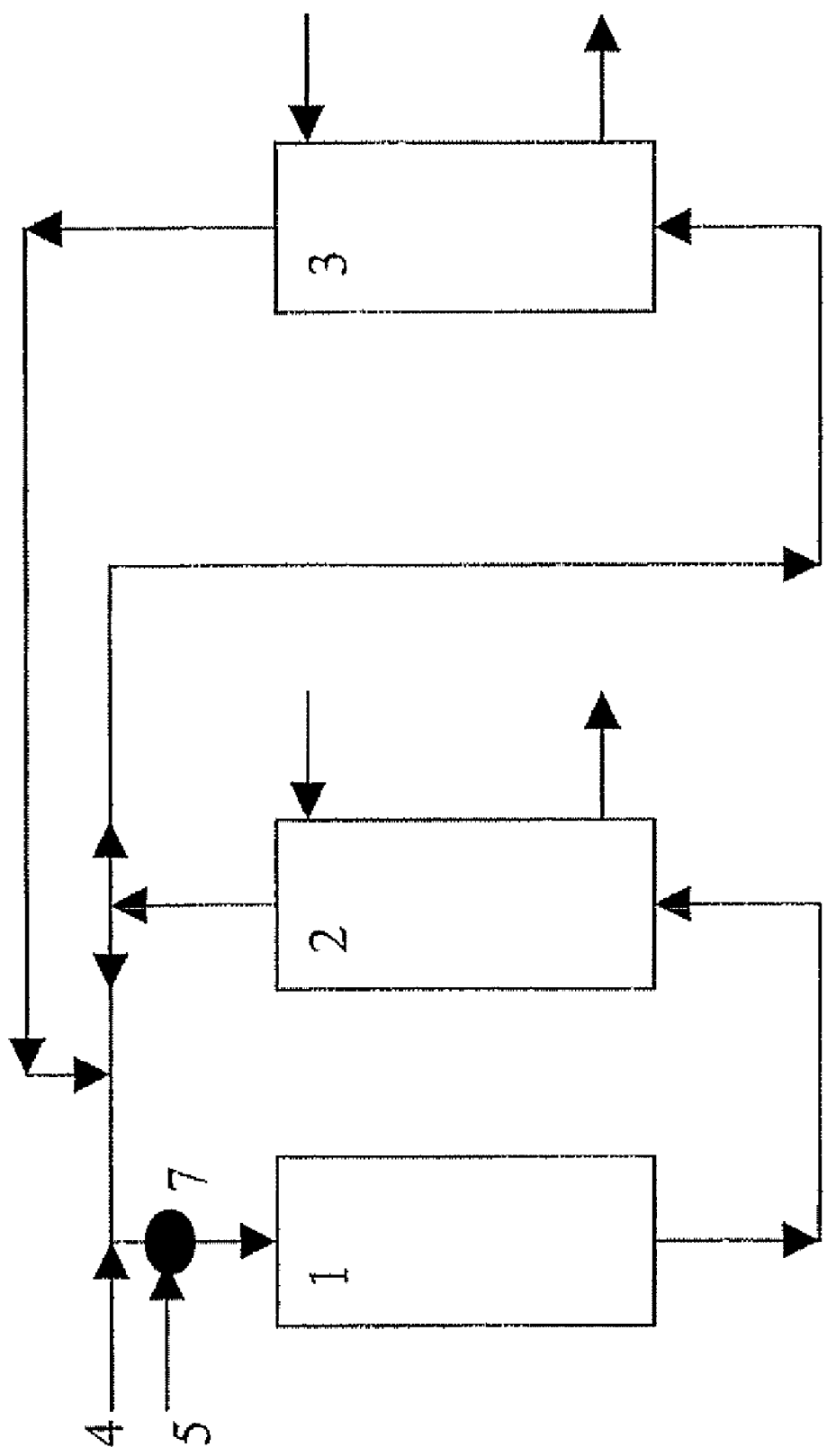
FIG. 3 shows a schematic drawing of an example of a process for the preparation of ethylene oxide according to the invention.

In FIG. 3, over the catalyst inside the reactor 1, ethylene and oxygen are consumed in the production of ethylene oxide (EO) and carbon dioxide ($CO_2$). After scrubbing the reaction product gases with water to absorb EO in EO absorber 2, and scrubbing part of the recycle gas of $CO_2$ in $CO_2$ absorber 3, feed ethylene, via line 4, and oxygen, via line 5, are supplied to the recycle gas before entering the reactor 1. 37.5 mt/h ethylene is fed to the recycle gas and 34.6 mt/h oxygen. From reactor 1 through absorber 2 and absorber 3 and back to the reactor 1, all of these sections plus the interconnecting pipework form the recycle gas loop.

The oxygen is mixed with the recycle gas in mixer 7. Mixer 7 is a microchannel device such as described herein with respect to FIG. 1 and FIG. 2. The microchannel devise ensures improved mixing of oxygen with recycle gas through multiple small volumes of gas being mixed in the individual microchannels reducing the impact of an explosion reaction. Explosions in such large volumes of flammable gases in a worldscale EO production facility have a huge impact and by use of the microchannel device in such a plant, the risk of an incident is decreased.

Example 2

This prophetic example describes how an embodiment of this invention may be practiced.

Figure 4:
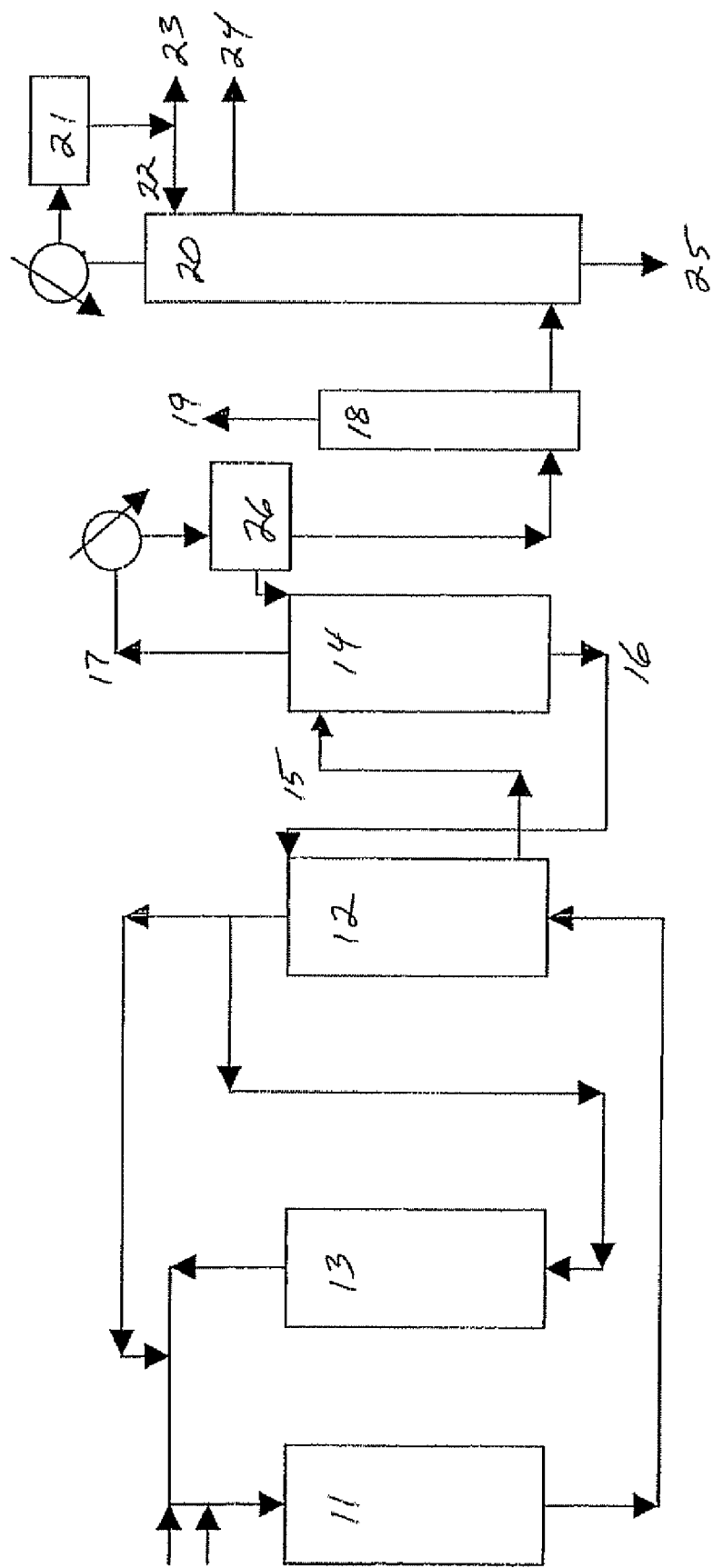
FIG. 4 shows a schematic drawing of an example of a process for the purification of ethylene oxide.

In a 400,000 mt/a ethylene oxide plant the stream of recycle gas to the reactor system is 600 mt/h. This flow mainly consists of methane, ethylene, oxygen, argon, carbon dioxide and nitrogen. The temperature at the reactor inlet is 140° C. and the pressure is 2000 kPa gauge. In FIG. 4, over the catalyst inside the reactor 11, ethylene oxide and carbon dioxide are produced. EO is scrubbed in the EO absorber 12 and part of the recycle gas is scrubbed of $CO_2$ in the $CO_2$ absorber 13. The absorbent used for EO scrubbing is typically water with a small concentration of monoethylene glycol (2-10 weight %). Water saturated with ethylene oxide via line 15 from the bottom of the EO absorber 12 is fed to the top of EO stripper 14. The bottoms flow, line 16, of EO stripper 14 is virtually free of EO and recycled back to the top of EO absorber 13. An ethylene oxide-water mixture (typically containing 50 to almost 100 weight % ethylene oxide) is boiled over the top of the EO stripper as a vapor flow, shown by line 17, and is condensed into vessel 26. Optionally part of the condensed vapor can be refluxed to increase the EO concentration in the top of the EO stripper. Gases like methane, $CO_2$ and ethylene are removed, via line 19, from the condensed water/ethylene oxide mixture in a light ends column 18. For pure EO applications the EO is dehydrated and purified in EO purification column 20. Water or a mixture of water and EO leaves the bottom of this column via line 25. The top vapor is condensed and largely refluxed and re-enters the column via line 22 from condensate collection/reflux vessel 21. Typically a small EO flow is fed from the EO reflux vessel 21 to the glycol section as a bleed for light components (see line 23). The pure EO product flow (line 24) is taken from the top section of this column, in this example a few trays below the reflux tray.

In this example the top of the EO stripper 14, the top stripper condensers, EO/water line 25, the light ends column 18, the top section of the EO purification column 20, and the EO reflux vessel 21 contain a high concentration of EO. To limit explosion hazard both EO condensers are microchannel apparatus such as described with respect to FIG. 1 and FIG. 2. They act as condensers according to the present invention. In the apparatus the total EO volume is divided into a large amount of small volumes inside the microchannels. In addition to that, heat transfer is drastically increased, thus minimizing the risk of runaway reactions eventually leading to explosions. In this example the microchannel condensers can optionally be integrated inside the EO stripper 14 and EO purification column 20 as a so-called cold finger enabling internal reflux. Thus a large volume of EO in a reflux vessel is avoided and explosion risk is even further reduced.

Example 3

This prophetic example describes how an embodiment of this invention may be practiced.

Figure 5:
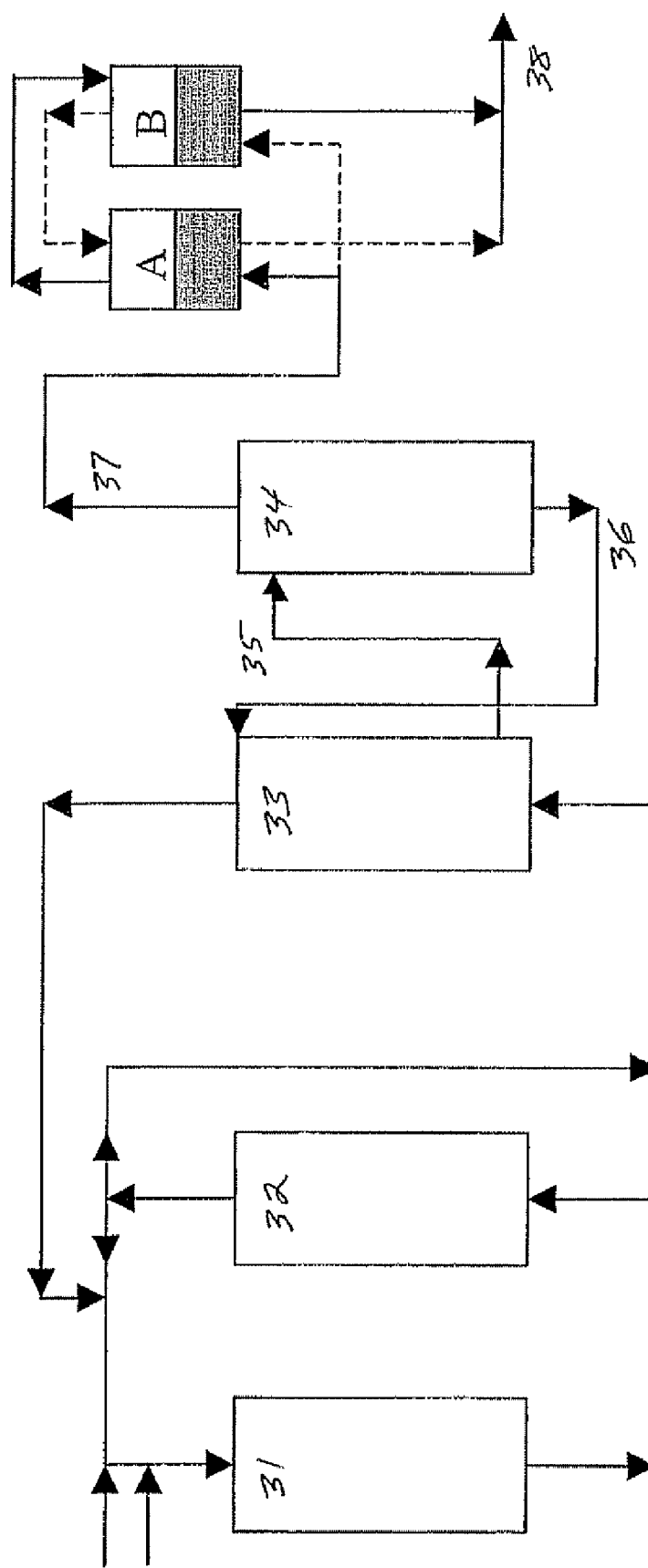
FIG. 5 shows a schematic drawing of an example of a typical process for the removal of combustible volatile contaminant materials from a process stream.

In a 400,000 mt/a ethylene oxide plant the stream of cycle gas to the reactor system is 600 mt/h. This flow mainly consists of methane, ethylene, oxygen, argon, carbon dioxide and nitrogen. The temperature at the reactor inlet is 140° C. and the pressure is 2000 kPa gauge. In FIG. 5, over the catalyst inside the reactor 31, ethylene oxide and carbon dioxide are produced. EO is scrubbed in the EO absorber 32 and part of the recycle gas is scrubbed of $CO_2$ in the $CO_2$ absorber 33.

The absorbent used for $CO_2$ scrubbing is typically a cycling activated hot carbonate solution. Absorbent saturated with $CO_2$ from the bottom of the absorber 33 is fed via line 35 to the top of $CO_2$ stripper 34. Here $CO_2$ is vented to atmosphere as a waste gas flow 37. On average this $CO_2$ waste gasflow is 18 mt/h in this example. The bottoms flow 36 of the $CO_2$ stripper 34 is lean in $CO_2$ and cycled back to the top of absorber 33. The vented $CO_2$ gasflow 37 can contain traces of hydrocarbons like ethylene and methane, in this example 0.1 weight % ethylene and 0.2 weight % methane. Also traces of ethylene oxide can sometimes be detected in this gas stream, although much lower in concentration than previously mentioned hydrocarbons.

Nowadays more and more countries demand lower levels of hydrocarbon emissions and ethylene oxide emissions. Therefore the $CO_2$ waste gas stream is often given a post treatment to remove these components below the level mentioned in the environmental permit. Commonly used technology in this field is oxidizing, in other words combustion, of the hydrocarbons in an oxidizer. This can be either a thermal or a catalytic oxidation process. In order to maintain a proper heat balance these oxidizers are often operated in cycling mode. The system shown in the schematic diagram below is of such a reverse flow system. The gas flows subsequently through two compartments A and B (filled line). Both compartments have a preheat zone and a combustion zone. The hydrocarbons in the $CO_2$ flow are preheated and combusted in compartment A. The preheat zone in compartment A will thus cool down. The hot gas heats up the preheat zone in compartment B to a temperature that allows combustion. As soon as the desired temperature is reached in compartment B, the direction of the gasflow is switched and flows through B and A in the opposite direction (dotted line), and the reverse process takes place.

The clean $CO_2$ gas flow 38 is vented to atmosphere or can be used for other applications. In such a cycling system the switching valves are subject to mechanical stresses and are sensitive to mechanical or even chemical (corrosion) failure. Since the plant has to comply with the environmental permits, the total EO unit has to be shut down in case of failure of the oxidizer, which has a huge economical impact.

In the present invention the two compartments A and B are replaced by a single microchannel apparatus having a first set of process microchannels to receive the $CO_2$ waste gas stream and in which the gas stream is subjected to combustion temperatures in order to combust the volatile hydrocarbon contaminants. The gas stream then flows into a second set of process microchannels which are in thermal contact with the first set and the hot outlet gas can directly heat up the cold gas fed to the combustion chamber. Thus switching is avoided and reliability and simplicity of the system is drastically increased.

Example 4

This prophetic example describes how an embodiment of this invention may be practiced.

Figure 6:
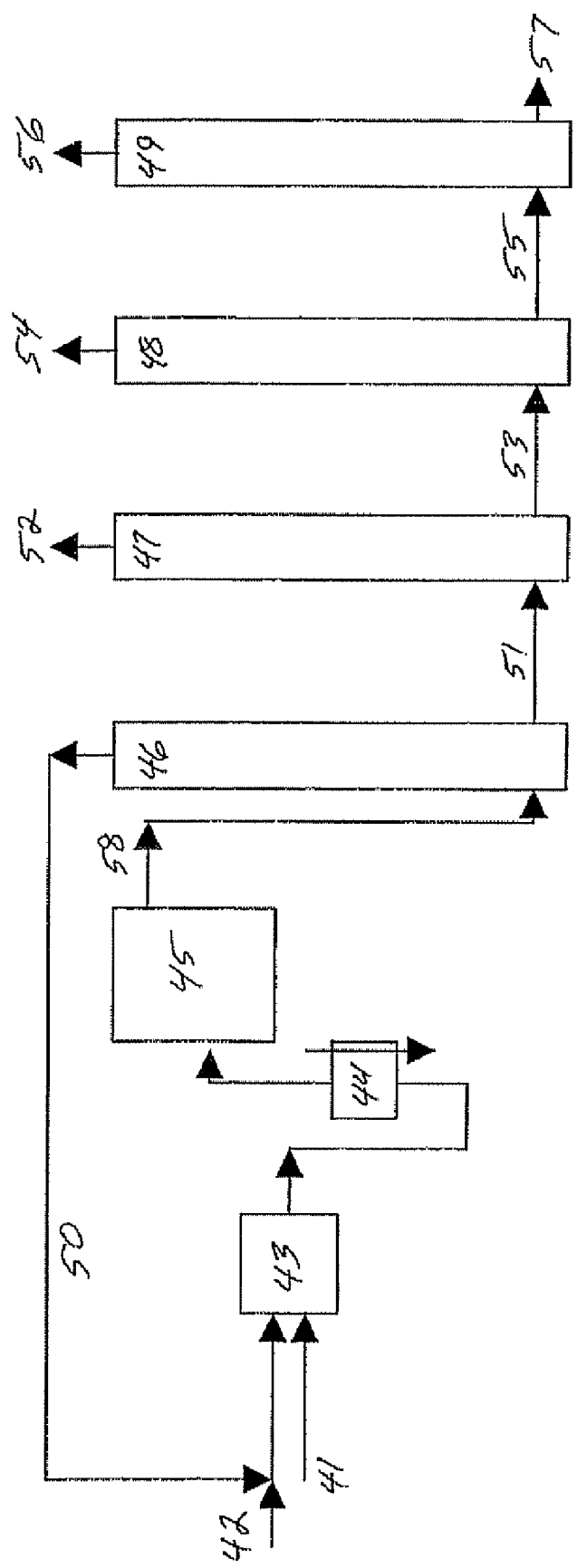
FIG. 6 shows a schematic drawing of an example of a glycol production unit.

In a plant 400,000 mt/a ethylene oxide is produced in a combined EO and glycols plant. 200,000 mt/a of this ethylene oxide is fed to the integrated glycol production unit. In FIG. 6 of such a glycol production unit, ethylene oxide via line 41 is subsequently mixed with fresh water (fed via line 42) and recycle water (50) in vessel 43, preheated in heat exchangers 44, and is reacted without catalysis with water to form monoethylene glycol in reactor 45. Since EO not only reacts with water to mono-ethylene glycol but simultaneously with glycols, not only mono-ethylene glycol is formed but also the byproducts di-ethylene glycol, tri-ethylene glycol and even higher glycols are formed. The amount and ratio of these glycols is heavily determined by the concentration of these glycols inside the reactor. High concentration of water favors a high yield of mono-ethylene glycol. On the other hand at a low concentration of water a lot of di-ethylene glycol, triethylene glycol and the heavier glycols are formed which is in most cases undesired. In this example, the water to EO ratio of the reactor feed is adjusted to be 10:1 to achieve a ratio of 10:1:0.1 mono-ethylene glycol: di-ethylene glycol:tri-ethylene glycol in the reactor outlet stream 58.

The water is not only used as feedstock to form glycols and as dilution agent to control the ratio of glycols, but also acts as a heat sink to control the outlet temperature of the reactor outlet stream, since the reactions in the glycol reactor are strongly exothermic. Since the product glycol is produced in an abundance of water the mixture needs to be dehydrated before separation and purification of the glycol mixture can be achieved. Dehydration is typically carried out in a train of concentrator and dehydrator columns 46. The water streams from the top of these columns are combined as recycle water (50) and recycled to the reactor feed. The water-free bottom stream 51 of dehydrator 46 is fed to the glycol purification section formed by mono-ethylene glycol column 47, di-ethylene glycol column 48 and tri-ethylene glycol column 49, and the glycol mixture is separated into its four product steams mono-ethylene glycol (52), di-ethylene glycol (54), tri-ethylene glycol (56) and heavier glycols (57), with intermediate bottoms streams 53 and 55.

It is evident that the need for large quantities of water will lead to a lot of equipment needed for dehydration, and the dehydration itself will demand a lot of energy use in the form of steam used in the concentrator and dehydrator column reboilers. By making use of the present invention, the reaction of EO to mono-ethylene glycol is performed inside the process microchannels of a microchannel reactor. The temperature can be easily controlled because of the excellent heat transfer, and a large amount of water for heat sink is not needed anymore. The reaction to MEG can be catalyzed to suppress the formation of di-ethylene glycol, tri-ethylene glycol and other heavy glycols. A catalyst may be present in one or more process microchannels. Thus the number of dehydrator columns can be reduced and energy for dehydration can be saved. By using a catalyst the selectivity to mono-ethylene glycol can additionally be increased, enabling reduction of the size of glycol purification equipment.

Example 5

A Co/Zn/Al hydrotalcite-type catalyst was prepared as follows: 24 g of $Co(NO_3)_2.6H_2O$ was dissolved in 200 ml demi-water, 93.8 g of $Al(NO_3)_3.9H_2O$ was dissolved in 300 ml demi-water and 124.2 g of $Zn(NO_3)_2.6H_2O$ in 300 ml demiwater. These three solutions were mixed forming solution A and stored in a drip-flask. Then 70 g NaOH was dissolved in 200 ml demi-water and 53 g $Na_2CO_3$ in 250 ml demiwater. The latter was heated to 50° C. until clear. Both Na solutions were subsequently mixed in a 2 liter round bottom and stirred for 0.5 hour while cooling to <5° C. This is solution B. In the next step solution A was added slowly (ca. 8 ml/min totaling 1.5 hours) to B while keeping the temperature below 5° C. A thick pink gel was formed. After mixing of A and B the resulting slurry was heated to 60° C. and stirred for another 1.5 hours. Then the heater was turned off and stirring was continued for the night. The next day the slurry was filtered and washed 3 times with demi-water. Half of the filter cake was dried at 120° C., the other half was calcined at 425° C. for 12 hrs in air. The target composition was $CO_2Zn_{10}Al_6.(CO_3)_x.yH_2O$ Example 6

This prophetic example describes how an embodiment of this invention may be practiced.

The microchannel reactor will be assembled in accordance with methods known from WO-A-2004/099113, and references cited therein.

A microchannel reactor will comprise process microchannels, heat exchange microchannels, and feed channels.

The process microchannel section will comprise a hydrolysis catalyst comprising cobalt, zinc and alumina as described above.

The process microchannel reactor will be filled with a hydrolysis catalyst that will be prepared by milling and sieving a hydrotalcite-type catalyst. The catalyst will be firstly conditioned under $N_2$ and $H_2O_g$ for at least 1 hour at reaction temperature before adding the reaction gas mixture.

The process section will be heated at 275° C. by heat exchange with the heat exchange fluid flowing in the first heat exchange microchannel, while water is fed through an opening positioned at the upstream end of the process microchannels. This process section will be maintained at 500 kPa.

Ethylene oxide gas will be fed through a second set of feed channels upstream of the process microchannels. The molar ratio of ethylene oxide to water will be 1:10.

As an alternative, ethylene oxide and water (molar ratio 1 to 10) will be fed into the microchannel process section using one feed channel upstream of the process section.

The product mixture exiting the process section, containing the desired mono-ethylene glycol will be further processed and/or purified by a conventional method.

Example 7

This prophetic example describes how an embodiment of this invention may be practiced.

The microchannel reactor will be assembled in accordance with methods known from WO-A-2004/099113, and references cited therein.

A microchannel reactor will comprise process microchannels, heat exchange microchannels, and feed channels.

The process microchannel section will comprise a hydrolysis catalyst comprising cobalt, zinc and alumina as described above.

The process microchannel reactor will be filled with a hydrolysis catalyst that will be prepared by milling and sieving a hydrotalcite type catalyst. The catalyst will be firstly conditioned under $N_2$ and $H_2O_g$ for at least 1 hour at reaction temperature before adding the reaction gas mixture.

Two such microchannel reactors will be operated in swing mode in parallel, in which simultaneously one reactor is operated with EO/water feed to produce glycol and the other reactor is operated at higher temperature and lower pressure to evaporate condensed higher glycols from the catalyst surface.

The process section will be heated at 275° C. by heat exchange with the heat exchange fluid flowing in the first heat exchange microchannel, while water is fed through an opening positioned at the upstream end of the process microchannels. This process section will be maintained at 500 kPa.

Ethylene oxide gas will be fed through a second set of feed channels upstream of the process microchannels. The molar ratio of ethylene oxide to water will be 1:10.

As an alternative ethylene oxide and water (molar ratio 1 to 10) will be fed into the microchannel process section using one feed channel upstream of the process section.

Simultaneously the second microchannel reactor will be operated at 350° C. and 200 kPa without feeding ethylene oxide/water.

Conditions and feed of both parallel reactors will be changed every 30 seconds.

The product mixture exiting the process section, containing the desired mono-ethylene glycol may be further processed and/or purified by a suitable method.

Example 8

This prophetic example describes how an embodiment of this invention may be practiced.

The microchannel reactor will be assembled in accordance with methods known from WO-A-2004/099113, and references cited therein.

A microchannel reactor will comprise process microchannels, heat exchange microchannels, and feed channels.

The process microchannel section will comprise a hydrolysis catalyst comprising cobalt, zinc and alumina as described above.

The process microchannel reactor will be filled with a hydrolysis catalyst that will be prepared by milling and sieving a hydrotalcite type catalyst. The catalyst will be firstly conditioned under $N_2$ and $H_2O_g$ for at least 1 hour at reaction temperature before adding the reaction gas mixture.

The process section will be heated at 275° C. by heat exchange with the heat exchange fluid flowing in the first heat exchange microchannel, while water is fed through an opening positioned at the upstream end of the process microchannels. This process section will be maintained at 500 kPa.

Ethylene oxide gas will be fed through a second set of feed channels upstream of the process microchannels. The molar ratio of ethylene oxide to water will be 1:10.

As an alternative, ethylene oxide and water (molar ratio 1 to 10) will be fed into the microchannel process section using one feed channel upstream of the process section.

The vapor phase product mixture exiting the process section, containing unreacted ethylene oxide, water, and the desired mono-ethylene glycol will be further processed in a second set of parallel microchannel reactors operating in swing mode. One reactor will be fed with the product mixture from the process section and will operate at a lower temperature of 120° C. to enable condensation of the monoethylene glycol, while the unreacted ethylene oxide and water will be recycled back to the process microchannel reactor. The other parallel reactor will operate at an elevated temperature of 200° C. to vaporize condensed monoethylene glycol for further processing and purification. Conditions and feed of both parallel reactors will be changed every 60 seconds.

The description titled "IMPROVEMENTS IN EPOXIDATION CATALYSTS AND METHODS", which follows hereinafter, describes an invention and embodiments thereof which may suitably be applied in conjunction with the invention and embodiments thereof described hereinbefore. The invention and embodiments thereof described hereinbefore may suitably be applied in conjunction with the invention and embodiments thereof described in the description hereinafter. It is to be understood that the invention and embodiments thereof described hereinbefore are independent of, and may be practiced separately from the inventions and embodiments described hereinafter. It is also to be understood that the invention and embodiments thereof described hereinafter are independent of, and may be practiced separately from the inventions and embodiments described hereinbefore. Further, it is to be understood that the description titled "IMPROVEMENTS IN EPOXIDATION CATALYSTS AND METHODS" is a self-contained description, which forms together with the description provided hereinbefore an integral disclosure of an invention and embodiments thereof. FIGS. 1-6 referred to in the description hereinafter are identical to FIGS. 1-6, respectively, referred to hereinbefore.

IMPROVEMENTS IN THE EPOXIDATION CATALYSTS AND METHODS

Background Of The Invention

Ethylene oxide and other olefin oxides are important industrial chemicals used as a feedstock for making such chemicals as ethylene glycol, propylene glycol, ethylene glycol ethers, ethylene carbonate, ethanol amines and detergents. One method for manufacturing an olefin oxide is by olefin epoxidation, that is the catalyzed partial oxidation of the olefin with oxygen yielding the olefin oxide. The olefin oxide so manufactured may be reacted with water, an alcohol, carbon dioxide, or an amine to produce a 1,2-diol, a 1,2-diol ether, a 1,2-carbonate or an alkanol amine. Such production of a 1,2-diol, a 1,2-diol ether, a 1,2-carbonate or an alkanol amine is generally carried out separately from the manufacture of the olefin oxide, in any case the two processes are normally carried out in separate reactors.

In olefin epoxidation, a feed containing the olefin and oxygen is passed over a bed of catalyst contained within a reaction zone that is maintained at certain reaction conditions. A commercial epoxidation reactor is generally in the form of a shell-and-tube heat exchanger, in which a plurality of substantially parallel elongated, relatively narrow tubes are filled with shaped catalyst particles to form a packed bed, and in which the shell contains a coolant. Irrespective of the type of epoxidation catalyst used, in commercial operation the internal tube diameter is frequently in the range of from 20 to 40 mm, and the number of tubes per reactor may range in the thousands, for example up to 12,000.

Olefin epoxidation is generally carried out with a relatively low olefin conversion and oxygen conversion. Recycle of unconverted olefin and oxygen is normally applied in order to enhance the economics of the process. Generally the feed additionally comprises a large quantity of so-called ballast gas to facilitate operation outside the explosion limits. Ballast gas includes saturated hydrocarbons, in particular methane and ethane. As a consequence, recycling generally involves the handling of large quantities of process streams, which includes the unconverted olefin, unconverted oxygen and the ballast gas. The processing of the recycle stream as normally applied in an olefin epoxidation plant is also fairly complex, as it involves olefin oxide recovery, carbon dioxide removal, water removal and re-pressurizing. The use of ballast gas not only contributes to the cost of processing, it also reduces the epoxidation reaction rate.

The epoxidation catalyst generally contains the catalytically active species, typically a Group 11 metal (in particular silver) and promoter components, on a shaped carrier material. Shaped carrier materials are generally carefully selected to meet requirements of, for example, strength and resistance against abrasion, surface area and porosity. The shaped carrier materials are generally manufactured by sintering selected inorganic materials to the extent that they have the desired properties.

During the epoxidation, the catalyst is subject to a performance decline, which represents itself by a loss in activity of the catalyst and selectivity in the formation the desired olefin oxide. In response to the loss of activity, the epoxidation reaction temperature may be increased such that the production rate of the olefin oxide is maintained. The operation of commercial reactors is normally limited with respect to the reaction temperature and when the applicable temperature limit has been reached, the production of the olefin oxide has to be interrupted for an exchange of the existing charge of epoxidation catalyst for a fresh charge.

It would be of great value if improved epoxidation processes and improved epoxidation reactors would become available.

SUMMARY OF THE INVENTION

The present invention provides such improved epoxidation processes and improved epoxidation reactors. Embodiments of the present invention make use of a reactor which comprises a plurality of microchannels ("process microchannels" hereinafter). The process microchannels may be adapted such that the epoxidation and optionally other processes can take place in the microchannels and that they are in a heat exchange relation with channels adapted to contain a heat exchange fluid ("heat exchange channels" hereinafter). A reactor comprising process microchannels is referred to herein by using the term "microchannel reactor". As used herein, the term "Group 11" refers to Group 11 of the Periodic Table of the Elements.

In an embodiment, the present invention provides a method of installing an epoxidation catalyst in one or more process microchannels of a microchannel reactor, which method comprises depositing a Group 11 metal or a cationic Group 11 metal component on at least a portion of the walls of the said process microchannels, depositing one or more promoter components on at least a portion of the same walls prior to, together with or subsequent to the deposition of the Group 11 metal or the cationic Group 11 metal component, and, if a cationic Group 11 metal component is deposited, reducing at least a portion of the cationic Group 11 metal component.

In another embodiment, the invention provides a process for the epoxidation of an olefin comprising installing an epoxidation catalyst in one or more process microchannels of a microchannel reactor by depositing a Group 11 metal or a cationic Group 11 metal component on at least a portion of the walls of the said process microchannels;

depositing one or more promoter components on at least a portion of the same walls prior to, together with or subsequent to the deposition of the Group 11 metal or the cationic Group 11 metal component; and, if a cationic Group 11 metal component is deposited, reducing at least a portion of the cationic Group 11 metal component, and reacting a feed comprising the olefin and oxygen in the presence of the epoxidation catalyst installed in the one or more process microchannels.

In another embodiment, the invention provides a process for the preparation of a 1,2-diol, a 1,2-diol ether, a 1,2-carbonate or an alkanol amine, which process comprises installing an epoxidation catalyst in one or more process microchannels of a microchannel reactor by depositing a Group 11 metal or a cationic Group 11 metal component on at least a portion of the walls of the said process microchannels;

depositing one or more promoter components on at least a portion of the same walls prior to, together with or subsequent to the deposition of the Group 11 metal or the cationic Group 11 metal component; and, if a cationic Group 11 metal component is deposited, reducing at least a portion of the cationic Group 11 metal component, reacting a feed comprising the olefin and oxygen in the presence of the epoxidation catalyst installed in the one or more process microchannels to produce an olefin oxide, and converting the olefin oxide with water, an alcohol, carbon dioxide or an amine to form the 1,2-diol, 1,2-diol ether, 1,2-carbonate or alkanol amine.

In another embodiment, the invention provides a method of installing an epoxidation catalyst in one or more process microchannels of a microchannel reactor, which method comprises introducing into the one or more process microchannels a dispersion of the catalyst in an essentially non-aqueous diluent, and removing at least a portion of the diluent.

In another embodiment, the invention provides a process for the epoxidation of an olefin comprising installing an epoxidation catalyst in one or more process microchannels of a microchannel reactor by introducing into the one or more process microchannels a dispersion of the catalyst in an essentially non-aqueous diluent; and removing at least a portion of the diluent, and reacting a feed comprising the olefin and oxygen in the presence of the epoxidation catalyst installed in the one or more process microchannels.

In another embodiment, the invention provides a process for the preparation of a 1,2-diol, a 1,2-diol ether, 1,2-carbonate or an alkanol amine, which process comprises installing an epoxidation catalyst in one or more process microchannels of a microchannel reactor by introducing into the one or more process microchannels a dispersion of the catalyst in an essentially non-aqueous diluent; and removing at least a portion of the diluent, reacting a feed comprising the olefin and oxygen in the presence of the epoxidation catalyst installed in the one or more process microchannels to produce an olefin oxide, and converting the olefin oxide with water, an alcohol, carbon dioxide or an amine to form the 1,2-diol, 1,2-diol ether, 1,2-carbonate or alkanol amine.

In another embodiment, the invention provides a method of preparing a particulate epoxidation catalyst, which method comprises depositing a Group 11 metal and one or more promoter components on a particulate carrier material having a pore size distribution such that pores with diameters in the range of from 0.2 to 10 μm represent at least 70% of the total pore volume.

In another embodiment, the invention provides a particulate epoxidation catalyst, which catalyst comprises a Group 11 metal and one or more promoter components deposited on a particulate carrier material having a pore size distribution such that pores with diameters in the range of from 0.2 to 10 μm represent at least 70% of the total pore volume.

In another embodiment, the invention provides a process for the epoxidation of an olefin comprising reacting a feed comprising the olefin and oxygen in the presence an epoxidation catalyst installed in one or more process microchannels of a microchannel reactor, which epoxidation catalyst comprises a Group 11 metal and one or more promoter components deposited on a particulate carrier material having a pore size distribution such that pores with diameters in the range of from 0.2 to 10 μm represent at least 70% of the total pore volume.

In another embodiment, the invention provides a process for the preparation of a 1,2-diol, a 1,2-diol ether, a 1,2-carbonate or an alkanol amine, which process comprises reacting a feed comprising the olefin and oxygen in the presence an epoxidation catalyst installed in one or more process microchannels of a microchannel reactor to produce an olefin oxide, which epoxidation catalyst comprises a Group 11 metal and one or more promoter components deposited on a particulate carrier material having a pore size distribution such that pores with diameters in the range of from 0.2 to 10 μm represent at least 70% of the total pore volume, and converting the olefin oxide with water, an alcohol, carbon dioxide or an amine to form the 1,2-diol, 1,2-diol ether, 1,2-carbonate or alkanol amine.

In another embodiment, the invention provides a process for the epoxidation of an olefin comprising reacting a feed comprising the olefin and oxygen in a total quantity of at least 50 mole-%, relative to the total feed, in the presence an epoxidation catalyst contained in one or more process microchannels of a microchannel reactor.

In another embodiment, the invention provides a process for the preparation of a 1,2-diol, a 1,2-diol ether, a 1,2-carbonate or an alkanol amine, which process comprises reacting a feed comprising the olefin and oxygen in a total quantity of at least 50 mole-%, relative to the total feed, in the presence an epoxidation catalyst contained in one or more process microchannels of a microchannel reactor to produce an olefin oxide, and converting the olefin oxide with water, an alcohol, carbon dioxide or an amine to form the 1,2-diol, 1,2-diol ether, 1,2-carbonate or alkanol amine.

In another embodiment, the invention provides a process for the epoxidation of an olefin comprising reacting a feed comprising the olefin and oxygen in the presence an epoxidation catalyst contained in one or more process microchannels of a microchannel reactor, and applying conditions for reacting the feed such that the conversion of the olefin or the conversion of oxygen is at least 90 mole-%.

In another embodiment, the invention provides a process for the preparation of a 1,2-diol, a 1,2-diol ether, a 1,2-carbonate or an alkanol amine, which process comprises reacting a feed comprising the olefin and oxygen in the presence an epoxidation catalyst contained in one or more process microchannels of a microchannel reactor to produce an olefin oxide, and applying conditions for reacting the feed such that the conversion of the olefin or the conversion of oxygen is at least 90 mole-%, and converting the olefin oxide with water, an alcohol, carbon dioxide or an amine to form the 1,2-diol, 1,2-diol ether, 1,2-carbonate or alkanol amine.

In another embodiment, the invention provides a method of rejuvenating an epoxidation catalyst, which method comprises washing the catalyst with an aqueous liquid, and depositing one or more promoter components on the washed catalyst.

In another embodiment, the invention provides a process for the epoxidation of an olefin comprising rejuvenating an epoxidation catalyst which has been used in an epoxidation process, which rejuvenation comprises washing the catalyst with an aqueous liquid; and depositing one or more promoter components on the washed catalyst, and reacting a feed comprising the olefin and oxygen in the presence of the rejuvenated catalyst.

In another embodiment, the invention provides a process for the preparation of a 1,2-diol, a 1,2-diol ether, a 1,2-carbonate or an alkanol amine, which process comprises rejuvenating an epoxidation catalyst which has been used in an epoxidation process, which rejuvenation comprises washing the catalyst with an aqueous liquid; and depositing one or more promoter components on the washed catalyst, reacting a feed comprising the olefin and oxygen in the presence of the rejuvenated catalyst to produce an olefin oxide, and converting the olefin oxide with water, an alcohol, carbon dioxide or an amine to form the 1,2-diol, 1,2-diol ether, 1,2-carbonate or alkanol amine.

In another embodiment, the invention provides a reactor suitable for the epoxidation of an olefin, which reactor is a microchannel reactor comprising one or more process microchannels comprising an upstream end, a downstream end, a first section which is adapted to contain an epoxidation catalyst, to receive a feed comprising an olefin and oxygen, and to cause conversion of at least a portion of the feed to form an olefin oxide in the presence of the epoxidation catalyst, and a second section positioned downstream of the first section which is adapted to receive and to cause quenching of the olefin oxide by heat exchange with a heat exchange fluid.

The reactor of the latter embodiment may comprise additionally one or more first heat exchange channels adapted to exchange heat with the first section of the said process microchannels, and one or more second heat exchange channels adapted to exchange heat with the second section of the said process microchannels.

In another embodiment, the invention provides a process for the epoxidation of an olefin comprising reacting a feed comprising an olefin and oxygen in the presence of an epoxidation catalyst contained in a first section of one or more process microchannels of a microchannel reactor to thereby form an olefin oxide, and quenching the olefin oxide in a second section of the one or more process microchannels positioned downstream of the first section by heat exchange with a heat exchange fluid.

In another embodiment, the invention provides a process for the preparation of a 1,2-diol, a 1,2-diol ether, a 1,2-carbonate or an alkanol amine, which process comprises reacting a feed comprising an olefin and oxygen in the presence of an epoxidation catalyst contained in a first section of one or more process microchannels of a microchannel reactor to thereby form an olefin oxide, quenching the olefin oxide in a second section of the one or more process microchannels positioned downstream of the first section by heat exchange with a heat exchange fluid, and converting the olefin oxide with water, an alcohol, carbon dioxide or an amine to form the 1,2-diol, 1,2-diol ether, 1,2-carbonate or alkanol amine.

In another embodiment, the invention provides a process for the epoxidation of an olefin comprising reacting a feed comprising an olefin and oxygen in the presence of an epoxidation catalyst to thereby form a first mixture comprising the olefin oxide and carbon dioxide, quenching the first mixture, typically, by heat exchange with a heat exchange fluid, and converting the quenched first mixture to form a second mixture comprising the olefin oxide and a 1,2-carbonate.

Preferably, in this embodiment, the invention provides a process for the epoxidation of an olefin comprising reacting a feed comprising an olefin and oxygen in the presence of an epoxidation catalyst contained in a first section of one or more process microchannels of a microchannel reactor to thereby form a first mixture comprising the olefin oxide and carbon dioxide, quenching the first mixture in a first intermediate section of the one or more process microchannels positioned downstream of the first section by heat exchange with a heat exchange fluid, and converting in a second section of the one or more process microchannels positioned downstream of the first intermediate section the quenched first mixture to form a second mixture comprising the olefin oxide and a 1,2-carbonate.

In this embodiment, when the second mixture is formed at least partly as a gaseous phase, the process may additionally comprise condensing in a third section of the one or more process microchannels positioned downstream of the second section at least a portion of the second mixture comprising the olefin oxide and the 1,2-carbonate. Preferably, in cases that the second mixture comprises water at least partly as a gaseous phase, the process may additionally comprise condensing, typically in the third section, at least a portion of such water present in the second mixture.

In another embodiment, the invention provides a process for the preparation of a 1,2-diol, a 1,2-diol ether, a 1,2-carbonate or an alkanol amine, which process comprises reacting a feed comprising an olefin and oxygen in the presence of an epoxidation catalyst to thereby form a first mixture comprising the olefin oxide and carbon dioxide, quenching the first mixture, typically, by heat exchange with a heat exchange fluid, converting the quenched first mixture to form a second mixture comprising the olefin oxide and a 1,2-carbonate, and converting the second mixture with water, an alcohol, carbon dioxide or an amine to form the 1,2-diol, 1,2-diol ether, 1,2-carbonate or alkanol amine.

In this embodiment, the second mixture is preferably converted with water to form the 1,2-diol.

In another embodiment, the invention provides a reactor suitable for the preparation of a 1,2-diol, a 1,2-diol ether, a 1,2-carbonate or an alkanol amine, which reactor is a microchannel reactor comprising one or more process microchannels comprising
an upstream end,
a downstream end,
a first section which is adapted to contain an epoxidation catalyst, to receive a feed comprising an olefin and oxygen, and to cause conversion of at least a portion of the feed to form an olefin oxide in the presence of the epoxidation catalyst, and
a second section positioned downstream of the first section which is adapted to receive the olefin oxide; to receive water, an alcohol, carbon dioxide or an amine; and to cause conversion of the olefin oxide to form the 1,2-diol, 1,2-diol ether, 1,2-carbonate or alkanol amine.

The reactor of the latter embodiment may comprise additionally one or more first heat exchange channels adapted to exchange heat with the first section of the said process microchannels, and one or more second heat exchange channels adapted to exchange heat with the second section of the said process microchannels.

Further, the one or more process microchannels may comprise additionally an intermediate section downstream from the first section and upstream from the second section, which intermediate section is adapted to control the temperature of the olefin oxide. In particular, the reactor may comprise additionally one or more third heat exchange channels adapted to exchange heat with the intermediate section of the said process microchannels.

The second section may additionally be adapted to contain a catalyst.

In another embodiment, the invention provides a process for the preparation of a 1,2-diol, a 1,2-diol ether, a 1,2-carbonate or an alkanol amine, which process comprises reacting a feed comprising an olefin and oxygen in the presence of an epoxidation catalyst contained in a first section of one or more process microchannels of a microchannel reactor to form an olefin oxide, and converting the olefin oxide with water, an alcohol, carbon dioxide or an amine to form the 1,2-diol, 1,2-diol ether, 1,2-carbonate or alkanol amine in a second section of the one or more process microchannels positioned downstream of the first section.

In another embodiment, the invention provides a reactor suitable for the preparation of a 1,2-diol, which reactor is a microchannel reactor comprising one or more process microchannels comprising an upstream end,
a downstream end,
a first section which is adapted to contain an epoxidation catalyst, to receive a feed comprising an olefin and oxygen, and to cause conversion of at least a portion of the feed to form an olefin oxide in the presence of the epoxidation catalyst,
a second section positioned downstream of the first section which is adapted to receive the olefin oxide, to receive carbon dioxide, and to cause conversion of the olefin oxide to form a 1,2-carbonate, and
a third section positioned downstream of the first section which is adapted to receive the 1,2-carbonate, to receive water or an alcohol, and to cause conversion of the 1,2-carbonate to form a 1,2-diol.

The reactor of the latter embodiment may comprise additionally one or more first heat exchange channels adapted to exchange heat with the first section of the said process microchannels, one or more second heat exchange channels adapted to exchange heat with the second section of the said process microchannels, and one or more third heat exchange channels adapted to exchange heat with the third section of the said process microchannels.

Further, the one or more process microchannels may comprise additionally a first intermediate section downstream from the first section and upstream from the second section, which first intermediate section is adapted to control the temperature of the olefin oxide, and a second intermediate section downstream from the second section and upstream from the third section, which second intermediate section is adapted to control the temperature of the 1,2-carbonate.

In particular, the reactor may comprise additionally one or more fourth heat exchange channels adapted to exchange heat with the first intermediate section of the said process microchannels, and one or more fifth heat exchange channels adapted to exchange heat with the second intermediate section of the said process microchannels.

The second section may additionally be adapted to contain a carboxylation catalyst.

In another embodiment, the invention provides a process for the preparation of a 1,2-diol, which process comprises reacting a feed comprising an olefin and oxygen in the presence an epoxidation catalyst contained in a first section of one or more process microchannels of a microchannel reactor to form an olefin oxide, converting the olefin oxide with carbon dioxide to form a 1,2-carbonate in a second section of the one or more process microchannels positioned downstream of the first section, and converting the 1,2-carbonate with water or an alcohol to form the 1,2-diol in a third section of the one or more process microchannels positioned downstream of the second section.

In another embodiment, the invention provides a process for the preparation of a 1,2-diol, a 1,2-diol ether, a 1,2-carbonate or an alkanol amine, which process comprises reacting in one or more process microchannels of a microchannel reactor an olefin oxide with water, an alcohol, carbon dioxide or an amine to form the 1,2-diol, 1,2-diol ether, 1,2-carbonate or alkanol amine.

In another embodiment, the invention provides a process for the preparation of a 1,2-diol, which process comprises converting in one or more process microchannels of a microchannel reactor a 1,2-carbonate with water or an alcohol to form the 1,2-diol.

DESCRIPTION OF THE DRAWINGS

FIG. 1 shows a schematic of a microchannel reactor and its main constituents.

FIG. 2 shows a schematic of a typical example of a repeating unit which comprises process microchannels and heat exchange channels and its operation when in use in the practice of the invention. A microchannel reactor of this invention may comprise a plurality of such repeating units.

FIG. 3 shows a schematic drawing of an example of a process for the preparation of ethylene oxide.

FIG. 4 shows a schematic drawing of an example of a process for the purification of ethylene oxide.

FIG. 5 shows a schematic drawing of an example of a typical process for the removal of combustible volatile contaminant materials from a process stream.

FIG. 6 shows a schematic drawing of an example of a glycol production unit.

DETAILED DESCRIPTION OF THE INVENTION

The use of a microchannel reactor in accordance with this invention leads to one or more of the following advantages:

the epoxidation catalyst does not necessarily involve the use a shaped carrier, which can eliminate the need for a step for producing a shaped carrier.

quenching of the olefin oxide inside the process microchannel enables operation under conditions which may be within explosion limits when such conditions would be applied in a conventional shell-and-tube heat exchanger reactor. Such conditions may be achieved by contacting an oxygen rich feed component with an olefin rich feed component within the process microchannels, which oxygen rich feed component and olefin rich feed component are normally outside the explosion limits. Quenching inside the process microchannels also decreases the formation of byproducts, such as aldehydes and carboxylic acids.

the epoxidation within the process microchannels can advantageously be carried out at conditions of high total concentration of the olefin, oxygen and the olefin oxide, which can lead to a higher epoxidation rate and/or lower epoxidation reaction temperature. Lowering the epoxidation reaction temperature can lead to improved selectivity and improved catalyst life. Employing conditions of high total concentration of the olefin, oxygen and the olefin oxide can also eliminate the need of using a ballast gas, which provides more efficient processing and reduction of the costs of recycling.

the epoxidation carried out in process microchannels may be operated at a high conversion level of oxygen or the olefin oxide. In particular when the process is carried out at a high olefin conversion level, it is advantageous to operate the epoxidation process in once-through operation, which implies that no recycle stream is applied. In addition, it is advantageous that in such case air may be fed to the process microchannels, instead of oxygen separated from air, which can eliminate the need for an air separation unit.

a rejuvenation technique can be carried out while the epoxidation catalyst is maintained inside the reactor, eliminating the need for the exchange of catalysts.

carrying out the olefin epoxidation inside the process microchannels enables quenching inside the same process microchannels and conversion of the co-formed carbon dioxide with at least a portion of the produced olefin oxide, and optionally condensing a liquid, typically aqueous, mixture comprising unconverted olefin oxide and the 1,2-carbonate. In respect of its composition, a remaining gaseous stream which may comprise unconverted ethylene and oxygen is suitable for recycle. This can reduce the complexity of the further processing of product and recycle streams, eliminating the need for, for example, an olefin oxide recovering unit and a carbon dioxide removal unit.

carrying out the olefin epoxidation inside the process microchannels enables conversion of the formed olefin oxide inside the same process microchannels to 1,2-diol, 1,2-diol ether, 1,2-carbonate or alkanol amine. This can eliminate the need for additional reactors for such further conversion. It can also eliminate the need for an olefin oxide recovering unit and/or a carbon dioxide removal unit, and it can reduce the need for heat exchanging equipment. Hence, it can reduce the complexity of the additional processing conventionally applied in a manufacturing plant, for example for product recovery. Conversion of the olefin oxide inside the process microchannels also decreases the formation of byproducts, such as aldehydes and carboxylic acids.

carrying out the conversion of an olefin oxide into a 1,2-diol, a 1,2-diol ether, a 1,2-carbonate or an alkanol amine inside the process microchannels of a microchannel reactor has the advantageous effect that there is no need to have the reactants present in the reactor in a relatively high dilution. When such reactions are carried out in conventional equipment, a relatively high degree of dilution is frequently applied, for example by having a relatively large excess of, for example, water, alcohol or amine present as diluent. The relatively large amount of diluent, added to the reaction mixture as a relatively cold component, acts as a heat sink. Acting as a heat sink means preventing a large increase of the temperature by having the capability to absorb the heat of reaction. The use of a relatively large amount of diluent is a disadvantage, in that it increases the reaction times and/or reactor volumes and it creates relatively large recycle streams, which all influence the process economics in a unfavorable manner. By the application of a microchannel reactor, a high degree of dilution may be avoided. However, in the presence of less diluent, in particular less excess of water, alcohol or amine, the selectivity to the desired product will become less.

Microchannel reactors suitable for use in this invention and their operation have been described in WO-A-2004/099113, WO-A-01/12312, WO-01/54812, U.S. Pat. No. 6,440,895, U.S. Pat. No. 6,284,217, U.S. Pat. No. 6,451,864, U.S. Pat. No. 6,491,880, U.S. Pat. No. 6,666,909, U.S. Pat. No. 6,811,829, U.S. Pat. No. 6,851,171, U.S. Pat. No. 6,494,614, U.S. Pat. No. 6,228,434 and U.S. Pat. No. 6,192,596, which are incorporated herein by reference. Methods by which the microchannel reactor may be manufactured, loaded with catalyst and operated, as described in these references, may generally be applicable in the practice of the present invention.

With reference to FIG. 1, microchannel reactor 100 may be comprised of a process header 102, a plurality of process microchannels 104, and a process footer 108. The process header 102 provides a passageway for fluid to flow into the process microchannels 104. The process footer 108 provides a passageway for fluid to flow from the process microchannels 104.

The number of process microchannels contained in a microchannel reactor may be very large. For example, the number may be up to $10^5$, or even up to $10^6$ or up to $2 \times 10^6$. Normally, the number of process microchannels may be at least 10 or at least 100, or even at least 1000.

The process microchannels are typically arranged in parallel, for example they may form an array of planar microchannels. The process microchannels may have at least one internal dimension of height or width of up to 15 mm, for example from 0.05 to 10 mm, in particular from 0.1 to 5 mm, more in particular from 0.5 to 2 mm. The other internal dimension of height or width may be, for example, from 0.1 to 100 cm, in particular from 0.2 to 75 cm, more in particular from 0.3 to 50 cm. The length of the process microchannels may be, for example, from 1 to 500 cm, in particular from 2 to 300 cm, more in particular from 3 to 200 cm, or from 5 to 100 cm.

The microchannel reactor 100 additionally comprises heat exchange channels (not shown in FIG. 1) which are in heat exchange contact with the process microchannels 104. The heat exchange channels may also be microchannels. The microchannel reactor is adapted such that heat exchange fluid can flow from heat exchange header 110 through the heat exchange channels to heat exchange footer 112. The heat exchange channels may be aligned to provide a flow in a co-current, counter-current or, preferably, cross-current direction, relative to a flow in the process microchannels 104. The cross-current direction is as indicated by arrows 114 and 116.

The heat exchange channels may have at least one internal dimension of height or width of up to 15 mm, for example from 0.05 to 10 mm, in particular from 0.1 to 5 mm, more in particular from 0.5 to 2 mm. The other internal dimension of height or width may be, for example, from 0.1 to 100 cm, in particular from 0.2 to 75 cm, more in particular from 0.3 to 50 cm. The length of the heat exchange channels may be, for example, from 1 to 500 cm, in particular from 2 to 300 cm, more in particular from 3 to 200 cm, or from 5 to 100 cm.

The separation between a process microchannel 104 and the next adjacent heat exchange channel may be in the range of from 0.05 mm to 5 mm, in particular from 0.2 to 2 mm.

In some embodiments of this invention, there is provided for first heat exchange channels and second heat exchange channels, or first heat exchange channels, second heat exchange channels and third heat exchange channels, or even up to fifth heat exchange channels, or even further heat exchange channels. Thus, in such cases, there is a plurality of sets of heat exchange channels, and accordingly there may be a plurality of heat exchange headers 110 and heat exchange footers 112, whereby the sets of heat exchange channels may be adapted to receive heat exchange fluid from a heat exchange header 110 and to deliver heat exchange fluid into a heat exchange footer 112.

The process header 102, process footer 108, heat exchange header 110, heat exchange footer 112, process microchannels 104 and heat exchange channels may independently be made of any construction material which provides sufficient strength, dimensional stability and heat transfer characteristics to permit operation of the processes in accordance with this invention. Suitable construction materials include, for example, steel (for example stainless steel and carbon steel), monel, titanium, copper, glass and polymer compositions. The kind of heat exchange fluid is not material to the present invention and the heat exchange fluid may be selected from a large variety. Suitable heat exchange fluids include steam, water, air and oils. In embodiments of the invention which include a plurality of sets of heat exchange channels, such sets of heat exchange channels may operate with different heat exchange fluids or with heat exchange fluids having different temperatures.

A microchannel reactor according to the invention may comprise a plurality of repeating units comprising one or more process microchannels and one or more heat exchange channels. Reference is now made to FIG. 2, which shows a typical repeating unit and its operation.

Process microchannels 210 have an upstream end 220 and a downstream end 230 and may comprise of a first section 240 which may contain a catalyst (not drawn), for example an epoxidation catalyst. First section 240 may be in heat exchange contact with first heat exchange channel 250, allowing heat exchange between first section 240 of process microchannel 210 and first heat exchange channel 250. The repeating unit may comprise first feed channel 260 which ends into first section 240 through one or more first orifices 280. Typically one or more first orifices 280 may be positioned downstream relative to another first orifice 280. During operation, feed comprising the olefin and oxygen may enter into first section 240 of process microchannel 210 through an opening in upstream end 220 and/or through first feed channel 260 and one or more first orifices 280.

Process microchannels 210 may comprise a second section 340 which may or may not be adapted to contain a catalyst. Second section 340 may or may not contain a catalyst, as described herein. Second section 340 is positioned downstream of first section 240. Second section 340 may be in heat exchange contact with second heat exchange channel 350, allowing heat exchange between second section 340 of process microchannel 210 and second heat exchange channel 350. In some embodiments second section 340 is adapted to quench olefin oxide obtained in and received from first section 240 by heat exchange with a heat exchange fluid in second heat exchange channel 350. Quenching may be achieved in one or more stages by the presence of a plurality of second heat exchange channels 350, for example two or three or four. Such a plurality of second heat exchange channels 350 may be adapted to contain heat exchange fluids having different temperatures, in particular such that in downstream direction of second section 340 heat exchange takes place with a second heat exchange channel 350 containing a heat exchange fluid having a lower temperature. The repeating unit may comprise second feed channel 360 which ends into second section 340 through one or more second orifices 380. During operation, feed may enter into second section 340 from upstream in process microchannel 210 and through second feed channel 360 and one or more second orifices 380.

Typically one or more second orifices 380 may be positioned downstream relative to another second orifice 380. In embodiments in which second section 340 is adapted for accommodating conversion of olefin oxide to 1,2-diol, 1,2-diol ether, 1,2-carbonate or alkanol amine, feed entering during operation through second feed channel 360 and one or more second orifices 380 may comprise water, the alcohol, carbon dioxide or the amine. Also, catalyst may be fed through second feed channel 360 and one or more second orifices 380. If desirable, a separate set of second feed channel (not drawn) with one or more second orifices (not drawn) may be present in order to accommodate separate feeding of feed and catalyst.

The first and second feed channels 260 or 360 in combination with first and second orifices 280 or 380, whereby one or more first or second orifices 280 or 380 are positioned downstream to another first or second orifice 280 or 380, respectively, allow for replenishment of a reactant. Replenishment of a reactant is a feature in some embodiments of this invention.

Process microchannels 210 may comprise an intermediate section 440, which is positioned downstream of first section 240 and upstream of second section 340. Intermediate section 440 may be in heat exchange contact with third heat exchange channel 450, allowing heat exchange between intermediate section 440 of process microchannel 210 and third heat exchange channel 450. In some embodiments intermediate section 440 is adapted to quench olefin oxide obtained in and received from first section 240 by heat exchange with a heat exchange fluid in third heat exchange channel 450. Quenching may be achieved in stages by the presence of a plurality of third heat exchange channels 450, for example two or three or four. Such a plurality of third heat exchange channels 450 may be adapted to contain heat exchange fluids having different temperatures, in particular such that in downstream direction of intermediate section 440 heat exchange takes place with a third heat exchange channel 450 containing a heat exchange fluid having a lower temperature.

In some embodiments, process microchannel 210 may comprise a third section (not drawn) downstream of second section 340, and optionally a second intermediate section (not drawn) downstream of second section 340 and upstream of the third section. The third section may or may not be adapted to contain a catalyst. The third section may or may not contain a catalyst, as described herein. The third section may be in heat exchange contact with a fourth heat exchange channel (not drawn), allowing heat exchange between the third section of the process microchannel 210 and fourth heat exchange channel. The second intermediate section may be in heat exchange contact with a fifth heat exchange channel (not drawn), allowing heat exchange between the second intermediate section of the process microchannel 210 and fifth heat exchange channel. The repeating unit may comprise a third feed channel (not drawn) which ends into the third section through one or more third orifices (not drawn). Typically one or more third orifices may be positioned downstream relative to another third orifice. During operation, feed may enter into the third section from upstream in process microchannel 210 and through the third feed channel and the one or more third orifices. In embodiments in which the third section is adapted for accommodating conversion of 1,2-carbonate into 1,2-diol, feed entering during operation through the third feed channel and the one or more third orifices may comprise water, an alcohol, or an alcohol/water mixture. Also, catalyst may be fed through the third feed channel and the one or more third orifices. If desirable, a separate set of third feed channels (not drawn) with one or more third orifices (not drawn) may be present in order to accommodate separate feeding of feed and catalyst.

The feed channels may be microchannels. They may have at least one internal dimension of height or width of up to 15 mm, for example from 0.05 to 10 mm, in particular from 0.1 to 5 mm, more in particular from 0.5 to 2 mm. The other internal dimension of height or width may be, for example, from 0.1 to 100 cm, in particular from 0.2 to 75 cm, more in particular from 0.3 to 50 cm. The length of the feed channels may be, for example, from 1 to 250 cm, in particular from 2 to 150 cm, and more particularly from 3 to 100 cm, or from 5 to 50 cm.

The length of the sections of the process microchannels may be selected independently of each other, in accordance with, for example, the heat exchange capacity needed or the quantity of catalyst which may be contained in the section. The lengths of the sections are preferably at least 1 cm, or at least 2 cm, or at least 5 cm. The lengths of the sections are preferably at most 250 cm, or at most 150 cm, or at most 100 cm, or at most 50 cm. Other dimensions of the sections are dictated by the corresponding dimensions of process microchannel 210.

The microchannel reactor of this invention may be manufactured using known techniques, for example conventional machining, laser cutting, molding, stamping and etching and combinations thereof. The microchannel reactor of this invention may be manufactured by forming sheets with features removed which allow passages. A stack of such sheets may be assembled to form an integrated device, by using known techniques, for example diffusion bonding, laser welding, cold welding, diffusion brazing, and combinations thereof. The microchannel reactor of this invention comprises appropriate headers, footers, valves, conduit lines, and other features to control input of reactants, output of product, and flow of heat exchange fluids. These are not shown in the drawings, but they can be readily provided by those skilled in the art. Also, there may be further heat exchange equipment (not shown in the drawings) for temperature control of feed, in particular for heating feed or feed components, before it enters the process microchannels, or for temperature control of product, in particular for quenching product, after it has left the process microchannels. Such further heat exchange equipment may be integral with the microchannel reactor, but more typically it will be separate equipment. These are not shown in the drawings, but they can be readily provided by those skilled in the art. Heat integration may be applied, for example by using reaction heat of the epoxidation process for heating feed components, or for other heating purposes.

Typically, the epoxidation catalysts are solid catalysts under the conditions of the epoxidation reaction. Such epoxidation catalyst, and any other solid catalysts as appropriate, may be installed by any known technique in the designated section of the process microchannels. The catalysts may form a packed bed in the designated section of the process microchannel and/or they may form a coating on at least a portion of the wall of the designated section of the process microchannels. The skilled person will understand that the coating will be positioned on the interior wall of the process microchannels. Alternatively or additionally, one or more of the catalysts may be in the form of a coating on inserts which may be placed in the designated section of the process microchannels. Coatings may be prepared by any deposition method, such as wash coating or vapor deposition. In some embodiments, the epoxidation catalyst may not be a solid catalyst under the conditions of the epoxidation, in which case the epoxidation catalyst may be fed to the designated section of the process microchannels together with one or more components of the epoxidation feed and may pass through the process microchannels along with the epoxidation reaction mixture.

The epoxidation catalyst which may be used in this invention is typically a catalyst which comprises one or more Group 11 metals. The Group 11 metals may be selected from the group consisting of silver and gold. Preferably, the Group 11 metal comprises silver. In particular, the Group 11 metal comprises silver in a quantity of at least 90% w, more in particular at least 95% w, for example at least 99% w, or at least 99.5% w, calculated as the weight of silver metal relative to the total weight of the Group 11 metal, as metal. Typically, the epoxidation catalyst additionally comprises one or more promoter components. More typically, the epoxidation catalyst comprises the Group 11 metal, one or more promoter components and additionally one or more components comprising one or more further elements. In some embodiments, the epoxidation catalyst may comprise a carrier material on which the Group 11 metal, any promoter components and any components comprising one or more further elements may be deposited. Suitable promoter components and suitable components comprising one or more further elements and suitable carrier materials may be as described hereinafter.

In an embodiment, the present invention provides a method of installing an epoxidation catalyst in one or more process microchannels of a microchannel reactor, which method comprises depositing one or more Group 11 metals or one or more cationic Group 11 metal components on at least a portion of the walls of the said process microchannels, depositing one or more promoter components on at least the same walls prior to, together with or subsequent to the deposition of the Group 11 metal(s) or the cationic Group 11 metal component(s), and, if a cationic Group 11 metal component is deposited, reducing at least a portion of the cationic Group 11 metal component(s).

Group 11 metal may be deposited on at least a portion of the walls of the process microchannels by contacting the walls with a liquid containing dispersed Group 11 metal, for example a Group 11 metal sol, and removing the liquid, for example by evaporation, while leaving Group 11 metal on the wall. Such deposition may be carried out more than once, for example two times or three times, to accomplish the deposition of a desired amount of Group 11 metal. The quantity of Group 11 metal in such liquid may be in the range of from 1 to 30% w, in particular from 2 to 15% w, relative to the weight of the liquid. The liquid may comprise additives, such as dispersants and stabilizers. Such additives may be removed after the removal of the liquid, by heating for example at a temperature of from 100 to 300° C., in particular from 150 to 250° C., in an inert atmosphere, for example in nitrogen or argon, or in an oxygen containing atmosphere, for example air or a mixture comprising oxygen and argon.

As an alternative, or in addition, Group 11 metal may be deposited on at least a portion of the walls of the process microchannels by vapor deposition techniques known in the art.

A cationic Group 11 metal component may be deposited on at least a portion of the walls of the process microchannels by contacting the walls with a liquid mixture comprising the cationic Group 11 metal component, and removing a liquid component of the liquid mixture. A reducing agent may be applied prior to, together with or after the deposition of cationic Group 11 metal component. Typically, the liquid mixture may comprise the cationic Group 11 metal component and a reducing agent, in which case removing the liquid and performing reduction of at least a portion of the cationic Group 11 metal component may be accomplished simultaneously. Such deposition may be carried out more than once, for example two times or three times, to accomplish the deposition of a desired amount of Group 11 metal. The cationic Group 11 metal component includes, for example a non-complexed or complexed Group 11 metal salt, in particular, a cationic Group 11 metal-amine complex. Contacting the walls with a liquid mixture comprising a cationic Group 11 metal-amine complex and a reducing agent may be followed by heating at a temperature of from 100 to 300° C., in particular from 150 to 250° C., in an inert atmosphere, for example in nitrogen or argon, or in an oxygen containing atmosphere, for example air or a mixture comprising oxygen and argon. The heating will, in general, effect the reduction of at least a portion of the cationic Group 11 metal-amine complex. Examples of cationic Group 11 metal-amine complexes are cationic Group 11 metal complexed with a monoamine or a diamine, in particular a 1,2-alkylene diamine. Examples of suitable amines are ethylene diamine, 1,2-propylene diamine, 2,3-butylene diamine, and ethanol amine. Higher amines may be used, such as, for example, triamines, tetraamines, and pentaamines. Examples of reducing agents are oxalates, lactates and formaldehyde. The quantity of Group 11 metal in such liquid mixture may be in the range of from 1 to 40% w, in particular from 2 to 30% w, calculated as the weight of the Group 11 metal relative to the weight of the liquid mixture. For further particulars of liquid mixtures comprising cationic Group 11 metal-amine complex and a reducing agent, reference may be made to U.S. Pat. No. 5,380,697, U.S. Pat. No. 5,739,075, EP-A-266015, and U.S. Pat. No. 6,368,998, which are incorporated herein by reference.

In some embodiments, Group 11 metal or cationic Group 11 metal component may be deposited on at least a portion of the walls of the process microchannels before the microchannel reactor is manufactured by assembling sheets, as described hereinbefore. In such embodiments portions of the walls on which no Group 11 metal is to be deposited may be shielded by a temporary coating. In other embodiments, Group 11 metal or cationic Group 11 metal component may be deposited on at least a portion of the walls of the process microchannels after they have been formed by assembling the sheets described hereinbefore. In such embodiments, inserts may be placed temporarily in the sections of the microchannels where no Group 11 metal is to be deposited on the walls.

In some embodiments, Group 11 metal or cationic Group 11 metal component may be deposited on at least a portion of the walls of the process microchannels wherein the said walls are at least partly covered with a carrier material, and Group 11 metal or cationic Group 11 metal component is deposited on or in the carrier material, suitably by using an impregnation method. The said walls may be at least partly covered with the carrier material by wash coating, prior to or after assembling the process microchannels. Particulars of suitable carrier materials are as specified hereinafter.

In some embodiments, the walls of the process microchannels on which Group 11 metal or cationic Group 11 metal component may be deposited are at least partly roughened or corrugated. Roughening or corrugation may provide grooves and elevations, so that the roughened or corrugated wall surface is effectively enlarged, for example, by a factor of from 0.5 to 10, or from 1 to 5, relative to the surface area of the roughened or corrugated wall surface as defined by its outer dimensions. This can increase the adhesion of the epoxidation catalyst deposited on the wall, and it will effect that more epoxidation catalyst surface can contribute in catalyzing the epoxidation reaction. Roughening and corrugation may be achieved by methods known in the art, for example by etching or by applying abrasive power.

In some embodiments, the said deposition of Group 11 metal or cationic Group 11 metal component, with subsequent reduction, will yield a Group 11 metal mirror positioned on the walls of the process microchannels, and in other embodiments this will yield discrete Group 11 metal particles, for example in the form of spheres. In yet other embodiments, a combination of a mirror and discrete particles will be yielded. Such morphology differences are not essential in the practice of the present invention.

One or more promoter components may be deposited on at least a portion of the same walls of the process microchannels as the walls on which Group 11 metal or cationic Group 11 metal component is deposited. The deposition of promoter components may be effected prior to, together with or subsequent to the deposition of Group 11 metal or cationic Group 11 metal component. Particulars of such promoter components, including suitable quantities thereof, are disclosed hereinafter. Suitable methods of depositing the promoter components may include, for example, contacting the walls with a liquid mixture comprising one or more of the promoter components to be deposited and a diluent, and removing the diluent while leaving at least a portion of the promoter component(s). In particular in embodiments in which the walls of the process microchannels are covered with a carrier materials, the liquid mixture may be kept in contact with the walls for a period of time before removing the diluent, for example for up to 10 hours, in particular for 0.25 to 5 hours, and the temperature may be up to 95° C., in particular in the range of from 10 to 80° C. Suitable liquids typically comprise the promoter component(s) dissolved or dispersed in an aqueous liquid, for example water or an aqueous organic diluent, such as for example a mixture of water and one or more of methanol, ethanol, propanol, isopropanol, acetone or methyl ethyl ketone. The deposition may be carried out more than once, for example two times or three times, to accomplish the deposition of a desired amount of promoter component. Alternatively, different promoter components may be deposited in different deposition steps.

In addition to one or more promoter components, one or more components comprising one or more further elements may be deposited on at least a portion of the same walls of the process microchannels as the walls on which Group 11 metal or cationic Group 11 metal component is deposited. The deposition of components comprising the further elements may be effected prior to, together with or subsequent to the deposition of Group 11 metal or cationic Group 11 metal component, and prior to, together with or subsequent to the deposition of the promoter components. Particulars of the components comprising the further elements, including suitable quantities thereof, are disclosed hereinafter. Suitable methods of depositing the components comprising the further elements include, for example, contacting the walls with a liquid mixture comprising one or more of the components to be deposited and a diluent, and removing the diluent while leaving at least a portion of the component(s). In particular in embodiments in which the walls of the process microchannels are covered with a carrier materials, the liquid mixture may be kept in contact with the walls for a period of time before removing the diluent, for example for up to 10 hours, in particular for 0.25 to 5 hours, and the temperature may be up to 95° C., in particular in the range of from 10 to 80° C. Suitable liquids typically comprise the component(s) dissolved or dispersed in an aqueous liquid, for example water or an aqueous organic diluent, such as for example a mixture of water and one or more of methanol, ethanol, propanol, isopropanol, tetrahydrofuran, ethylene glycol, ethylene glycol dimethyl ether, diethylene glycol dimethyl ether, dimethylformamide, acetone or methyl ethyl ketone. The deposition may be carried out more than once, for example two times or three times, to accomplish the deposition of a desired amount of the components. Alternatively, different components comprising a further element may be deposited in different deposition steps.

In an embodiment, the invention provides a method of installing an epoxidation catalyst in one or more process microchannels of a microchannel reactor, which method comprises introducing into the one or more process microchannels a dispersion of the catalyst dispersed in an essentially non-aqueous diluent, and removing the diluent.

The essentially non-aqueous diluent may be a liquid, or it may be in a gaseous form. As used herein, for liquid diluents, "essentially non-aqueous" means that the water content of the diluent is at most 20% w, in particular at most 10% w, more in particular at most 5% w, for example at most 2% w, or even at most 1% w, or at most 0.5% w, relative to the weight of the diluent. In particular, for gaseous diluents, "essentially non-aqueous" means that the diluent as present in the process microchannels is above the dew point. The substantial or complete absence of liquid water in the diluent enables the catalyst to better maintain its integrity during installation, in terms of one or more of its morphology, composition and properties, than when an aqueous diluent is applied. Suitable essentially non-aqueous liquid diluents include organic diluents, for example hydrocarbons, halogenated hydrocarbons, alcohols, ketones, ethers, and esters. Suitable alcohols include, for example methanol and ethanol. The quantity of catalyst which may be present in the liquid diluent may be in the range of from 1 to 50% w, in particular from 2 to 30% w, relative to the weight of the total of the catalyst and the liquid diluent.

Suitable essentially non-aqueous gaseous phase diluents include, for example, air, nitrogen, argon and carbon dioxide. The quantity of catalyst which may be present in the gaseous phase diluent may be in the range of from 10 to 500 g/l, in particular from 22 to 300 g/l, calculated as the weight of catalyst relative to the volume of the gaseous phase diluent.

The epoxidation catalyst present in the dispersion may be obtained by crushing a conventional, shaped catalyst and optionally followed by sieving. The particle size of the catalyst present in the dispersion is typically such that $d_{50}$ is in the range of from 0.1 to 100 μm, in particular from 0.5 to 50 μm. As used herein, the average particle size, referred to herein as "$d_{50}$", is as measured by a Horiba LA900 particle size analyzer and represents a particle diameter at which there are equal spherical equivalent volumes of particles larger and particles smaller than the stated average particle size. The method of measurement includes dispersing the particles by ultrasonic treatment, thus breaking up secondary particles into primary particles. This sonification treatment is continued until no further change in the $d_{50}$ value is noticed, which typically requires 5 minute sonification when using the Horiba LA900 particle size analyzer. Preferably, the epoxidation catalyst comprises particles having dimensions such that they pass a sieve with openings sized at most 50%, in particular at most 30% of the smallest dimension of the process microchannel.

Conventional, shaped epoxidation catalysts typically comprise Group 11 metal, one or more promoter components and optionally one or more components comprising a further element dispersed on a shaped carrier material. Suitable carrier materials, suitable promoter components, suitable components comprising a further element and suitable catalyst compositions in respect of the quantities of Group 11 metal, promoter components and components comprising a further element may be as described hereinafter.

Alternatively, and preferably, the catalyst present in the dispersion is prepared in accordance with the invention.

The dispersion of the catalyst may be introduced such that a packed catalyst bed is formed in the designated section of one or more of the process microchannels, or alternatively such that at least a portion of the walls of the said sections is covered with the catalyst. In the former case, prior to introducing the dispersion of the catalyst, a support device, for example a sieve or a graded particulate material, may have been placed in the downstream portion of the designated section of the one or more of the process microchannels, to support the catalyst and to prevent it from moving further downstream. In the latter case, the catalyst may be deposited on the walls of the process microchannels prior to or after assembling the process microchannels, or the catalyst may be present on inserts placed in the designated section of the process microchannels.

The total quantity of Group 11 metal present in the first section of the process microchannels is not material to the invention, and may be selected within wide ranges. Typically, the total quantity of Group 11 metal may be in the range of from 10 to 500 kg/m$^3$, more typically from 50 to 400 kg/m$^3$, in particular from 100 to 300 kg/m$^3$ reactor volume, wherein reactor volume is the total volume defined by the cross sectional area and the total length of the portions of the process microchannels which is occupied by the epoxidation catalyst, by presence of a packed bed and/or by the presence of the epoxidation catalyst on the wall. For the avoidance of doubt, the reactor volume so defined does not include portions of the process microchannel which do not comprise epoxidation catalyst. In embodiments of the invention wherein the feed comprises the olefin and oxygen in a total quantity of at least 50 mole-%, the total quantity of Group 11 metal may be in the range of from 5 to 250 kg/m$^3$, more typically from 20 to 200 kg/m$^3$, in particular from 50 to 150 kg/m$^3$ reactor volume, as defined hereinbefore.

In an embodiment, the invention provides a method of preparing a particulate epoxidation catalyst, which method comprises depositing Group 11 metal and one or more promoter components on a particulate carrier material having a pore size distribution such that pores with diameters in the range of from 0.2 to 10 μm represent at least 70% of the total pore volume.

The carrier materials for use in this invention may be natural or artificial inorganic materials and they may include refractory materials, silicon carbide, clays, zeolites, charcoal and alkaline earth metal carbonates, for example calcium carbonate. Preferred are refractory materials, such as alumina, magnesia, zirconia and silica. The most preferred material is α-alumina. Typically, the carrier material comprises at least 85% w, more typically at least 90% w, in particular at least 95% w α-alumina, frequently up to 99.9% w α-alumina, relative to the weight of the carrier. Other components of the α-alumina may comprise, for example, silica, alkali metal components, for example sodium and/or potassium components, and/or alkaline earth metal components, for example calcium and/or magnesium components.

The surface area of the carrier material may suitably be at least 0.1 m$^2$/g, preferably at least 0.3 m$^2$/g, more preferably at least 0.5 m$^2$/g, and in particular at least 0.6 m$^2$/g, relative to the weight of the carrier; and the surface area may suitably be at most 10 m$^2$/g, preferably at most 5 m$^2$/g, and in particular at most 3 m$^2$/g, relative to the weight of the carrier. "Surface area" as used herein is understood to relate to the surface area as determined by the B.E.T. (Brunauer, Emmett and Teller) method as described in Journal of the American Chemical Society 60 (1938) pp. 309-316. High surface area carrier materials, in particular when they are an α-alumina optionally comprising in addition silica, alkali metal and/or alkaline earth metal components, provide improved performance and stability of operation.

The water absorption of the carrier material is typically in the range of from 0.2 to 0.8 g/g, preferably in the range of from 0.3 to 0.7 g/g. A higher water absorption may be in favor in view of a more efficient deposition of Group 11 metal, promoter components and components comprising one or more elements. As used herein, water absorption is as measured in accordance with ASTM C20, and water absorption is expressed as the weight of the water that can be absorbed into the pores of the carrier, relative to the weight of the carrier.

The particulate carrier material may have a pore size distribution such that pores with diameters in the range of from 0.2 to 10 μm represent at least 70% of the total pore volume. Such relatively narrow pore size distribution can contribute to one or more of the activity, selectivity and longevity of the catalyst. Longevity may be in respect of maintaining the catalyst activity and/or maintaining the selectivity. As used herein, the pore size distribution and the pore volumes are as measured by mercury intrusion to a pressure of 3.0×10$^8$ Pa using a Micromeretics Autopore 9200 model (130° contact angle, mercury with a surface tension of 0.473 N/m, and correction for mercury compression applied).

Preferably, the pore size distribution is such that the pores with diameters in the range of from 0.2 to 10 μm represent more than 75%, in particular more than 80%, more preferably more than 85%, most preferably more than 90% of the total pore volume. Frequently, the pore size distribution is such that the pores with diameters in the range of from 0.2 to 10 μm represent less than 99.9%, more frequently less than 99% of the total pore volume.

Preferably, the pore size distribution is such that the pores with diameters in the range of from 0.3 to 10 μm represent more than 75%, in particular more than 80%, more preferably more than 85%, most preferably more than 90%, in particular up to 100%, of the pore volume contained in the pores with diameters in the range of from 0.2 to 10 μm.

Typically, the pore size distribution is such that pores with diameters less than 0.2 μm represent less than 10%, in particular less than 5%, of the total pore volume. Frequently, the pores with diameters less than 0.2 μm represent more than 0.1%, more frequently more than 0.5% of the total pore volume.

Typically, the pore size distribution is such that pores with diameters greater than 10 μm represent less than 20%, in particular less than 10%, more in particular less than 5%, of the total pore volume. Frequently, the pores with diameters greater than 10 μm represent more than 0.1%, in particular more than 0.5% of the total pore volume.

Typically, the pores with diameters in the range of from 0.2 to 10 μm provide a pore volume of at least 0.25 ml/g, in particular at least 0.3 ml/g, more in particular at least 0.35 ml/g. Typically, the pores with diameters in the range of from 0.2 to 10 μm provide a pore volume of at most 0.8 ml/g, more typically at most 0.7 ml/g, in particular at most 0.6 ml/g.

The particulate carrier material has typically a $d_{50}$ in the range of from 0.1 to 100 μm, in particular from 0.5 to 50 μm. Preferably, the particulate carrier material comprises particles having dimensions such that they pass an ASTM sieve with openings sized at most 50%, in particular 30% of the smallest dimension of the process microchannel.

The epoxidation catalyst which comprises one or more Group 11 metals dispersed on a carrier material exhibits appreciable catalytic activity when the Group 11 metal content is at least 10 g/kg, relative to the weight of the catalyst. Preferably, the catalyst comprises Group 11 metal in a quantity of from 50 to 500 g/kg, more preferably from 100 to 400 g/kg.

The promoter component may comprise one or more elements selected from rhenium, tungsten, molybdenum, chromium, and mixtures thereof. Preferably the promoter component comprises, as one of its elements, rhenium.

The promoter component may typically be present in the epoxidation catalyst in a quantity of at least 0.05 mmole/kg, more typically at least 0.5 mmole/kg, and preferably at least 1 mmole/kg, calculated as the total quantity of the element (that is rhenium, tungsten, molybdenum and/or chromium) relative to the weight of Group 11 metal. The promoter component may be present in a quantity of at most 250 mmole/kg, preferably at most 50 mmole/kg, more preferably at most 25 mmole/kg, calculated as the total quantity of the element relative to the weight of Group 11 metal. The form in which the promoter component may be deposited is not material to the invention. For example, the promoter component may suitably be provided as an oxide or as an oxyanion, for example, as a rhenate, perrhenate, or tungstate, in salt or acid form.

When the epoxidation catalyst comprises a rhenium containing promoter component, rhenium may typically be present in a quantity of at least 0.5 mmole/kg, more typically at least 2.5 mmole/kg, and preferably at least 5 mmole/kg, in particular at least 7.5 mmole/kg, calculated as the quantity of the element relative to the weight of Group 11 metal. Rhenium is typically present in a quantity of at most 25 mmole/kg, preferably at most 15 mmole/kg, more preferably at most 10 mmole/kg, in particular at most 7.5 mmole/kg, on the same basis.

Further, when the epoxidation catalyst comprises a rhenium containing promoter component, the catalyst may preferably comprise a rhenium copromoter, as a further component deposited on the carrier. Suitably, the rhenium copromoter may be selected from components comprising an element selected from tungsten, chromium, molybdenum, sulfur, phosphorus, boron, and mixtures thereof. Preferably, the rhenium copromoter is selected from components comprising tungsten, chromium, molybdenum, sulfur, and mixtures thereof. It is particularly preferred that the rhenium copromoter comprises, as an element, tungsten.

The rhenium copromoter may typically be present in a total quantity of at least 0.05 mmole/kg, more typically at least 0.5 mmole/kg, and preferably at least 2.5 mmole/kg, calculated as the element (i.e. the total of tungsten, chromium, molybdenum, sulfur, phosphorus and/or boron), relative to the weight of Group 11 metal. The rhenium copromoter may be present in a total quantity of at most 200 mmole/kg, preferably at most 50 mmole/kg, more preferably at most 25 mmole/kg, on the same basis. The form in which the rhenium copromoter may be deposited is not material to the invention. For example, it may suitably be provided as an oxide or as an oxyanion, for example, as a sulfate, borate or molybdate, in salt or acid form.

The epoxidation catalyst preferably comprises Group 11 metal, the promoter component, and a component comprising a further element. Eligible further elements may be selected from the group of nitrogen, fluorine, alkali metals, alkaline earth metals, titanium, hafnium, zirconium, vanadium, thallium, thorium, tantalum, niobium, gallium and germanium and mixtures thereof. Preferably the alkali metals are selected from lithium, potassium, rubidium and cesium. Most preferably the alkali metal is lithium, potassium and/or cesium. Preferably the alkaline earth metals are selected from calcium and barium. Typically, the further element is present in the epoxidation catalyst in a total quantity of from 0.05 to 2500 mmole/kg, more typically from 0.25 to 500 mmole/kg, calculated as the element on the weight of Group 11 metal. The further elements may be provided in any form. For example, salts of an alkali metal or an alkaline earth metal are suitable.

As used herein, the quantity of alkali metal present in the epoxidation catalyst is deemed to be the quantity insofar as it can be extracted from the epoxidation catalyst with de-ionized water at 100° C. The extraction method involves extracting a 10-gram sample of the catalyst three times by heating it in 20 ml portions of de-ionized water for 5 minutes at 100° C. and determining in the combined extracts the relevant metals by using a known method, for example atomic absorption spectroscopy.

As used herein, the quantity of alkaline earth metal present in the epoxidation catalyst is deemed to the quantity insofar as it can be extracted from the epoxidation catalyst with 10% w nitric acid in de-ionized water at 100° C. The extraction method involves extracting a 10-gram sample of the catalyst by boiling it with a 100 ml portion of 10% w nitric acid for 30 minutes (1 atm., i.e. 101.3 kPa) and determining in the combined extracts the relevant metals by using a known method, for example atomic absorption spectroscopy. Reference is made to U.S. Pat. No. 5,801,259, which is incorporated herein by reference.

Methods for depositing Group 11 metal, the one or more promoter components and the one or more component comprising a further element on a carrier material are known in the art and such methods may be applied in the practice of this invention. Reference may be made to U.S. Pat. No. 5,380,697, U.S. Pat. No. 5,739,075, EP-A-266015, and U.S. Pat. No. 6,368,998, which are incorporated herein by reference. Suitably, the methods include impregnating the particulate carrier materials with a liquid mixture comprising cationic Group 11 metal-amine complex and a reducing agent.

In some embodiments, the invention provides processes for the epoxidation of an olefin comprising reacting a feed comprising the olefin and oxygen in the presence an epoxidation catalyst, as described hereinbefore, contained in one or more process microchannels of a microchannel reactor.

The olefin for use in the present invention may be an aromatic olefin, for example styrene, or a di-olefin, whether conjugated or not, for example 1,9-decadiene or 1,3-butadiene. A mixture of olefins may be used. Typically, the olefin is a monoolefin, for example 2-butene or isobutene. Preferably, the olefin is a mono-α-olefin, for example 1-butene or propylene. The most preferred olefin is ethylene.

The feed for the epoxidation process of this invention comprises the olefin and oxygen. As used herein, the feed to a process is understood to represent the total of reactants and other components which is fed to the section of the process microchannels in which the process in question takes place. Some of the feed components may be fed to the epoxidation process through an opening in upstream end 220 of process microchannels 210. Some of the feed components may be fed through first feed channel 260 and one or more first orifices 280. For example, an olefin rich feed component may be fed through the opening in the upstream end of the process microchannels and an oxygen rich feed component may be fed through the first feed channel and the one or more first orifices. Alternatively, the oxygen rich feed component may be fed through the opening in the upstream end of the process microchannels and the olefin rich feed component may be fed through the first feed channel and the one or more first orifices. Certain feed components may be fed through the opening in the upstream end of the process microchannels and through the first feed channel and the one or more first orifices. For example, the olefin may be fed partly through the opening in the upstream end of the process microchannels and partly through the first feed channel and the one or more first orifices. As another example, oxygen may be fed partly through the opening in the upstream end of the process microchannels and partly through the first feed channel and the one or more first orifices.

In an embodiment, an oxygen rich feed component may be contacted within the process microchannels with an olefin rich feed component. The oxygen rich feed component is typically relatively lean in the olefin. The oxygen rich feed component may comprise oxygen typically in a quantity of at least 5 mole-%, in particular at least 10 mole-%, more in particular at least 15 mole-%, relative to the total oxygen rich feed component, and typically in a quantity of at most 100 mole-%, or at most 99.9 mole-%, or at most 99.8 mole-%, relative to the total oxygen rich feed component. The oxygen rich feed component may comprise the olefin typically in a quantity of at most 5 mole-%, in particular at most 1 mole-%, relative to the total oxygen rich feed component. Such oxygen rich feed component may normally be outside the explosion limits. The olefin rich feed component is typically relatively lean in oxygen. The olefin rich feed component may comprise the olefin typically in a quantity of at least 20 mole-%, in particular at least 25 mole-%, more in particular at least 30 mole-%, relative to the total olefin rich feed component, and typically in a quantity of at most 100 mole-%, or at most 99.99 mole-%, or at most 99.98 mole-%, relative to the total olefin rich feed component. The olefin rich feed component may comprise oxygen typically in a quantity of at most 15 mole-%, in particular at most 10 mole-%, more in particular at most 5 mole-%, relative to the total olefin rich feed component. Such olefin rich feed component may normally be outside the explosion limits.

In the case that there is a plurality of first orifices 280, one or more first orifices 280 positioned downstream of another first orifice 280, converted reactant may be substantially replenished. For example, replenishing converted oxygen may effect that the concentration of oxygen in the feed can be maintained substantially constant along the length of the epoxidation catalyst, which may favor substantially complete conversion of the olefin. Alternatively, the concentration of the olefin may be kept substantially constant by replenishing converted olefin, which may favor substantially complete conversion of oxygen.

Further, in an aspect of the invention, by feeding the olefin rich feed component and the oxygen rich feed component through different channels and mixing the feed components in the process microchannels effects, feed compositions can be accomplished within the process microchannels, while outside the process microchannels such feed compositions could lead to an explosion.

An organic halide may be present in the feed as a reaction modifier for increasing the selectivity, suppressing the undesirable oxidation of the olefin or the olefin oxide to carbon dioxide and water, relative to the desired formation of the olefin oxide. The organic halide may be fed as a liquid or as a vapor. The organic halide may be fed separately or together with other feed components through an opening in upstream end 220 of the process microchannels 210 or through first feed channel 260 and one or more first orifices 280. An aspect of feeding the organic halide through a plurality first orifices is that there may be an increase in the level of the quantity of the organic halide along the length of the epoxidation catalyst, by which the activity and/or selectivity of the epoxidation catalyst can be manipulated in accordance with the teachings of EP-A-352850, which is incorporated herein by reference. For example, when using a rhenium containing epoxidation catalyst, the activity of the epoxidation catalyst can be enhanced along the length of the epoxidation catalyst. This could allow for better utilization of the epoxidation catalyst in regions where oxygen or the olefin is depleted relative to the regions where oxygen and the olefin are fed.

Organic halides are in particular organic bromides, and more in particular organic chlorides. Preferred organic halides are chlorohydrocarbons or bromohydrocarbons. More preferably they are selected from the group of methyl chloride, ethyl chloride, ethylene dichloride, ethylene dibromide, vinyl chloride or a mixture thereof. Most preferred are ethyl chloride and ethylene dichloride.

In addition to an organic halide, an organic or inorganic nitrogen compound may be employed as reaction modifier, but this is generally less preferred. It is considered that under the operating conditions of the epoxidation process the nitrogen containing reaction modifiers are precursors of nitrates or nitrites (cf. e.g. EP-A-3642 and U.S. Pat. No. 4,822,900, which are incorporated herein by reference). Organic nitrogen compounds and inorganic nitrogen compounds may be employed. Suitable organic nitrogen compounds are nitro compounds, nitroso compounds, amines, nitrates and nitrites, for example nitromethane, 1-nitropropane or 2-nitropropane. Suitable inorganic nitrogen compounds are, for example, nitrogen oxides, hydrazine, hydroxylamine or ammonia. Suitable nitrogen oxides are of the general formula $NO_x$ wherein x is in the range of from 1 to 2, and include for example NO, $N_2O_3$ and $N_2O_4$.

The organic halides and the organic or inorganic nitrogen compounds are generally effective as reaction modifier when used in low total concentration, for example up to 0.01 mole-%, relative to the total feed. It is preferred that the organic halide is present at a concentration of at most $50 \times 10^{-4}$ mole-%, in particular at most $20 \times 10^{-4}$ mole-%, more in particular at most $15 \times 10^{-4}$ mole-%, relative to the total feed, and preferably at least $0.2 \times 10^{-4}$ mole-%, in particular at least $0.5 \times 10^{-4}$ mole-%, more in particular at least $1 \times 10^{-4}$ mole-%, relative to the total feed.

In addition to the olefin, oxygen and the organic halide, the feed may additionally comprise one or more further components, for example saturated hydrocarbons, as ballast gas, inert gases and carbon dioxide. The one or more further components may be fed separately or together with other feed components through an opening in upstream end 220 of the process microchannels 210 or through first feed channel 260 and one or more first orifices 280.

The olefin concentration in the feed may be selected within a wide range. Typically, the olefin concentration in the feed will be at most 80 mole-%, relative to the total feed. Preferably, it will be in the range of from 0.5 to 70 mole-%, in particular from 1 to 60 mole-%, on the same basis.

The oxygen concentration in the feed may be selected within a wide range. Typically, the concentration of oxygen applied will be within the range of from 1 to 15 mole-%, more typically from 2 to 12 mole-% of the total feed.

The saturated hydrocarbons comprise, for example, methane and ethane. Unless stated herein otherwise, saturated hydrocarbons may be present in a quantity of up to 80 mole-%, in particular up to 75 mole-%, relative to the total feed, and frequently they are present in a quantity of at least 30 mole-%, more frequently at least 40 mole-%, on the same basis.

Carbon dioxide may be present in the feed as it is formed as a result of undesirable oxidation of the olefin and/or the olefin oxide, and it may accordingly be present in feed components present in a recycle stream. Carbon dioxide generally has an adverse effect on the catalyst activity. Advantageously, the quantity of carbon dioxide is, for example, below 2 mole-%, preferably below 1 mole-%, or in the range of from 0.2 to 1 mole-%, relative to the total feed.

The inert gases include, for example nitrogen or argon. Unless stated herein otherwise, the inert gases may be present in the feed in a concentration of from 30 to 90 mole-%, typically from 40 to 80 mole-%.

The epoxidation process of this invention may be air-based or oxygen-based, see "Kirk-Othmer Encyclopedia of Chemical Technology", $3^{rd}$ edition, Volume 9, 1980, pp. 445-447. In the air-based process air or air enriched with oxygen is employed as the source of the oxidizing agent while in the oxygen-based processes high-purity (at least 95 mole-%) oxygen is employed as the source of the oxidizing agent. Presently most epoxidation plants are oxygen-based and this is preferred in the practice of certain embodiment of this invention. It is an advantage of other embodiments of this invention that air may be fed to the process as the source of the oxidizing agent.

The epoxidation process may be carried out using reaction temperatures selected from a wide range. Preferably the reaction temperature is in the range of from 150 to 340° C., more preferably in the range of from 180 to 325° C. Typically, the heat transfer liquid present in the first heat exchange channels may have a temperature which is typically 0.5 to 10° C. lower than the reaction temperature.

As disclosed herein before, during use, the epoxidation catalysts may be subject to a performance decline. In order to reduce effects of an activity decline, the reaction temperature may be increased gradually or in a plurality of steps, for example in steps of from 0.1 to 20° C., in particular 0.2 to 10° C., more in particular 0.5 to 5° C. The total increase in the reaction temperature may be in the range of from 10 to 140° C., more typically from 20 to 100° C. The reaction temperature may be increased typically from a level in the range of from 150 to 300° C., more typically from 200 to 280° C., when a fresh epoxidation catalyst or rejuvenated epoxidation catalyst is used, to a level in the range of from 230 to 340° C., more typically from 240 to 325° C., when the epoxidation catalyst has decreased in activity.

The epoxidation process is preferably carried out at a pressure, as measured at upstream 220 end of the process microchannels 210, in the range of from 1000 to 3500 kPa.

The olefin oxide leaving the section of the process microchannels containing the epoxidation catalyst is comprised in a reaction mixture which may further comprise unreacted olefin, unreacted oxygen, and other reaction products such as carbon dioxide. Typically, the content of olefin oxide in the reaction product is in general in the range of from 1 to 25 mole-%, more typically from 2 to 20 mole-%, in particular from 2 to 5 mole-%.

In an embodiment, the invention provides a process for the epoxidation of an olefin comprising reacting a feed comprising the olefin and oxygen in a total quantity of at least 50 mole-%, relative to the total feed, in the presence an epoxidation catalyst contained in one or more process microchannels of a microchannel reactor. In this embodiment, the olefin and oxygen may be present in the feed in a total quantity of at least 80 mole-%, in particular at least 90 mole-%, more in particular at least 95 mole-%, relative to the total feed, and typically up to 99.5 mole-%, in particular up to 99 mole-%, relative to the total feed. The molar ratio of olefin to oxygen may be in the range of from 3 to 100, in particular from 4 to 50, more in particular from 5 to 20. The saturated hydrocarbons and the inert gases may be substantially absent. As used herein, in this context "substantially absent" means that the quantity of saturated hydrocarbons in the feed is at most 10 mole-%, in particular at most 5 mole-%, more in particular at most 2 mole-%, relative to the total feed, and that the quantity of inert gases in the feed is at most 10 mole-%, in particular at most 5 mole-%, more in particular at most 2 mole-%, relative to the total feed. In this particular embodiment, process conditions may be applied such that the quantity of olefin oxide in the epoxidation reaction mixture is in the range of from 4 to 15 mole-%, in particular from 5 to 12 mole-%, for example from 6 to 10 mole-%. Preferably, the epoxidation reaction mixture, including the olefin oxide, is quenched, as described herein.

In an embodiment, the invention provides a process for the epoxidation of an olefin comprising reacting a feed comprising the olefin and oxygen in the presence an epoxidation catalyst contained in one or more process microchannels of a microchannel reactor, and applying conditions for reacting the feed such that the conversion of the olefin or the conversion of oxygen is at least 90 mole-%. The conversion of the olefin may be at least 90 mole-% and the conversion of oxygen may be at least 90 mole-%. In particular, in this embodiment, the feed may comprise the olefin and oxygen in a quantity of at most 50 mole-%, relative to the total feed, and the feed may additionally comprise saturated hydrocarbons, as ballast gas, and inert gas. Typically, process conditions are applied such that the conversion of the olefin or the conversion of oxygen is at least 95 mole-%, in particular at least 98 mole-%, more in particular at least 99 mole-%. As used herein, the conversion is the quantity of a reactant converted relative to the quantity of the reactant in the feed, expressed in mole-%. Preferably, the conversion of the olefin is at least 95 mole-%, in particular at least 98 mole-%, more in particular at least 99 mole-% and oxygen may be at least partly replenished. The presence of an excess of oxygen in the feed, relative to the olefin, assists in achieving a high conversion of the olefin. For example, the molar ratio of oxygen over the olefin in the feed may be at least 1.01, typically at least 1.05, in particular at least 1.1, more in particular at least 1.2; and for example at most 5, in particular at most 3, more in particular at most 2. In this embodiment, a relatively high selectivity in the conversion of the olefin into the olefin oxide is achieved. A used herein, the selectivity is the quantity of olefin oxide formed, relative to the quantity of olefin converted, expressed in mole-%. Moreover, such high conversion of the olefin enables that the process may be carried out economically in a once-through mode, which means that no recycle of unconverted reactants is applied, and that air may be fed to the epoxidation process, which means effectively that the need of an air separation unit is eliminated.

In the practice of this invention, the reaction product, including the olefin oxide, may be quenched by heat exchange with a heat exchange fluid. The quenching may be conducted in second section 340 of process microchannels 210 by heat exchange with heat exchange fluid present in one or more second heat exchange channels 350. Typically, the temperature of the reaction product, including the olefin oxide, may be decreased to a temperature of at most 250° C., more typically at most 225° C., preferably in the range of from 20 to 200° C., more preferably 50 to 190° C., in particular from 80 to 180° C. The quenching may result in a reduction in temperature in the range of from 50 to 200° C., in particular from 70 to 160° C. Quenching enables increasing the total quantity of the olefin oxide and oxygen in the feed of the epoxidation process, and eliminating the ballast gas or reducing the quantity of ballast gas in the feed of the epoxidation process. Also, a result of quenching is that the olefin oxide produced is a cleaner product, comprising less aldehyde and carboxylic acid impurities.

In some embodiments, the invention provides a process for the epoxidation of an olefin comprising reacting a feed comprising an olefin and oxygen in the presence of an epoxidation catalyst to thereby form a first mixture comprising the olefin oxide and carbon dioxide, as described hereinbefore, quenching the first mixture, typically by heat exchange with a heat exchange fluid or by mixing with a fluid, and converting the quenched first mixture to form a second mixture comprising the olefin oxide and a 1,2-carbonate. An advantage of the processes in accordance with these particular embodiments is that a reduction is achieved in the complexity of the handling of product streams and recycle streams, compared to the handling of such streams in a conventional olefin epoxidation process, because it eliminates the need for, for example, an olefin oxide recovering unit and a carbon dioxide removal unit. Reaction conditions and types of catalysts as described herein may be employed, on the understanding that the catalysts may be in particulate form or in the form of well known, shaped bodies. Without compromising these advantages, a reactor other than a microchannel reactor may be employed, and the steps of the process may be performed in more than one piece of equipment. For example, one or more microchannel reactors, shell-and-tube heat exchanger reactors, stirred tank reactors, bubble columns or condensation apparatus may be employed instead of, or in addition to, a microchannel reactor. The present invention therefore encompasses the use of such other types of reactors or condensation apparatus, or the use of a plurality of reactors or condensation apparatus in these processes. On the other hand, there is a preference to benefit additionally from the advantages of employing in these processes a microchannel reactor having process microchannels, as described herein. Therefore, preferably, the invention provides a process for the epoxidation of an olefin comprising reacting a feed comprising an olefin and oxygen in the presence of an epoxidation catalyst contained in a first section 240 of one or more process microchannels 210 of a microchannel reactor to thereby form a first mixture comprising the olefin oxide and carbon dioxide, as described hereinbefore, quenching the first mixture in intermediate section 440 of the one or more process microchannels 210 positioned downstream of first section 240 by heat exchange with a heat exchange fluid, in a same manner as described hereinbefore, and converting in second section 340 of the one or more process microchannels 210 positioned downstream of intermediate section 440 the quenched first mixture to form a second mixture comprising the olefin oxide and a 1,2-carbonate.

The conversion of the quenched first mixture comprising the olefin oxide and carbon dioxide to form the second mixture comprising the olefin oxide and a 1,2-carbonate typically involves reacting at least a portion of the olefin oxide present in the first mixture with at least a portion of the carbon dioxide present in the first mixture to form the 1,2-carbonate. Typically, carbon dioxide present in the first mixture is carbon dioxide co-formed in the epoxidation reaction. The molar quantity of carbon dioxide present in the first mixture may be in the range of from 0.01 to 1 mole, in particular 0.02 to 0.8 mole, more in particular 0.05 to 0.6 mole-%, per mole of the olefin oxide present in the first mixture. Reaction conditions, catalysts and further methods suitable for the conversion of the olefin oxide with carbon dioxide are as disclosed hereinafter. Typically, at least 50 mole-%, in particular at least 80 mole-%, more in particular at least 90 mole-% of the carbon dioxide is converted, for example at least 98 mole-%, and in the practice of this invention, frequently at most 99.9 mole-% is converted. Additional carbon dioxide may be fed to the second section, but that is frequently not a preferred embodiment.

In this embodiment, in cases that the second mixture is formed as a gaseous phase, the process may additionally comprise condensing at least a portion of the second mixture comprising the olefin oxide and the 1,2-carbonate in a third section of the one or more process microchannels, which third section is positioned downstream of the second section. Typically, condensing at least a portion of the second mixture involves removal of heat by heat exchange with a heat exchange fluid. Such heat exchange fluid may be present in a fourth heat exchange channel, as described hereinbefore. Typically, at least 50 mole-%, in particular at least 80 mole-%, more in particular at least 90 mole-% of the total of the olefin oxide and the 1,2-carbonate present in the second mixture is condensed, for example at least 98 mole-%, and in the practice of this invention, frequently at most 99.9 mole-% is condensed. Preferably, in cases that the second mixture comprises water at least partly as a gaseous phase, the process may additionally comprise condensing at least a portion of such water present in the second mixture in the third section. Typically, water present in the second mixture, if any, is water co-formed in the epoxidation reaction. The molar quantity of water present in the second mixture may be in the range of from 0.01 to 1 mole, in particular 0.02 to 0.8 mole, more in particular 0.05 to 0.6 mole-%, per mole of the total quantities of the olefin oxide and the 1,2-carbonate present in the second mixture. Typically, at least 50 mole-%, in particular at least 80 mole-%, more in particular at least 90 mole-% of the total of the water present in the second mixture is condensed, for example at least 98 mole-%, and in the practice of this invention, frequently at most 99.9 mole-% is condensed.

As described hereinbefore, during the operation of the epoxidation process, the epoxidation catalyst is subject to a performance decline. The epoxidation catalyst may be removed from the process microchannel by blowing with a suitable gas, for example, air, nitrogen, argon or carbon dioxide, either in the normal downstream direction, or in back-flow. A support device, if applied, may be removed from the process microchannels, prior to removing the epoxidation catalyst.

In accordance with an embodiment of the invention, the epoxidation catalyst may be rejuvenated by a method which comprises washing the catalyst with an aqueous liquid, and depositing one or more promoter components on the washed catalyst.

The aqueous liquid which may be used in rejuvenating the epoxidation catalyst may be, for example water or an aqueous organic diluent, such as for example, a mixture of water and methanol ethanol, propanol, isopropanol, tetrahydrofuran, ethylene glycol, ethylene glycol dimethyl ether, diethylene glycol dimethyl ether, dimethylformamide, acetone, or methyl ethyl ketone. Washing may be carried out at an elevated temperature, for example at a temperature from 30 to 100° C., or 35 to 95° C. The washing may comprise contacting the epoxidation catalyst with the aqueous liquid for a period of time, for example up to 10 hours, in particular from 0.25 to 5 hours, and removing the liquid together with materials leached form the epoxidation catalyst into the liquid. The washing may be repeated, for example two or three times, until there is no change in the composition of the effluent. The effluent may be treated and/or separated and/or purified, such that the any Group 11 metal and any promoter components present in the effluent may be reused, as a promoter component, or for any other use. For example, rhenium, if present as a promoter component, may be recovered from the effluent as a perrhenate, or as the corresponding acid, by separation methods involving exchange resins.

The one or more promoter components may be deposited on the washed catalyst by the methods described hereinbefore. The one or more promoter components and their quantities may be as described hereinbefore. In addition to one or more promoter components, one or more components comprising one or more further elements may be deposited on the washed catalyst prior to, together with or subsequent to the deposition of the promoter components, by using any of the methods described hereinbefore. Particulars of the components comprising the further elements, including suitable quantities thereof, are disclosed hereinafter. If desirable, in addition to one or more promoter components, Group 11 metal may be deposited on the washed carrier, by using any of the methods described hereinbefore, in order to adjust the desired quantity of Group 11 metal content of the epoxidation catalyst, or to compensate for a loss of Group 11 metal. After completing the rejuvenation, a feed comprising the olefin and oxygen may be reacted in the presence of the rejuvenated catalyst, according to the methods described hereinbefore.

The inventive method of rejuvenating the epoxidation catalyst is in particular directed to restoring at least partly the performance level, in particular activity and/or selectivity, which the epoxidation catalyst had before it was used in an epoxidation process. The inventive method of rejuvenating the epoxidation catalyst may be applied after the epoxidation catalyst has been used again following an earlier rejuvenation.

The inventive method of rejuvenating an epoxidation catalyst may be applicable with the epoxidation catalyst present in any reactor suitable for the epoxidation of an olefin. Examples of such reactors are reactors in the form of shell-and-tube heat exchangers and microchannel reactors. It is an advantageous aspect of the invention that during the rejuvenation the epoxidation catalyst may be present in the epoxidation reactor, in particular in the reaction tubes of the shell-and-tube heat exchanger reactor, which eliminates the need of removing the epoxidation from the epoxidation reactor and the catalyst may stay in place after the rejuvenation for use during a further period of production of the olefin oxide from the olefin and oxygen. In particular, it is an advantageous aspect of this invention that during the rejuvenation the epoxidation catalyst may be present in the first section of the one or more process microchannels and may stay there after the rejuvenation for use during a further period of production of the olefin oxide from the olefin and oxygen.

The epoxidation reaction mixture, including the olefin oxide, may be withdrawn from the process microchannel and the microchannel reactor and be processed in the conventional manner, using conventional methods and conventional equipment. A separation system may provide for the separation of the olefin oxide from any unconverted olefin, any unconverted oxygen, any ballast gas and carbon dioxide. An aqueous extraction fluid such as water may be used to separate these components. The enriched extraction fluid containing the olefin oxide may be further processed for recovery of the olefin oxide. The olefin oxide produced may be recovered from the enriched extraction fluid, for example by distillation or extraction. A mixture which comprises any unconverted olefin, any unconverted oxygen, any ballast gas and carbon dioxide and which is lean in olefin oxide may be extracted to at least partly remove carbon dioxide. The resulting carbon dioxide lean mixture may be recompressed, dried and recycled as a feed component to the epoxidation process of this invention.

The olefin oxide produced in the epoxidation process of the invention may be converted by conventional methods into a 1,2-diol, a 1,2-diol ether, a 1,2-carbonate or an alkanol amine.

The conversion into the 1,2-diol or the 1,2-diol ether may comprise, for example, reacting the ethylene oxide with water, in a thermal process or by using a catalyst, which may be an acidic catalyst or a basic catalyst. For example, for making predominantly the 1,2-diol and less 1,2-diol ether, the olefin oxide may be reacted with a ten fold molar excess of water, in a liquid phase reaction in presence of an acid catalyst, e.g. 0.5-1.0% w sulfuric acid, based on the total reaction mixture, at 50-70° C. at 100 kPa absolute, or in a gas phase reaction at 130-240° C. and 2000-4000 kPa absolute, preferably in the absence of a catalyst. The presence of such a large quantity of water may favor the selective formation of 1,2-diol and may function as a sink for the reaction exotherm, helping controlling the reaction temperature. If the proportion of water is lowered the proportion of 1,2-diol ethers in the reaction mixture is increased. The 1,2-diol ethers thus produced may be a di-ether, tri-ether, tetra-ether or a subsequent ether. Alternative 1,2-diol ethers may be prepared by converting the olefin oxide with an alcohol, in particular a primary alcohol, such as methanol or ethanol, by replacing at least a portion of the water by the alcohol.

The olefin oxide may be converted into the corresponding 1,2-carbonate by reacting it with carbon dioxide. If desired, a 1,2-diol may be prepared by subsequently reacting the 1,2-carbonate with water or an alcohol to form the 1,2-diol. For applicable methods, reference is made to U.S. Pat. No. 6,080, 897, which is incorporated herein by reference.

The conversion into the alkanol amine may comprise reacting the olefin oxide with an amine, such as ammonia, an alkyl amine or a dialkyl amine. Anhydrous or aqueous ammonia may be used. Anhydrous ammonia is typically used to favor the production of mono alkanol amine. For methods applicable in the conversion of the olefin oxide into the alkanol amine, reference may be made to, for example U.S. Pat. No. 4,845,296, which is incorporated herein by reference.

In an embodiment, the invention provides a process for the preparation of a 1,2-diol, a 1,2-diol ether, a 1,2-carbonate or an alkanol amine, which process comprises reacting a feed comprising an olefin and oxygen in the presence an epoxidation catalyst contained in a first section of one or more process microchannels of a microchannel reactor, which may be accomplished as described hereinbefore, and converting the olefin oxide with water, an alcohol, carbon dioxide or an amine to form the 1,2-diol, 1,2-diol ether, 1,2-carbonate or alkanol amine in a second section of the one or more process microchannels positioned downstream of the first section.

The invention also provides a reactor which is suitable for the inventive process for the preparation of a 1,2-diol, a 1,2-diol ether, a 1,2-carbonate or an alkanol amine. Accordingly, an embodiment of the invention provides a reactor suitable for the preparation of a 1,2-diol, a 1,2-diol ether or an alkanol amine, which reactor is a microchannel reactor comprising one or more process microchannels comprising
an upstream end,
a downstream end,
a first section, as described hereinbefore, which is adapted to n epoxidation catalyst, to receive a feed comprising an olefin and oxygen, and to cause conversion of at least a portion of the feed to form an olefin oxide in the presence of the epoxidation catalyst, and
a second section positioned downstream of the first section which is adapted to receive the olefin oxide; to receive water, an alcohol, carbon dioxide or an amine; and to cause conversion of the olefin oxide to form the 1,2-diol, 1,2-diol ether, 1,2-carbonate or alkanol amine.

The conversion of the olefin oxide with water, an alcohol, carbon dioxide or an amine in the second section of the one or more process microchannels may be a thermal conversion, or a conversion which is catalyzed by using a suitable catalyst. Suitable catalysts are, for example, acid catalysts and basic catalysts. Acidic catalysts are, for example, strongly acid ion exchange resins, such as, for example, those comprising sulfonic acid groups on a styrene/divinylbenzene copolymer matrix. Other suitable acid catalysts are, for example, silicas and oxides of metals selected from Groups 3-6 of the Periodic Table of the Elements, for example, zirconium oxide and titanium oxide. Basic catalysts are, for example, strong basic ion exchange resins such as, for example, those comprising quaternary phosphonium or quaternary ammonium groups on a styrene/divinylbenzene copolymer matrix. Such catalysts are known in the art, for example from EP-A-156449, U.S. Pat. No. 4,982,021, U.S. Pat. No. 5,488,184. U.S. Pat. No. 6,153,801 and U.S. Pat. No. 6,124,508, which are incorporated herein by reference, and/or they are commercially available. Suitable catalysts may represent themselves as a liquid under the conditions of the reaction, for example mineral acids, such as, for example, sulfuric acid and phosphoric acid, and such catalysts as known from JP-A-56-092228, which is incorporated herein by reference.

Suitable catalysts for the conversion of the olefin oxide with carbon dioxide may be, for example, resins which comprise quaternary phosphonium halide groups or quaternary ammonium halide groups on a styrene/divinylbenzene copolymer matrix, wherein the halide may be in particular chloride or bromide. Such catalysts for this conversion are known from T. Nishikubo, A. Kameyama, J. Yamashita and M. Tomoi, Journal of Polymer Science, Pt. A. Polymer Chemist, 31, 939-947 (1993), which is incorporated herein by reference. More suitable catalysts comprise a metal salt immobilized in a solid carrier, wherein the metal salt may comprise a cation of a metal selected from those in the third Period and Group 2, the fourth Period and Groups 2 and 4-12, the fifth Period and Groups 2, 4-7, 12 and 14, and the sixth Period and Groups 2 and 4-6, of the Periodic Table of the Elements, and wherein the carrier contains a quaternary ammonium, quaternary phosphonium, quaternary arsenonium, quaternary stibonium or a quaternary sulfonium cation, which cation may be separated from the backbone of the carrier by a spacer group of the general formula $-(CH_2-O-)_m-(CH_2)_n-$, m and n being integers, with for example n being at most 10, for example 1, 2, 3 or 6, when m is 0, and n being from 1 to 8, for example 2 or 4, when m is 1. The metal salt may be selected in particular from the halides, acetates, laureates, nitrates and sulfates of one or more selected from magnesium, calcium, zinc, cobalt, nickel, manganese, copper and tin, for example zinc bromide, zinc iodide, zinc acetate, or cobalt bromide. The solid carrier for immobilizing the metal salt may be, for example silica, a silica-alumina, or a zeolite, or it may be a resin with a polystyrene/divinylbenzene copolymer backbone, or a silica-based polymeric backbone, such as in polysiloxanes, or a resin incorporating quaternized vinylpyridine monomers. Other suitable catalysts for the conversion of the olefin oxide with carbon dioxide are, for example, quaternary phosphonium halides, quaternary ammonium halides, and certain metal halides. An example is methyltributylphosphonium iodide. More suitably, the catalysts comprise an organic base neutralized with a hydrogen halide, wherein the organic base has a $pK_a$ greater than 8 and comprises a carbon-based compound containing one or more nitrogen and/or phosphorus atoms with at least one free electron pair. The hydrogen halide may be hydrogen bromide or hydrogen iodide. Examples of such organic bases having a $pK_a$ greater than 8 are 2-tert-butylimino-2-diethylamino-1,3-dimethylperhydro-1,3,2-diazaphosphorin, as such or on polystyrene, 1,1,3,3-tetramethylguanidine, and triethanolamine. In this context, the term "neutralized" means that the organic base and the hydrogen halide have reacted in amounts relative to each other such that an aqueous solution of the reaction product would be essentially neutral, i.e. having a pH between 6 and 8.

Another suitable catalyst for the conversion of the olefin oxide with carbon dioxide comprises from 10 to 90 mole-%, based on the mixture, of an organic base and from 10 to 90 mole-%, based on the mixture, of the salt of the organic base and a hydrogen halide, wherein the organic base comprises a carbon-based compound containing one or more nitrogen and/or phosphorus atoms with at least one free electron pair, and has a $pK_a$ high enough that it is capable of binding carbon dioxide under the reaction conditions. The hydrogen halide may be hydrogen bromide or hydrogen iodide. Examples of such organic bases having capability of binding carbon dioxide are 2-tert-butylimino-2-diethylamino-1,3-dimethylperhydro-1,3,2-diazaphosphorin, as such or on polystyrene, 1,1, 3,3-tetramethylguanidine, and triethanolamine. An exemplary catalyst may be based upon 1,1,3,3-tetramethylguanidine, hydrogen iodide and molybdenum trioxide in a mole ratio of about 6.6:4.71:1. When using these catalysts in the presence of water and carbon dioxide, the formed 1,2-carbonate may be at least partly converted in situ to the corresponding 1,2-glycol.

The catalyst, when present as a solid material under the condition of the reaction, may be installed in the second section of the one or more process microchannels by known methods and applicable methods include, for example, filling at least a portion of the second section to form a packed bed, or covering at least a portion of the walls of the second section with the catalyst, for example by wash coating. Some of the methods related to the installation of an epoxidation catalyst, as set out hereinbefore, may be applicable to these catalysts in an analogous manner. The use of a catalyst which is present as a solid material under the condition of the reaction is less preferred. In embodiments in which the catalyst represents itself as a liquid under the conditions of the reaction, the catalyst may be fed to the second section of the one or more process microchannels through the second feed channel and the one or more second orifices, suitably together with feed comprising water, the alcohol, carbon dioxide and/or the amine. When the conversion is a thermal conversion, the temperature may be in the range of from 100 to 300° C., in particular from 150 to 250° C. When the conversion is a catalytic conversion, the temperature may be in the range of from 30 to 200° C., in particular from 50 to 150° C. The molar ratio of the total of water, the alcohol, carbon dioxide and the amine to the olefin oxide may be more than 10, for example at most 20 or at most 30. However, as described hereinbefore, it is a benefit of this invention that adequate control of the temperature can be achieved when the molar ratio of the total of water, the alcohol, carbon dioxide and the amine is kept relatively low, albeit that the selectivity to the desired product may become lower. The molar ratio of the total of water, the alcohol, carbon dioxide and the amine to the olefin oxide may be at most 10, in particular in the range of from 1 to 8, more in particular from 1.1 to 6, for example from 1.2 to 4. The feed fed to the second section of the process microchannels may comprise a total quantity of the olefin oxide and water, the alcohol, carbon dioxide and the amine of at least 60% w, in particular at least 80% w, more in particular at least 90% w, for example at least 95% w, relative to the total weight of the said feed. The pressure may be in the range of from 500 to 3500 kPa, as measured at the second feed channel, described hereinbefore. The reaction conditions may be selected such that the conversion of the olefin oxide is at least 50 mole-%, in particular at least 80 mole-%, more in particular at least 90 mole-%, for example at least 95 mole-%. Suitable alcohols for the conversion of the olefin oxide may be methanol, ethanol, propanol, isopropanol, 1-butanol and 2-butanol. Methanol is a preferred alcohol. Mixtures of alcohols and mixtures of water and one or more alcohols may be used. Suitable amines for the conversion of the olefin oxide into alkanol amine may be ammonia or a primary amine or a secondary amine. Suitable primary amines are, for example, methylamine, ethylamine, 1-propylamine, 2-propylamine and 1-butylamine. Suitable secondary amines are, for example, dimethylamine, diethylamine, ethylmethylamine, methyl(1-propyl)amine, di(2-propyl)amine and di(1-butyl)amine. Mixtures of alcohols, mixtures of amines and mixtures of water and one or more alcohols or one or more amines may be used.

The temperature of the epoxidation reaction mixture, including the olefin oxide, may be controlled before the olefin oxide enters the second section of the one or more process microchannels, so that the olefin oxide may adopt the desired temperature for the conversion to the 1,2-diol, the 1,2-diol ether, the 1,2-carbonate or the alkanol amine. Thus, the one or more process microchannels may comprise additionally an intermediate section downstream from the first section and upstream from the second section, which intermediate section is adapted to control the temperature of the olefin oxide. In particular, the reactor may comprise additionally one or more third heat exchange channels adapted to exchange heat with the intermediate section of the said process microchannels.

In an embodiment, the invention provides a process for the preparation of a 1,2-diol, which process comprises reacting a feed comprising an olefin and oxygen in the presence an epoxidation catalyst contained in a first section of one or more process microchannels of a microchannel reactor, which may be accomplished as described hereinbefore, converting the olefin oxide with carbon dioxide to form a 1,2-carbonate in a second section of the one or more process microchannels positioned downstream of the first section, and converting the 1,2-carbonate with water or an alcohol to form the 1,2-diol in a third section of the one or more process microchannels positioned downstream of the second section.

The invention also provides a reactor which suitable for the inventive process for the preparation of a 1,2-diol. Accordingly, an embodiment of the invention provides a reactor suitable for the preparation of a 1,2-diol, which reactor is a microchannel reactor comprising one or more process microchannels comprising
an upstream end,
a downstream end,
a first section, as described hereinbefore, which is adapted to contain an epoxidation catalyst, to receive a feed comprising an olefin and oxygen, and to cause conversion of at least a portion of the feed to form an olefin oxide in the presence of the epoxidation catalyst,
a second section positioned downstream of the first section, as described hereinbefore, which is adapted to receive the olefin oxide, to receive carbon dioxide, and to cause conversion of the olefin oxide to form a 1,2-carbonate, and
a third section positioned downstream of the first section which is adapted to receive the 1,2-carbonate, to receive water or an alcohol, and to cause conversion of the 1,2-carbonate to form a 1,2-diol.

The conversion of the 1,2-carbonate with water or an alcohol in the third section of the one or more process microchannels may be a thermal conversion, but preferably it is a catalytic process. The temperature may be in the range of from 50 to 250° C., in particular from 80 to 200° C., more in particular from 100 to 180° C. Suitable catalysts are basic inorganic compounds, such as, for example, hydroxides of alkali metals, alkaline earth metals and metals selected from Groups 3-12 of the Periodic Table of the Elements; basic refractory oxides, such as, for example, basic aluminum oxide; and basic zeolites. Suitable alkali metals are, for example, lithium, sodium and potassium. Suitable alkaline earth metals may be, for example, calcium and magnesium. Suitable metals from Groups 3-12 of the Periodic Table of the Elements are, for example, zirconium and zinc. Other suitable catalysts are those known from U.S. Pat. No. 4,283,580, which is incorporated herein by reference. More suitable catalysts comprise a metalate or bicarbonate immobilized on a solid carrier having one or more electropositive sites. The metalate is a metal oxide anion wherein the metal has a positive functional oxidation state of at least +3 and it is polyvalent (i.e. the metal can have more than one valency). The polyvalent metal is preferably selected from Groups 5 and 6 of the Periodic Table, and more preferably from tungsten, vanadium, and, in particular, molybdenum. Typical examples of such metalate anions include anions conventionally characterized by the formulae $[MoO_4]^{2-}$, $[VO_3]^-$, $[V_2O_7H]^{3-}$, $[V_2O_7]^{4-}$, and $[WO_4]^{2-}$. It is appreciated the exact formulae of these metalate anions may vary with the process conditions at which they are used. However, these formulae are commonly accepted as representing a fair characterization of the metalate anions in question. The bicarbonate may or may not be formed in situ from hydroxyl anions or carbonate anions by reaction with water and carbon dioxide. The solid carrier having one or more electropositive sites includes inorganic carriers, for example silica, silica alumina, zeolites, and resins containing a quaternary ammonium, quaternary phosphonium, quaternary arsenonium, quaternary stibonium or a quaternary sulfonium cation, or a complexing macrocycle, for example a crown ether. The cation, or complexing macrocycle may or may not be separated from the backbone of the resin by a spacer group suitably containing alkylene group optionally containing one or more oxygen atoms between methylene moieties. The resin may have a polystyrene/divinylbenzene copolymer backbone, or a silica-based polymeric backbone, such as in polysiloxanes, or it may be a resin incorporating quaternized vinylpyridine monomers. The catalyst may comprise molybdate $[MoO_4]^{2-}$ or bicarbonate anions absorbed, by ion exchange from sodium molybdate or sodium bicarbonate, onto a commercially available ion exchange resin, for example Amberjet 4200 (Amberjet is a trademark).

The catalyst, when present as a solid material under the condition of the reaction, may be installed in the third section of the one or more process microchannels by known methods and applicable methods include, for example, filling at least a portion of the third section to form a packed bed, or covering at least a portion of the walls of the third section with the catalyst, for example by wash coating. Some of the methods related to the installation of an epoxidation catalyst, as set out hereinbefore, may be applicable to these catalysts in an analogous manner. In embodiments in which the catalyst represents itself as a liquid under the conditions of the reaction, the catalyst may be fed to the third section of the one or more process microchannels through the third feed channel and the one or more third orifices, suitably together with the water and/or alcohol feed. The molar ratio of the total of water and the alcohol to the 1,2-carbonate may be may be less than 10, in particular in the range of from 1 to 8, in particular from 1.1 to 6, for example from 1.2 to 4. The feed fed to the third section of the process microchannels may comprise a total quantity of the 1,2-carbonate, water and the alcohol of at least 60% w, in particular at least 80% w, more in particular at least 90% w, for example at least 95% w, relative to the total weight of the said feed. The pressure may be in the range of from 100 to 5000 kPa, in particular in the range of from 200 to 3000 kPa, more in particular in the range of from 500 to 2000 kPa, as measured at the third feed channel, described hereinbefore. The reaction conditions may be selected such that the conversion of the 1,2-carbonate is at least 50 mole-%, in particular at least 80 mole-%, more in particular at least 90 mole-%, for example at least 95 mole-%. Suitable alcohols for the conversion of the 1,2-carbonate into the 1,2-diol may be methanol, ethanol, propanol, isopropanol, 1-butanol and 2-butanol. Methanol is a preferred alcohol. Mixtures of alcohols and mixtures of water and one or more alcohols may be used. The conversion of 1,2-carbonate with one or more alcohols generally yields the carbonates corresponding with the one or more alcohols, in addition to a 1,2-diol. For example, conversion of ethylene carbonate with methanol generally yields ethylene glycol and dimethyl carbonate. The temperature of the epoxidation reaction mixture, including the olefin oxide, may be controlled before the olefin oxide enters the second section of the one or more process microchannels, so that the olefin oxide may adopt the desired temperature for the conversion to the 1,2-carbonate. The temperature of the carboxylation reaction mixture, including the 1,2-carbonate, may be controlled before the 1,2-carbonate enters the third section of the one or more process microchannels, so that the 1,2-carbonate may adopt the desired temperature for the conversion to the 1,2-diol. Thus, the one or more process microchannels may comprise additionally a first intermediate section downstream from the first section and upstream from the second section, which first intermediate section is adapted to control the temperature of the olefin oxide, and a second intermediate section downstream from the second section and upstream from the third section, which second intermediate section is adapted to control the temperature of the 1,2-carbonate. In particular, the reactor may comprise additionally one or more fourth heat exchange channels adapted to exchange heat with the first intermediate section of the said process microchannels and one or more fifth heat exchange channels adapted to exchange heat with the second intermediate section of the said process microchannels.

In some embodiments, the invention provides a process for the preparation of a 1,2-diol, a 1,2-diol ether, a 1,2-carbonate or an alkanol amine, which process comprises reacting in one or more process microchannels of a microchannel reactor an olefin oxide with water, an alcohol, carbon dioxide or an amine to form the 1,2-diol, 1,2-diol ether, 1,2-carbonate or alkanol amine. The processes and process conditions for reacting in a section of one or more process microchannels of a microchannel reactor an olefin oxide with water, an alcohol, carbon dioxide or an amine to form the 1,2-diol, 1,2-diol ether, 1,2-carbonate or alkanol amine, as described hereinbefore, are applicable in these embodiments.

In another embodiment, the invention provides a process for the preparation of a 1,2-diol, which process comprises converting in one or more process microchannels of a microchannel reactor a 1,2-carbonate with water or an alcohol to form the 1,2-diol. The processes and process conditions for converting in a section of one or more process microchannels of a microchannel reactor a 1,2-carbonate with water or an alcohol to form the 1,2-diol, as described hereinbefore, are applicable in these embodiments.

The 1,2-diols and 1,2 diol ethers, for example ethylene glycol, 1,2-propylene glycol and ethylene glycol ethers may be used in a large variety of industrial applications, for example in the fields of food, beverages, tobacco, cosmetics, thermoplastic polymers, curable resin systems, detergents, heat transfer systems, etc.

The 1,2-carbonates, for example ethylene carbonate, may be used as a diluent, in particular as a solvent. Ethanol amines may be used, for example, in the treating ("sweetening") of natural gas.

Unless specified otherwise, the organic compounds mentioned herein, for example the olefins, alcohols, 1,2-diols, 1,2-diol ethers, 1,2-carbonates, ethanol amines and organic halides, have typically at most 40 carbon atoms, more typically at most 20 carbon atoms, in particular at most 10 carbon atoms, more in particular at most 6 carbon atoms. Typically, the organic compounds have at least one carbon atom. As defined herein, ranges for numbers of carbon atoms (i.e. carbon number) include the numbers specified for the limits of the ranges.

The following examples are intended to illustrate the advantages of the present invention and are not intended to unduly limit the scope of the invention. The examples are prophetic examples describing how embodiments of this invention may be practiced.

Example 1

A microchannel reactor will comprise process microchannels, first heat exchange microchannels, second heat exchange microchannels and first feed channels. The process microchannels will comprise an upstream end, a first section and a second section.

The first section will be adapted to exchange heat with a heat exchange fluid flowing in the first heat exchange microchannels. The second heat exchange microchannels will comprise two sets of second heat exchange microchannels adapted to exchange heat with the second section, such that in the downstream portion of the second section a lower temperature will be achieved than in the upstream portion of the second section. A feed microchannel will end in the first section of the process microchannel through orifices. The orifices will be positioned at approximately equal distances into the downstream direction of the first section from the upstream end of the microchannel till two thirds of the length of the first section, and in the perpendicular direction the orifices will be positioned at approximately equal distances approximately across the entire width of the process microchannel.

The first section will comprise an epoxidation catalyst comprising silver, rhenium, tungsten, cesium and lithium deposited on a particulate carrier material, in accordance with the present invention. The particulate carrier material will be an α-alumina having a surface are of 1.5 m$^2$/g, a total pore volume of 0.4 ml/g, and a pore size distribution such that that pores with diameters in the range of from 0.2 to 10 μm represent 95% of the total pore volume, and that pores with diameters in the range of from 0.3 to 10 μm represent more than 92%, of the pore volume contained in the pores with diameters in the range of from 0.2 to 10 μm.

The microchannel reactor will be assembled in accordance with methods known from WO-A-2004/099113, and references cited therein. The carrier material will be deposited on the walls of the first section of the process microchannels by wash coating. Thereafter, the process microchannels will be assembled, and after assembly silver, rhenium, tungsten, cesium and lithium will be deposited on the carrier material by using methods, which are know per se from U.S. Pat. No. 5,380,697.

As an alternative, the microchannel reactor will be assembled, without prior wash coating, and after assembly the first section will be filled with a particulate epoxidation catalyst which will be prepared by milling and sieving a commercial HS-PLUS epoxidation catalyst, which may be obtained from CRI Catalyst Company, Houston, Tex., USA. In order to fill the first section, a dispersion of the milled and sieved catalyst in methanol will be introduced into the first section and the methanol will be removed from the first section.

In either alternative, the first section will be heated at 220° C. by heat exchange with the heat exchange fluid flowing in the first heat exchange microchannel, while ethylene is fed through an opening positioned at the upstream end of the process microchannels. A mixture of oxygen and ethyl chloride (3 parts by million by volume) will be fed through the feed channels. The molar ratio of oxygen to ethylene will be 1:1. The mixture exiting the first section and entering the second section of the process microchannels will be quenched in the second section in two steps, initially to a temperature of 150° C. and subsequently to a temperature of 80° C. The temperature and the feed rate of the ethylene and oxygen will be adjusted such that the conversion of ethylene is 97 mole-%. Then, the quantity of ethyl chloride in the mixture of oxygen and ethyl chloride will be adjusted so as to optimize the selectivity to ethylene oxide.

The ethylene oxide rich product may be purified by removing carbon dioxide and unconverted oxygen and ethylene. The purified ethylene oxide may be converted with water to yield ethylene glycol.

Example 2

A microchannel reactor will comprise process microchannels, first heat exchange microchannels, second heat exchange microchannels, third heat exchange microchannels, first feed channels and second feed channels. The process microchannels will comprise an upstream end, a first section, a first intermediate section, and a second section.

The first section will be adapted to exchange heat with a heat exchange fluid flowing in the first heat exchange microchannels. A first feed microchannel will end in the first section of the process microchannel through first orifices. The first orifices will be positioned at approximately equal distances into the downstream direction of the first section from the upstream end of the microchannel till two thirds of the length of the first section, and in the perpendicular direction the orifices will be positioned at approximately equal distances approximately across the entire width of the process microchannel. Second orifices will be positioned in a similar manner relative to the second section, and will connect the second feed microchannels with the second section of the process microchannels. The second heat exchange microchannels will comprise one set of second heat exchange microchannels adapted to exchange heat with the second section, such that in the second section a selected temperature will be maintained. The third heat exchange microchannels will comprise two sets of third heat exchange microchannels adapted to exchange heat with the first intermediate section, such that in the downstream portion of the first intermediate section a lower temperature will be achieved than in the upstream portion of the first intermediate section.

The first section will comprise an epoxidation catalyst comprising silver, rhenium, tungsten, cesium and lithium deposited on a particulate carrier material, in accordance with the present invention. The particulate carrier material will be an α-alumina having a surface are of 1.5 m$^2$/g, a total pore volume of 0.4 ml/g, and a pore size distribution such that that pores with diameters in the range of from 0.2 to 10 μm represent 95% of the total pore volume, and that pores with diameters in the range of from 0.3 to 10 μm represent more than 92%, of the pore volume contained in the pores with diameters in the range of from 0.2 to 10 μm.

The microchannel reactor will be assembled in accordance with methods known from WO-A-2004/099113, and references cited therein. The carrier material will be deposited on the walls of the first section of the process microchannels by wash coating. Thereafter, the process microchannels will be assembled, and after assembly silver, rhenium, tungsten, cesium and lithium will be deposited on the carrier material by using methods, which are know per se from U.S. Pat. No. 5,380,697.

As an alternative, the microchannel reactor will be assembled, without prior wash coating, and after assembly the first section will be filled with a particulate epoxidation catalyst which will be prepared by milling and sieving a commercial HS-PLUS epoxidation catalyst, which may be obtained from CRI Catalyst Company, Houston, Tex., USA.

In either alternative, the first section will be heated at 220° C. by heat exchange with the heat exchange fluid flowing in the first heat exchange microchannel, while ethylene is fed through an opening positioned at the upstream end of the process microchannels. A mixture of oxygen and ethyl chloride (3 parts by million by volume) will be fed through the feed channels. The molar ratio of oxygen to ethylene will be 1:1. The mixture exiting the first section and entering the first intermediate section of the process microchannels will be quenched in the first intermediate section in two steps, initially to a temperature of 150° C. and subsequently to a temperature of 80° C. The temperature and the feed rate of the ethylene and oxygen will be adjusted such that the conversion of ethylene is 97 mole-%. Then, the quantity of ethyl chloride in the mixture of oxygen and ethyl chloride will be adjusted so as to optimize the selectivity to ethylene oxide.

The quenched mixture comprising ethylene oxide and carbon dioxide exiting the first intermediate section and entering the second section will react in the second section in the presence of an aqueous solution of methyltributylphosphonium iodide, to form a mixture comprising ethylene oxide and ethylene carbonate. The aqueous solution of methyltributylphosphonium iodide will enter the second section through the second orifices. The temperature in the second section is maintained at 80° C. by heat exchange with a heat exchange fluid flowing in the second heat exchange microchannel.

The mixture comprising ethylene oxide and ethylene carbonate may be separated to provide ethylene oxide and ethylene carbonate, which may be purified separately. Purified ethylene oxide and optionally purified ethylene carbonate may be converted with water to yield ethylene glycol.

Example 3

A microchannel reactor will comprise process microchannels, first heat exchange microchannels, second heat exchange microchannels, third heat exchange channels, first feed channels and second feed channels. The process microchannels will comprise an upstream end, a first section, a first intermediate section, and a second section.

The first section will be adapted to exchange heat with a heat exchange fluid flowing in the first heat exchange microchannels. The third heat exchange microchannels will comprise two sets of third heat exchange microchannels adapted to exchange heat with the first intermediate section, such that in the downstream portion of the first intermediate section a lower temperature will be achieved than in the upstream portion of the first intermediate section. A first feed microchannel will end in the first section of the process microchannel through first orifices. The first orifices will be positioned at approximately equal distances into the downstream direction of the first section from the upstream end of the microchannel till two thirds of the length of the first section, and in the perpendicular direction the orifices will be positioned at approximately equal distances approximately across the entire width of the process microchannel. Second orifices will be positioned in a similar manner relative to the second section, and will connect the second feed microchannels with the second section of the process microchannels. The second heat exchange microchannels will comprise one set of second heat exchange microchannels adapted to exchange heat with the second sections, such that in the second section a selected temperature will be maintained.

The first section will comprise an epoxidation catalyst comprising silver, rhenium, tungsten, cesium and lithium deposited on a particulate carrier material, in accordance with the present invention. The particulate carrier material will be an α-alumina having a surface are of 1.5 m$^2$/g, a total pore volume of 0.4 ml/g, and a pore size distribution such that that pores with diameters in the range of from 0.2 to 10 μm represent 95% of the total pore volume, and that pores with diameters in the range of from 0.3 to 10 μm represent more than 92%, of the pore volume contained in the pores with diameters in the range of from 0.2 to 10 μm.

The microchannel reactor will be assembled in accordance with methods known from WO-A-2004/099113, and references cited therein. The carrier material will be deposited on the walls of the first section of the process microchannels by wash coating. Thereafter, the process microchannels will be assembled, and after assembly silver, rhenium, tungsten, cesium and lithium will be deposited on the carrier material by using methods, which are know per se from U.S. Pat. No. 5,380,697.

As an alternative, the microchannel reactor will be assembled, without prior wash coating, and after assembly the first section will be filled with a particulate epoxidation catalyst which will be prepared by milling and sieving a commercial HS-PLUS epoxidation catalyst, which may be obtained from CRI Catalyst Company, Houston, Tex., USA.

In either alternative, the first section will be heated at 220° C. by heat exchange with the heat exchange fluid flowing in the first heat exchange microchannel, while ethylene is fed through an opening positioned at the upstream end of the process microchannels. A mixture of oxygen and ethyl chloride (3 parts by million by volume) will be fed through the feed channels. The molar ratio of oxygen to ethylene will be 1:1. The mixture exiting the first section and entering the first intermediate section of the process microchannels will be quenched in the first intermediate section in two steps, initially to a temperature of 150° C. and subsequently to a temperature of 80° C. The temperature and the feed rate of the ethylene and oxygen will be adjusted such that the conversion of ethylene is 97 mole-%. Then, the quantity of ethyl chloride in the mixture of oxygen and ethyl chloride will be adjusted so as to optimize the selectivity to ethylene oxide.

The quenched mixture, comprising ethylene oxide, exiting the first intermediate section and entering the second section will react in the second section in the presence of a 1%-w aqueous solution of sulfuric acid, to convert ethylene oxide into ethylene glycol. The aqueous sulfuric acid solution will enter the second section through the second orifices. The molar ratio of water to ethylene oxide will be 3:1. The temperature in the second section is maintained at 80° C. by heat exchange with a heat exchange fluid flowing in the second heat exchange microchannel.

The reaction product, including ethylene glycol, may be separated and purified.

Example 4

A microchannel reactor will comprise process microchannels, first heat exchange microchannels, second heat exchange microchannels, third heat exchange microchannels, fourth heat exchange microchannels, fifth heat exchange channels, first feed channels, second feed channels and third feed channels. The process microchannels will comprise an upstream end, a first section, a first intermediate section, a second section, a second intermediate section, and a third section.

The first section will be adapted to exchange heat with a heat exchange fluid flowing in the first heat exchange microchannels. A first feed microchannel will end in the first section of the process microchannel through first orifices. The first orifices will be positioned at approximately equal distances into the downstream direction of the first section from the upstream end of the microchannel till two thirds of the length of the first section, and in the perpendicular direction the orifices will be positioned at approximately equal distances approximately across the entire width of the process microchannel. Second orifices will be positioned in a similar manner relative to the second section, and will connect the second feed microchannels with the second section of the process microchannels. Third orifices will be positioned in a similar manner relative to the third section, and will connect the third feed microchannels with the third section of the process microchannels. The second heat exchange microchannels will comprise one set of second heat exchange microchannels adapted to exchange heat with the second sections, such that in the second sections a selected temperature will be maintained. The third heat exchange microchannels will comprise one set of third heat exchange microchannels adapted to exchange heat with the third sections, such that in the third sections a selected temperature will be maintained. The fourth heat exchange microchannels will comprise two sets of fourth heat exchange microchannels adapted to exchange heat with the first intermediate section, such that in the downstream portion of the first intermediate section a lower temperature will be achieved than in the upstream portion of the first intermediate section. The fifth heat exchange microchannels will comprise one set of fifth heat exchange microchannels adapted to exchange heat with the second intermediate sections, such that in the second intermediate sections a selected temperature will be maintained.

The first section will comprise an epoxidation catalyst comprising silver, rhenium, tungsten, cesium and lithium deposited on a particulate carrier material, in accordance with the present invention. The particulate carrier material will be an α-alumina having a surface are of 1.5 m$^2$/g, a total pore volume of 0.4 ml/g, and a pore size distribution such that that pores with diameters in the range of from 0.2 to 10 μm represent 95% of the total pore volume, and that pores with diameters in the range of from 0.3 to 10 μm represent more than 92%, of the pore volume contained in the pores with diameters in the range of from 0.2 to 10 μm.

The microchannel reactor will be assembled in accordance with methods known from WO-A-2004/099113, and references cited therein. The carrier material will be deposited on the walls of the first section of the process microchannels by wash coating. Thereafter, the process microchannels will be assembled, and after assembly silver, rhenium, tungsten, cesium and lithium will be deposited on the carrier material by using methods, which are know per se from U.S. Pat. No. 5,380,697.

As an alternative, the microchannel reactor will be assembled, without prior wash coating, and after assembly the first section will be filled with a particulate epoxidation catalyst which will be prepared by milling and sieving a commercial HS-PLUS epoxidation catalyst, which may be obtained from CRI Catalyst Company, Houston, Tex., USA.

In either alternative, the first section will be heated at 220° C. by heat exchange with the heat exchange fluid flowing in the first heat exchange microchannel, while ethylene is fed through an opening positioned at the upstream end of the process microchannels. A mixture of oxygen and ethyl chloride (3 parts by million by volume) will be fed through the feed channels. The molar ratio of oxygen to ethylene will be 1:1. The mixture exiting the first section and entering the first intermediate section of the process microchannels will be quenched in the first intermediate section in two steps, initially to a temperature of 150° C. and subsequently to a temperature of 80° C. The temperature and the feed rate of the ethylene and oxygen will be adjusted such that the conversion of ethylene is 97 mole-%. Then, the quantity of ethyl chloride in the mixture of oxygen and ethyl chloride will be adjusted so as to optimize the selectivity to ethylene oxide.

The quenched mixture, comprising ethylene oxide, exiting the first intermediate section and entering the second section will react in the second section with carbon dioxide in the presence of a 1%-w aqueous solution of methyltributylphosphonium iodide, to convert ethylene oxide into ethylene carbonate. The aqueous methyltributylphosphonium iodide solution and carbon dioxide will enter the second section through the second orifices. The molar ratio of carbon dioxide to ethylene oxide will be 1.5:1. The temperature in the second section is maintained at 80° C. by heat exchange with a heat exchange fluid flowing in the second heat exchange microchannel.

The reaction mixture, comprising ethylene carbonate, exiting the second section and entering the second intermediate section will be heated in the second intermediate section to 90° C. by heat exchange with a heat exchange fluid flowing in the fifth heat exchange microchannel. Subsequently, the reaction mixture comprising ethylene carbonate will react in the third section with water in the presence of a 1%-w aqueous solution of potassium hydroxide, to convert ethylene carbonate into ethylene glycol. The aqueous potassium hydroxide solution will enter the third section through the third orifices. The molar ratio of water to ethylene carbonate will be 2:1. The temperature in the second section is maintained at 90° C. by heat exchange with a heat exchange fluid flowing in the third heat exchange microchannel.

The reaction product, including ethylene glycol, may be separated and purified.

That which is claimed is:

1. A process for the preparation of ethylene oxide, which process comprises introducing a source of oxygen into one or more process microchannels of a microchannel apparatus and introducing into the same process microchannels a source of ethylene, allowing mixing to take place to form a gaseous product mixture, and conveying the gaseous product mixture to a reactor wherein reaction to ethylene oxide occurs, wherein the microchannel apparatus is located in a recycle gas loop of an ethylene oxide manufacturing plant, wherein the ethylene oxide manufacturing plant comprises the reactor; an ethylene oxide absorber; a carbon dioxide absorber; and interconnecting pipework between the reactor, the ethylene oxide absorber, and the carbon dioxide absorber forming the recycle gas loop wherein the process conditions for the mixing are a pressure in the range of from 1000 to 3500 kPa, and a temperature in the range of from ambient to 250° C.

2. A process as claimed in claim 1, wherein the microchannel apparatus comprises one or more process microchannels having an internal height and/or width in the range of from 0.5 to 1.5 mm.

3. A process as claimed in claim 1, wherein the source of ethylene comprises a mixture of ethylene and one or more of ethane, oxygen, argon, carbon dioxide, nitrogen and methane, and the source of oxygen is a gas having an oxygen content in the range of from 15 to 99.99% by volume.

4. A process as claimed in claim 1, wherein the microchannel apparatus is located prior to the reactor.

5. A process as claimed in claim 1, wherein the source of oxygen is a gas having an oxygen content in the range of from 95 to 99.99% by volume.

6. A process for the preparation of ethylene oxide, which process comprises introducing a source of oxygen wherein the source of oxygen is a gas having an oxygen content in the range of from 95 to 99.99% by volume into one or more process microchannels of a microchannel apparatus and introducing into the same process microchannels a source of ethylene, allowing mixing to take place to form a gaseous product mixture, and conveying the gaseous product mixture to a reactor wherein reaction to ethylene oxide occurs, wherein the microchannel apparatus is located in a recycle gas loop of an ethylene oxide manufacturing plant, wherein the ethylene oxide manufacturing plant comprises the reactor; an ethylene oxide absorber; a carbon dioxide absorber; and interconnecting pipework between the reactor, the ethylene oxide absorber, and the carbon dioxide absorber forming the recycle gas loop.

7. A process as claimed in claim 6, wherein the microchannel apparatus comprises one or more process microchannels having an internal height and/or width in the range of from 0.5 to 1.5 mm.

8. A process as claimed in claim 6, wherein the microchannel apparatus is located prior to the reactor.

9. A process as claimed in claim 6 wherein the process conditions for the mixing are a pressure in the range of from 1000 to 3500 kPa, and a temperature in the range of from ambient to 250° C.

* * * * *